US00RE47267E

(19) United States
(12) Reissued Patent
Maeda et al.

(10) Patent Number: US RE47,267 E
(45) Date of Reissued Patent: *Mar. 5, 2019

(54) PYRIDINECARBOXAMIDES AS CXCR2 MODULATORS

(71) Applicant: Syntrix Biosystems, Inc., Auburn, WA (US)

(72) Inventors: Dean Y. Maeda, Seattle, WA (US); John A Zebala, Issaquah, WA (US)

(73) Assignee: Syntrix Biosystems, Inc., Auburn, WA (US)

( * ) Notice: This patent is subject to a terminal disclaimer.

(21) Appl. No.: 15/177,218

(22) Filed: Jun. 8, 2016

Related U.S. Patent Documents

Reissue of:
(64) Patent No.: 8,748,623
Issued: Jun. 10, 2014
Appl. No.: 12/707,647
Filed: Feb. 17, 2010

U.S. Applications:
(60) Provisional application No. 61/153,288, filed on Feb. 17, 2009.

(51) Int. Cl.

| | |
|---|---|
| ***C07D 401/00*** | (2006.01) |
| ***C07D 211/72*** | (2006.01) |
| ***A61K 31/44*** | (2006.01) |
| ***C07D 213/82*** | (2006.01) |
| ***C07D 413/12*** | (2006.01) |
| ***A61K 31/69*** | (2006.01) |
| ***C07F 5/02*** | (2006.01) |
| ***A61K 31/444*** | (2006.01) |
| ***C07D 401/12*** | (2006.01) |
| ***A61K 31/4439*** | (2006.01) |

(52) U.S. Cl.
CPC ..... *C07D 213/82* (2013.01); *A61K 31/44* (2013.01); *A61K 31/444* (2013.01); *A61K 31/4439* (2013.01); *A61K 31/69* (2013.01); *C07D 401/12* (2013.01); *C07D 413/12* (2013.01); *C07F 5/025* (2013.01)

(58) Field of Classification Search
CPC .. C07D 213/82; C07D 413/12; C07D 401/12; C07F 5/025; A61K 31/69; A61K 31/444; A61K 31/443; A61K 31/44
USPC ..... 514/64, 349; 546/268.4, 297
See application file for complete search history.

(56) References Cited

U.S. PATENT DOCUMENTS

| | | | | |
|---|---|---|---|---|
| 4,139,623 | A * | 2/1979 | Jaeggi et al. | 551/274 |
| 6,022,884 | A * | 2/2000 | Mantlo et al. | 514/352 |
| 6,506,747 | B1 | 1/2003 | Betageri et al. | |
| 6,521,395 | B1 * | 2/2003 | Begley et al. | 430/384 |
| 6,777,432 | B1 | 8/2004 | Cutshall et al. | |
| 7,084,164 | B2 * | 8/2006 | Tobe et al. | 514/383 |
| 7,151,112 | B1 * | 12/2006 | Cutshall | C07D 213/64 514/349 |
| 7,176,310 | B1 | 2/2007 | Baughman et al. | |
| 7,482,355 | B2 | 1/2009 | Ebden et al. | |
| 2004/0110802 | A1 | 6/2004 | Thorarensen et al. | |
| 2004/0116479 | A1 | 6/2004 | Haviv et al. | |
| 2006/0063790 | A1 | 3/2006 | Gillman et al. | |
| 2006/0063930 | A1 | 3/2006 | Agoston et al. | |
| 2006/0276515 | A1 * | 12/2006 | Cywin | C07D 213/56 514/343 |
| 2007/0015734 | A1 * | 1/2007 | McElroy et al. | 514/89 |
| 2007/0078172 | A1 * | 4/2007 | McElroy | A61K 31/00 514/355 |
| 2009/0163463 | A1 | 6/2009 | Bruce et al. | |
| 2010/0210593 | A1 | 8/2010 | Maeda et al. | |

FOREIGN PATENT DOCUMENTS

| | | | |
|---|---|---|---|
| JP | H06-505027 | A | 6/1994 |
| JP | H09-510471 | A | 10/1997 |
| JP | 2007-119451 | A | 5/2007 |
| JP | 2008-510726 | A | 4/2008 |
| JP | 2008-511675 | A | 4/2008 |
| JP | 2008-540433 | A | 11/2008 |
| JP | 2010-508269 | A | 3/2010 |
| JP | 2010-510272 | A | 4/2010 |
| JP | 2010-512418 | A | 4/2010 |
| JP | 2010-525056 | A | 7/2010 |
| JP | 2013-536234 | A | 9/2013 |
| WO | WO 1993/01010 | A1 | 5/1993 |
| WO | WO 1993/022312 | A1 | 11/1993 |
| WO | WO 1995/025723 | A1 | 9/1995 |
| WO | WO 2001/021615 | A1 | 3/2001 |
| WO | WO 2002/053544 | A1 | 7/2002 |
| WO | WO 2003/024448 | A2 | 3/2003 |
| WO | WO 2004/106296 | A2 | 12/2004 |
| WO | WO 2006/023844 | A2 | 3/2006 |
| WO | WO 2006/028958 | A2 | 3/2006 |

(Continued)

OTHER PUBLICATIONS

Patini et al. "Bioisosterism: A Rational Approach in Drug Design", Chem. Rev., 1996, vol. 96, No. 8, pp. 3147-3176.*

STN, RN #941285-77-4, Pub. Jul. 5, 2007.*

STN, RN# 1031968-79-2, Pub. Jul. 1, 2008.*

Cowan et al.; "Metabolic N-Oxidation of 3-Substituted Pyridines: Identification of Products by Mass Spectrometry"; Biomedical Mass Spectrometry; vol. 5 No. 9; Sep. 1978; p. 551-556.

U.S. Appl. No. 15/210,803, filed Jul. 14, 2016, Maeda et al.

U.S. Appl. No. 15/469,395, filed Mar. 24, 2017, Maeda et al.

(Continued)

*Primary Examiner* — Dwayne C. Jones

(74) *Attorney, Agent, or Firm* — Baker & Hostetler LLP

(57) ABSTRACT

There is disclosed pyridine-and pyrimidinecarboxamide compounds useful as pharmaceutical agents, synthesis processes, and pharmaceutical compositions which include pyridine-and pyrimidinecarboxamides compounds. More specifically, there is disclosed a genus of CXCR2 inhibitor compounds that are useful for treating a variety of inflammatory and neoplastic disorders.

80 Claims, 8 Drawing Sheets

(56) References Cited

FOREIGN PATENT DOCUMENTS

| | | | | | |
|---|---|---|---|---|---|
| WO | WO 2006/121719 | A2 | | 11/2006 | |
| WO | WO 2007/003962 | | * | 1/2007 | ..... C07D 211/08 |
| WO | WO 2007/028082 | | * | 3/2007 | ..... C07D 223/16 |
| WO | WO 2007026959 | A2 | * | 3/2007 | ..... C07D 333/54 |
| WO | WO 2007/098352 | | * | 8/2007 | ..... C07D 213/81 |
| WO | WO 2008/057282 | A1 | | 5/2008 | |
| WO | WO 2008/061795 | A2 | | 5/2008 | |
| WO | WO 2008/073461 | A2 | | 6/2008 | |
| WO | WO 2008/073936 | A1 | | 6/2008 | |
| WO | WO 2008/123469 | A1 | | 10/2008 | |
| WO | WO 2008/130320 | A2 | | 10/2008 | |
| WO | WO 2009/016088 | A1 | | 2/2009 | |
| WO | WO 2009/071476 | A1 | | 6/2009 | |
| WO | WO 2010/007382 | A1 | | 1/2010 | |
| WO | WO 2010/032875 | A2 | | 3/2010 | |
| WO | WO 2010/127978 | A1 | | 11/2010 | |
| WO | WO 2011/025838 | A1 | | 3/2011 | |
| WO | WO 2011/133888 | A1 | | 10/2011 | |
| WO | WO 2012/027289 | A1 | | 3/2012 | |

OTHER PUBLICATIONS de Krujif et al.; "Nonpeptidergic Allosteric Antagonists Differentially Bind to the CXCR2 Chemokine Receptor"; The Journal of Pharmacology and Experimental Therapeutics; vol. 329 No. 2; 2009; p. 783-790.

U.S. Appl. No. 15/354,838, filed Nov. 17, 2016, Zebala et al.

Maeda et al.; "Nicotinamide Glycolates Antagonize CXCR2 Activity through an Intracellular Mechanism"; The Journal of Pharmacology and Experimental Therapeutics; vol. 332 No. 1; 2010; p. 145-152.

Chemical Abstracts; Registration No. 1203367-39-8; Jan. 4, 2010; Supplier: Ambinter.

Chemical Abstracts; Registration No. 1208091-29-5; Mar. 8, 2010; Supplier: AA ChemBio.

Chemical Abstracts; Registration No. 1208091-20-6; Mar. 8, 2010; Supplier: AA ChemBio.

Chemical Abstracts; Registration No. 1208090-09-8; Mar. 8, 2010; Supplier: AA ChemBio.

Chemical Abstracts; Registration No. 1208089-82-0; Mar. 8, 2010; Supplier: AA ChemBio.

Chemical Abstracts; Registration No. 1060540-20-6; Oct. 13, 2008; Supplier: ChemBridge Corporation.

Brauch et al.; "Seven-component reactions by sequential chemoselective Ugi-Mumm/Ugi-Smiles reactions"; Chem. Commun.; vol. 46; 2010; p. 3387-3389.

Schuler et al.; Boronic Acid-Containing Aminopyridine- and Aminopyrimidinecarboxamide CXCR1/2 Antagonists: Optimization of Aqueous Solubility and Oral Bioavailability; Bioorganic & Medicinal Chemistry Letters; vol. 25(18); 2015; 16 pages.

Maeda et al.; "Boronic acid-containing CXCR1/2 antagonists; Optimization of metabolic stability, in vivo evaluation, and a proposed receptor binding model"; Bioorganic & Medicinal Chemistry Letters; vol. 25 No. 11; 2015; p. 2280-2284.

Kamath et al.; "Calculation of Relative Binding Free Energy Difference of DHFR Inhibitors by a Finite Difference Thermodynamic Integration (FDTI) Approach"; Journal of Biomolecular Structure & Dynamics; vol. 16 No. 6; 1991; p. 1239-1244.

Elworthy et al.; "N-Arylpiperazinyl-N'-propylamino Derivatives of Heteroaryl Amides as Functional Uroselective a1-Adrenoceptor Antagonists"; Journal of Medicinal Chemistry; vol. 40 No. 17; 1997; p. 2674-2687.

"3-Pyridinecarboxamide, N-methyl-N-(2-quinolinylmethyl)-6-[[(tetrahydro-2H-pyran-2-yl)methyl]amino]-"; Ambinter; RN 1203367-39-8; Jan. 24, 2010; 1 page.

Khlebnikov et al.; "Quantitative structure-activity relationships for small non-peptide antagonists of CXCR2: Indirect 3D approach using the frontal polygon method"; Biorganic & Medicinal Chemistry; vol. 14 Issue 2; Jan. 2006; p. 352-365.

Greco et al.; "Combination therapy: Opportunities and challenges for polymer-drug conjugates as anticancer nanomedicines"; Advanced Drug Delivery Reviews; vol. 61; 2009; p. 1203-1213.

Ha et al.; "Discovery of Novel CXCR2 Inhibitors Using Ligand-Based Pharmacophore Models"; Journal of Chemical Information and Modeling; vol. 55; 2015; p. 1720-1738.

Silverman, R. "The Organic Chemistry of Drug Design and Drug Action," 2004, Elsevier, pp. 29-32.*

Cutshall, N. et al., Bioorg. Med. Chem. Lett. 2002, vol. 12, pp. 1517-1520.*

CAPLUS 1967:443649.*

CAPLUS 1978:443236.*

CAPLUS 1986:148697.*

CAPLUS 1988:454789.*

CAPLUS 1988 528959.*

Busch-Petersen "Small Molecule Antagonists of the CXCR2 and CXCR1 Chemokine Receptors as Therapeutic Agents for the Treatment of Inflammatory Diseases" Curr Topics Med Chem. 6:1345-1352, 2006.

Nicholls et al. "Identification of a Putative Intracellular Allosteric Antagonist Binding-Site in the CXC Chemokine Receptors 1 and 2" Mol. Pharm. 74:1193-1202, 2008.

Cutshall et al. "Nicotinamide N-Oxides as CXCR2 Antagonists" Bioorganic Medicinal Chem. Lett. 11:1951-1954, 2001.

Cutshall et al.2 "Nicotinanilides as Inhibitors of Neutrophil Chemotaxis" Bioorganic Medicinal Chem. Lett. 1517-1520, 2002.

Maeda et al. J. Pharm. Exp. Ther. 332:145-152, 2010.

* cited by examiner

PYRIDINECARBOXAMIDES AS CXCR2 MODULATORS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

STATEMENT REGARDING FEDERALLY SPONSORED RESEARCH OR DEVELOPMENT

This invention was made with government support under grants 1R43HL072614, 5R44HL072614 awarded by the National Institutes of Health. The government has certain rights to this invention.

CROSS-REFERENCE TO RELATED [PATENT APPLICATION] *APPLICATIONS*

[This patent application] *This application is a reissue of U.S. patent application Ser. No. 12/707,647, filed Feb. 17, 2010, now U.S. Pat. No. 8,748,623, issued Jun. 10, 2014, which* claims priority to U.S. Provisional Patent Application *No.* 61/153,288 filed on [17] Feb. *17,* 2009*, the contents of which are incorporated herein by reference in their entirety.*

TECHNICAL FIELD

The present disclosure provides pyridine- and pyrimidinecarboxamides useful as pharmaceutical agents, synthesis processes, and pharmaceutical compositions which include pyridine- and pyrimidinecarboxamides compounds. More specifically, the present disclosure provides a genus of CXCR2 inhibitor compounds that are useful for treating a variety of inflammatory and neoplastic disorders.

BACKGROUND

Chemokines are chemotactic proteins that have the potential to attract macrophages, T-cells, eosinophils, basophils, neutrophils and endothelial cells to sites of inflammation and tumor growth. Chemokines are typically low molecular mass (7-9 kD) proteins that can be divided into four subfamilies: CC (or β-chemokines), CXC, C (or γ-chemokines) and CX3C (or δ-chemokines). The chemokines are categorized through their primary amino acid structure. The CXC subfamily is characterized by two conserved Cys residues (C) near the N-terminus and separated by an amino acid (X). The CXC-chemokines include, for example, interleukin-8 (IL-8), neutrophil-activating protein-1 (NAP-1), neutrophil-activating protein-2 (NAP-2), GROα, GROβ, GROγ, ENA-78, GCP-2, IP-10, MIG and PF4. The CXC subfamily of chemokines is further characterized by the presence or absence of a specific amino acid sequence, glutamic acid-leucine-arginine (or ELR for short) immediately before the first Cys residue of the CXC motif. Those chemokines with the ELR motif (ELRCXC) are important for the recruitment and activation of neutrophils to sites of inflammation. GROα and IL-8 are examples of ELRCXC chemokines.

The CXC-chemokines mediate their chemotactic activity through interaction with the chemokine receptors CXCR1 and CXCR2. CXCR1 binds IL-8 and GCP-2 with high affinity while CXCR2 binds all ELRCXC chemokines with high affinity.

Since CXC-chemokines promote the accumulation and activation of neutrophils, CXC-chemokines have been implicated in a wide range of acute and chronic inflammatory disorders including COPD, psoriasis and rheumatoid arthritis. (Baggiolini et al., FEBS Lett. 307, 97 (1992); Miller et al., Crit. Rev. Immunol. 12, 17 (1992); Oppenheim et al., Annu. Rev. Immunol. 9, 617 (1991); Seitz et al., J. Clin. Invest. 87, 463 (1991); Miller et al., Am. Rev. Respir. Dis. 146, 427 (1992); Donnely et al., Lancet 341, 643 (1998)).

ELRCXC chemokines, including IL-8, GROα, GROβ, GROγ, NAP-2, and ENA-78 (Stricter et al. J. Biol. Chem. 270 :27348-57, 1995), have also been implicated in the induction of tumor angiogenesis (new blood vessel growth). Angiogenic activity is due to ELRCXC-chemokine binding to, and activation of CXCR2, and possibly CXCR1 for IL-8, expressed on the surface of vascular endothelial cells (ECs) in surrounding vessels.

Many different types of tumors have been shown to produce ELRCXC chemokines. Chemokine production has been correlated with a more aggressive phenotype (Inoue et al. Clin. Cancer Res. 6:2104-2119, 2000) and poor prognosis (Yoneda et. al. J. Nat. Cancer Inst. 90:447-454, 1998). Chemokines are potent chemotactic factors and the ELRCXC chemokines, in particular, have been shown to induce EC chemotaxis. Thus, these chemokines are thought to induce chemotaxis of endothelial cells toward their site of production in the tumor. This may be a critical step in the induction of angiogenesis by the tumor. Inhibitors of CXCR2 or dual inhibitors of CXCR2 and CXCR1 will inhibit the angiogenic activity of the ELRCXC chemokines and therefore block the growth of the tumor. This anti-tumor activity has been demonstrated for antibodies to IL-8 (Arenberg et al. J. Clin. Invest. 97:2792-2802, 1996), ENA-78 (Arenberg et al., J. Clin. Invest. 102:465-72, 1998), and GROα (Haghnegandar et al., J. Leukoc. Biology 67:53-62, 2000).

Therefore, there is a need in the art to find CXCR2 inhibitor compounds and modulator compounds that can be used as pharmaceutical compounds. There remains a need for compounds that are capable of modulating activity at CXC-chemokine receptors. For example, conditions associated with an increase in IL-8 production (which is responsible for chemotaxis of neutrophil and T-cell subsets into the inflammatory site and growth of tumors) would benefit by compounds that are inhibitors of IL-8 receptor binding. The present disclosure was made to satisfy this need.

SUMMARY

The disclosure provides a pharmaceutical composition comprising at least one compound of the formula (1) or a pharmaceutically acceptable salt, or solvate thereof and a pharmaceutically acceptable carrier. In certain embodiments, this disclosure provides a novel class of compounds that are CXC chemokine-modulators, pharmaceutical compositions comprising one or more of such compounds, and methods of treatment, prevention, inhibition, or amelioration of one or more diseases associated with CXC chemokine mediation using the compounds and compositions disclosed herein.

The present disclosure further provides a compound comprising formula (1) or formula (2):

(1)

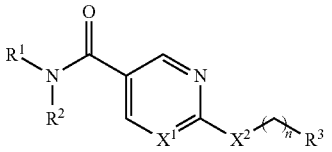

(2)

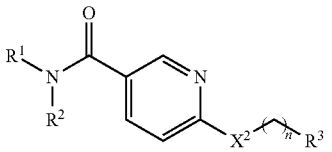

wherein $R^1$ and $R^2$ are independently selected from the group consisting of hydrogen, 2- or 3- or 4-halo-phenyl, heteroalkyl, alkyl, aryl, arylalkyl, heteroaryl, heteroarylalkyl, cycloalkyl, cycloalkylalkyl, heterocyclyl, and heterocyclylalkyl;

wherein $R^3$ is selected from —$B(R^4R^5)$, —$R^6$—$B(R^4R^5)$, $R^6$, —C(O)—$R^6$, —O—$R^6$, —$S(O)_y$—$R^6$ (wherein y=0, 1, or 2), —P(O)—$(R^4R^5)$ and —$N(R^7R^8)$;

wherein $R^6$ is selected from alkyl, aryl, arylalkyl, cycloalkyl, heteroaryl, heteroarylalkyl, heterocyclyl and heterocyclylalkyl;

wherein $R^4$ and $R^5$ are independently hydrogen, hydroxyl, aryloxy, or alkoxy, or wherein $R^4$ and $R^5$ together form a cyclic ester, or an acid anhydride (either mixed or symmetrical);

wherein $R^7$ and $R^8$ are independently selected from hydrogen, alkyl, haloalkyl, aryl, cycloalkyl, arylalkyl, heteroalkyl, heterocyclyl and heterocyclylalkyl; $R^7$ and $R^8$ are both oxygen to form a nitro group; or $R^7$ and $R^8$ together with the nitrogen to which they are attached, form a heterocyclyl; and wherein $X^1$ is carbon or nitrogen; $X^2$ is —$S(O)_y$— (wherein y=0, 1, or 2), nitrogen, or oxygen; and n is an integer between 0 and 8; and pharmaceutical compositions thereof.

Preferably, $X^1$ is carbon. Preferably, $R^1$ is hydrogen and $R^2$ is 4-fluoro-phenyl. Preferably, $X^2$ is sulfur. Preferably, the compound is compound #1 or compound #2 (Table 1).

The present disclosure further provides a pharmaceutical composition comprising a compound of formula (1) or formula (2):

(1)

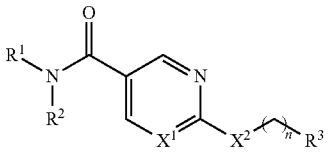

(2)

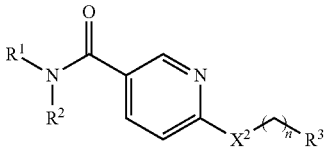

wherein $R^1$ and $R^2$ are independently selected from the group consisting of hydrogen, 2- or 3- or 4-halo-phenyl, heteroalkyl, alkyl, aryl, arylalkyl, heteroaryl, heteroarylalkyl, cycloalkyl, cycloalkylalkyl, heterocyclyl, and heterocyclylalkyl wherein $R^3$ is selected from —$B(R^4R^5)$, —$R^6$—$B(R^4R^5)$, $R^6$, or —C(O)—$R^6$, —O—$R^6$, —$S(O)_y$—$R^6$ (wherein y=0, 1, or 2), —P(O)—$(R^4R^5)$ and —$N(R^7R^8)$;

wherein $R^6$ is selected from alkyl, aryl, arylalkyl, cycloalkyl, heteroaryl, heteroarylalkyl, heterocyclyl and heterocyclylalkyl;

wherein $R^4$ and $R^5$ are independently hydrogen, hydroxyl, aryloxy, or alkoxy or wherein $R^4$ and $R^5$ together form a cyclic ester, or an acid anhydride (either mixed or symmetrical);

wherein $R^7$ and $R^8$ are independently selected from hydrogen, alkyl, haloalkyl, aryl, cycloalkyl, arylalkyl, heteroalkyl, heterocyclyl and heterocyclylalkyl; $R^7$ and $R^8$ are both oxygen to form a nitro group; or $R^6$ and $R^7$ together with the nitrogen to which they are attached, form a heterocyclyl; and wherein $X^1$ is carbon or nitrogen; $X^2$ is —$S(O)_y$— (wherein y=0, 1, or 2), nitrogen, or oxygen; and n is an integer between 0 and 8; and pharmaceutical compositions thereof.

Preferably, $X^1$ is carbon. Preferably, $R^1$ is hydrogen and $R^2$ is 4-fluoro-phenyl. Preferably, $X^2$ is sulfur. Preferably, the compound is compound #1 or compound #2 (Table 1).

The present disclosure provides a method for treating a disease or disorder selected from the group consisting of pain (e.g., acute pain, acute inflammatory pain, chronic inflammatory pain, and neuropathic pain), acute inflammation, chronic inflammation, rheumatoid arthritis, psoriasis, atopic dermatitis, asthma, bronchopulmonary dysplasia, COPD, adult respiratory disease, arthritis, inflammatory bowel disease, Crohn's disease, ulcerative colitis, septic shock, endotoxic shock, gram negative sepsis, toxic shock syndrome, stroke, ischemia reperfusion injury, renal reperfusion injury, glomerulonephritis, thrombosis, Alzheimer's disease, graft vs. host reaction (i.e., graft-versus-host disease), allograft rejections (e.g., acute allograft rejection, and chronic allograft rejection), malaria, acute respiratory distress syndrome, delayed type hypersensitivity reaction, atherosclerosis, cerebral ischemia, cardiac ischemia, osteoarthritis, multiple sclerosis, restinosis, angiogenesis, angiogenesis associated with tumor growth, osteoporosis, gingivitis, respiratory viruses, herpes viruses, hepatitis viruses, HIV, Kaposi's sarcoma associated virus (i.e., Kaposi's sarcoma), meningitis, cystic fibrosis, pre-term labor, cough, pruritis, multi-organ dysfunction, trauma, strains, sprains, contusions, psoriatic arthritis, herpes, encephalitis, CNS vasculitis, traumatic brain injury, systemic tumors, CNS tumors, tumors dependent on angiogenesis for growth, leukopenia and neutropenia, chemotherapy-induced leukopenia and neutropenia, opportunistic infections associated with neutropenia or leukopenia, sub-arachnoid hemorrhage, post surgical trauma, interstitial pneumonitis, hypersensitivity, crystal induced arthritis, acute pancreatitis, chronic pancreatitis, acute alcoholic hepatitis, necrotizing enterocolitis, chronic sinusitis, angiogenic ocular disease, ocular inflammation, retinopathy of prematurity, diabetic retinopathy, macular degeneration with the wet type preferred, corneal neovascularization, polymyositis, vasculitis, acne, gastric ulcers, duodenal ulcers, celiac disease, esophagitis, glossitis, airflow obstruction, airway hyperresponsiveness (i.e., airway hyperreactivity), bronchiectasis, bronchiolitis, bronchiolitis obliterans, chronic bronchitis, cor pulmonae, dyspnea, emphysema, hypercapnea, hyperinflation, hypoxemia, hyperoxia-induced inflammations, hypoxia, surgical lung volume reduction, pulmonary fibrosis, pulmonary hypertension, right ventricular hypertrophy, peritonitis associated with continuous ambulatory peritoneal dialysis (CAPD), granulocytic ehrlichiosis, sarcoidosis, small airway disease, ventilation-perfusion mismatching, wheeze, colds, gout, alcoholic liver disease, lupus, burn therapy (i.e., the treatment of burns), periodontitis, cancer, transplant reperfusion injury, and early transplantation rejection (e.g., acute allograft rejection) in a patient in need of such treatment, comprising administering an effective amount of a compound of formula (1) or formula (2):

(1)

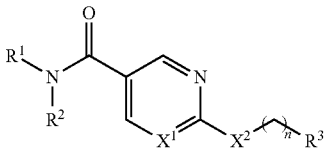

(2)

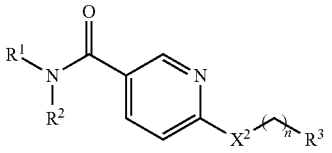

wherein $R^1$ and $R^2$ are independently selected from the group consisting of hydrogen, 2- or 3- or 4-halo-phenyl, heteroalkyl, alkyl, aryl, arylalkyl, heteroaryl, heteroarylalkyl, cycloalkyl, cycloalkylalkyl, heterocycyl, and heterocyclylalkyl;

wherein $R^3$ is selected from —$B(R^4R^5)$, $R^6$—$B(R^4R^5)$, $R^6$, —C(O)—$R^6$, —O—$R^6$, —$S(O)_y$—$R^6$ (wherein y=0, 1, or 2), —P(O)—$(R^4R^5)$ and —$N(R^7R^8)$;

wherein $R^6$ is selected from alkyl, aryl, arylalkyl, cycloalkyl, heteroaryl, heteroarylalkyl, heterocyclyl and heterocyclylalkyl;

wherein $R^4$ and $R^5$ are independently hydrogen, hydroxyl, aryloxy, or alkoxy, or wherein $R^4$ and $R^5$ together form a cyclic ester, or an acid anhydride (either mixed or symmetrical);

wherein $R^7$ and $R^8$ are independently selected from hydrogen, alkyl, haloalkyl, aryl, cycloalkyl, arylalkyl, heteroalkyl, heterocyclyl and heterocyclylalkyl; $R^7$ and $R^8$ are both oxygen to form a nitro group; or $R^7$ and $R^8$ together with the nitrogen to which they are attached, form a heterocyclyl; and wherein $X^1$ is carbon or nitrogen; $X^2$ is —$S(O)_y$— (wherein y=0, 1, or 2), nitrogen, or oxygen; and n is an integer between 0 and 8; and pharmaceutical compositions thereof.

Preferably, $X^1$ is carbon. Preferably, $R^1$ is hydrogen and $R^2$ is 4-fluoro-phenyl. Preferably, $X^2$ is sulfur. Preferably, the compound is compound #1 or compound #2 (Table 1).

DETAILED DESCRIPTION

Definitions

Figure 1:
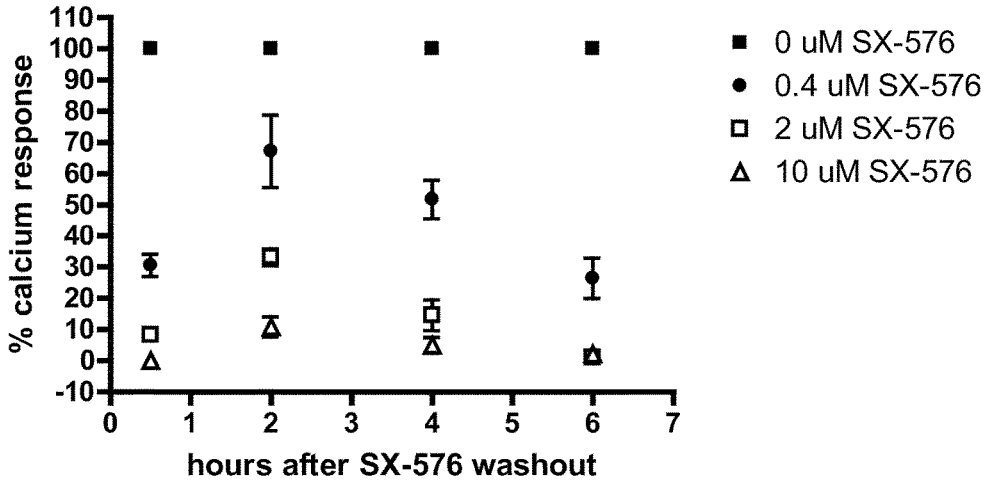
FIG. 1 illustrates long-lasting inhibition of GROα-mediated intracellular calcium flux in isolated human neutrophils treated with SX-576 (compound #2 in Table 1)

When any substituent or variable occurs more than one time in any moiety, its definition on each occurrence is independent of its definition at every other occurrence. Also, combinations of substituents and/or variables are permissible only if such combinations result in stable compounds.

Unless indicated otherwise, the following definitions apply throughout the present specification and claims. These definitions apply regardless of whether a term is used by itself or in combination with other terms. For example, the definition of "alkyl" also applies to the "alkyl" portion of the defined term "alkoxy".

"An effective amount" or a "therapeutically effective amount" means to describe an amount of compound of the present disclosure or another agent effective to treat a mammal (e.g., a human) having a disease or CXC chemokine-mediated condition, and thus producing the desired therapeutic effect.

"At least one" means one or more (e.g., 1-3, 1-2, or 1).

"Composition" includes a product comprising the specified ingredients in the specified amounts, as well as any product that results, directly or indirectly, from combination of the specified ingredients in the specified amounts.

"In combination with" as used to describe the administration of a compound of formula (1) with other medicaments in the methods of treatment of this invention, means that the compounds of formula (1) and formula (2) and the other medicaments are administered sequentially or concurrently in separate dosage forms, or are administered concurrently in the same dosage form.

"Mammal" means a human or other mammal, or means a human being.

"Patient" includes both human and other mammals, preferably human.

"Prodrug" denotes a compound that is a drug precursor which, upon administration to a subject, undergoes chemical conversion by metabolic or chemical processes to yield a compound of either formula (1) or formula (2) or a salt and/or solvate thereof. A discussion of pro-drugs is provided in T. Higuchi and V. Stella, Pro-drugs as Novel Delivery Systems, Volume 14 of the A.C.S. Symposium Series, and in Bioreversible Carriers in Drug Design, Edward B. Roche, ed., American Pharmaceutical Association and Pergamon Press, 1987, both of which are incorporated herein by reference.

"Alkyl" is a saturated or unsaturated, straight or branched, hydrocarbon chain. In various embodiments, the alkyl group has 1-18 carbon atoms, i.e. is a $C_1$-$C_{18}$ group, or is a $C_1$-$C_{12}$ group, a $C_1$-$C_6$ group, or a $C_1$-$C_4$ group. A lower alkyl group has 1-6 carbons. Independently, in various embodiments, the alkyl group has zero branches (i.e., is a straight chain), one branch, two branches, or more than two branches. Independently, in one embodiment, the alkyl group is saturated. In another embodiment, the alkyl group is unsaturated. In various embodiments, the unsaturated alkyl may have one double bond, two double bonds, more than two double bonds, and/or one triple bond, two triple bonds, or more than two triple bonds. Alkyl chains may be optionally substituted with 1 substituent (i.e., the alkyl group is mono-substituted), or 1-2 substituents, or 1-3 substituents, or 1-4 substituents, etc. The substituents may be selected from the group consisting of hydroxy, amino, alkylamino, boronyl, carboxy, nitro, cyano, and the like. When the alkyl group incorporates one or more heteroatoms, the alkyl group is referred to herein as a heteroalkyl group. When the substituents on an alkyl group are hydrocarbons, then the resulting group is simply referred to as a substituted alkyl. In various aspects, the alkyl group including substituents has less then 25, 24, 23, 22, 21, 20, 19, 18, 17, 16, 15, 14, 13, 12, 11, 10, 9, 8, or 7 carbons.

"Lower alkyl" means a group having about 1 to about 6 carbon atoms in the chain which chain may be straight or branched. Non-limiting examples of suitable alkyl groups include methyl, ethyl, n-propyl, isopropyl, n-butyl, t-butyl, and n-pentyl.

"Alkoxy" means an alkyl-O-group wherein alkyl is as defined above. Non-limiting examples of alkoxy groups include: methoxy, ethoxy, n-propoxy, isopropoxy, n-butoxy and heptoxy. The bond to the parent moiety is through the ether oxygen.

"Alkoxyalkyl" means an alkoxy-alkyl-group in which the alkoxy and alkyl are as previously described. Preferred alkoxyalkyl comprise a lower alkyl group. The bond to the parent moiety is through the alkyl.

"Alkylaryl" means an alkyl-aryl-group in which the alkyl and aryl are as previously described. Preferred alkylaryls comprise a lower alkyl group. The bond to the parent moiety is through the aryl.

"Aminoalkyl" means an $NH_2$-alkyl-group, wherein alkyl is as defined above, bound to the parent moiety through the alkyl group.

"Aryl" (sometimes abbreviated "Ar") is an aromatic carbocyclic hydrocarbon ring system. The ring system may be monocyclic or fused polycyclic (e.g., bicyclic, tricyclic, etc.). In one embodiment, the aryl group is monocyclic, and is preferably a $C_6$ ring system, i.e. a phenyl ring is a preferred aryl ring, where preferred bicyclic aryl rings are $C_8$-$C_{12}$, or $C_9$-$C_{10}$. A naphthyl ring, which has 10 carbon atoms, is a preferred polycyclic aryl ring. Unless otherwise indicated herein, the term "aryl" as used herein is meant to include aryl rings optionally substituted by one or more substituents selected from acyl (—C(O)—R), alkoxy (—O—R), alkyl, aryl, alkylamino (—N(H)—R and —N(R)R), alkylthio (—S—R), amino (—$NH_2$), azido (—$N_3$), boronyl (—B(R)R or —$B(OH)_2$ or —$B(OR)_2$), carboxy (—C(O)—OH), alkoxycarbonyl (—C(O)—OR), aminocarbonyl (—C(O)—$NH_2$), aminosulfonyl (—$S(O)_2$—$NH_2$), alkylaminocarbonyl (—C(O)—N(H)R and —C(O)—N(R)R), cyano, halo (fluoro, bromo, chloro, iodo), haloalkyl, haloalkoxy, heterocyclyl, heteroalkyl, hydroxyl (—OH), acyloxy (—O—C(O)—R), ketone (—C(O)—R), substituted halomethylketone (—C(O)—$CH_mX_n$, where m+n=3, X=F, Cl, Br), mercapto (—SH and —S—R) and nitro (—$NO_2$) where each R group is an alkyl group having less than about 12 carbons, preferably where the R group is a lower alkyl group. Non-limiting examples of suitable aryl groups include: phenyl, naphthyl, indenyl, tetrahydronaphthyl, indanyl, anthracenyl, and fluorenyl.

"Arylalkyl" refers to an alkyl group as defined substituted by one or more aryl groups as defined below. Phenyl and naphthyl are preferred aryl groups in an arylalkyl group. A preferred alkyl group is methyl, so that a preferred arylalkyl group is benzyl or benzyl having one or more substituents on the phenyl ring. Unless otherwise indicated, the term "arylalkyl" as used herein is meant to include arylalkyl groups wherein the aryl ring therein is optionally substituted by one or more substituents selected from acyl (—C(O)—R), alkoxy (—O—R), alkyl, aryl, alkylamino (—N(H)—R and —N(R)R), alkylthio (—S—R), amino (—$NH_2$), azido (—$N_3$), boronyl (—B(R)R or —$B(OH)_2$ or —$B(OR)_2$), carboxy (—C(O)—OH), alkoxycarbonyl (—C(O)—OR), aminocarbonyl (—C(O)—$NH_2$), aminosulfonyl (—$S(O)_2$—$NH_2$), alkylaminocarbonyl (—C(O)—N(H)R and —C(O)—N(R)R), cyano, halo (fluoro, bromo, chloro, iodo), haloalkyl, haloalkoxy, heterocyclyl, heteroalkyl, hydroxyl (—OH), acyloxy (—O—C(O)—R), ketone (—C(O)—R), substituted halomethylketone (—C(O)—$CH_mX_n$, where m+n=3, X=F, Cl, Br), mercapto (—SH and —S—R) and nitro (—$NO_2$) where each R is an alkyl group having less than about 12 carbons, preferably where the R group is a lower alkyl group.

"Arylalkyl" means an aryl-alkyl-group in which the aryl and alkyl are as previously described. Preferred arylalkyls comprise a lower alkyl group. Non-limiting examples of suitable aralkyl groups include benzyl, 2-phenethyl and napthalenylmethyl. The bond to the parent moiety is through the alkyl.

"Aryloxy" means an aryl-O-group in which the aryl group is as previously described. Non-limiting examples of suitable aryloxy groups include phenoxy and naphthoxy. The bond to the parent moiety is through the ether oxygen.

"Carboxyalkyl" means an HOOC-alkyl-group, wherein alkyl is as defined above, bound to the parent moiety through the alkyl group.

"Chemokine" means a protein molecule involved in chemotaxis.

A "chemokine-mediated disease" means a disease of which at least one element or cause is related to the regulation of a CXC chemokine.

"Commercially available chemicals" and the chemicals used in the Examples set forth herein may be obtained from standard commercial sources, where such sources include, for example, Acros Organics (Pittsburgh, Pa.), Sigma-Adrich Chemical (Milwaukee, Wis.), Avocado Research (Lancashire, U.K.), Bionet (Cornwall, U.K.), Boron Molecular (Research Triangle Park, N.C.), Combi-Blocks (San Diego, Calif.), Eastman Organic Chemicals, Eastman Kodak Company (Rochester, N.Y.), Fisher Scientific Co. (Pittsburgh, Pa.), Frontier Scientific (Logan, Utah), ICN Biomedicals, Inc. (Costa Mesa, Calif.), Lancaster Synthesis (Windham, N.H.), Maybridge Chemical Co. (Cornwall, U.K.), Pierce Chemical Co. (Rockford, Ill.), Riedel de Haen (Hannover, Germany), Spectrum Quality Product, Inc. (New Brunswick, N.J.), TCI America (Portland, Oreg.), and Wako Chemicals USA, Inc. (Richmond, Va.).

"Compounds described in the chemical literature" may be identified through reference books and databases directed to chemical compounds and chemical reactions, as known to one of ordinary skill in the art. Suitable reference books and treatise that detail the synthesis of reactants useful in the preparation of compounds disclosed herein, or provide references to articles that describe the preparation of compounds disclosed herein, include for example, "Synthetic Organic Chemistry", John Wiley and Sons, Inc. New York; S. R. Sandler et al, "Organic Functional Group Preparations," $2^{nd}$ Ed., Academic Press, New York, 1983; H. O. House, "Modern Synthetic Reactions," $2^{nd}$ Ed., W. A. Benjamin, Inc. Menlo Park, Calif., 1972; T. L. Glichrist, "Heterocyclic Chemistry," $2^{nd}$ Ed. John Wiley and Sons, New York, 1992; J. March, "Advanced Organic Chemistry: reactions, Mechanisms and Structure," $5^{th}$ Ed., Wiley Interscience, New York, 2001; Specific and analogous reactants may also be identified through the indices of known chemicals prepared by the Chemical Abstract Service of the American Chemical Society, which are available in most public and university libraries, as well as through online databases (the American Chemical Society, Washington, D.C. www.acs.org may be contacted for more details). Chemicals that are known but not commercially available in catalogs may be prepared by custom chemical synthesis houses, where many of the standard chemical supply houses (e.g. those listed above) provide custom synthesis services.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. A multicyclic cycloalkyl substituent may include fused, Spiro, or bridged ring structures. Non-limiting examples of suitable monocyclic cycloalkyls include cyclopropyl, cyclobutyl, cyclopentyl, cyclohexyl, cycloheptyl and the like. Non-limiting examples of suitable multicyclic cycloalkyls include 1-decalin, norbornyl, adamantly and the like. Cycloalkyl substituents may be substituted or unsubstituted. In one embodiment, the cycloalkyl is unsubstituted. In another embodiment, the cycloalkyl is substituted with, e.g., 1 substituent (i.e., the cycloalkyl group is mono-substituted), or 1-2 substituents, or 1-3 substituents, or 1-4 substituents, etc. In one embodiment, the substituents that may be present on the cycloalkyl aliphatic ring are selected from acyl (—C(O)—R), alkoxy (—O—R), alkyl, aryl, alkylamino (—N(H)—R and —N(R)R), alkylthio (—S—R), amino ($—NH_2$), azido ($—N_3$), boronyl (—B(R)R or $—B(OH)_2$ or $—B(OR)_2$), carboxy (—C(O)—OH), alkoxycarbonyl (—C(O)—OR), aminocarbonyl ($—C(O)—NH_2$), aminosulfonyl ($—S(O)_2—NH_2$), alkylaminocarbonyl (—C(O)—N(H)R and —C(O)—N(R)R), cyano, halo (fluoro, bromo, chloro, iodo), haloalkyl, haloalkoxy, heterocyclyl, heteroalkyl, hydroxyl (—OH), acyloxy (—O—C(O)—R), ketone (—C(O)—R), substituted halomethylketone ($—C(O)—CH_mX_n$, where m+n=3, X=F, Cl, Br), mercapto (—SH and —S—R) and nitro ($—NO_2$) In one aspect the R group in the above substituents is an alkyl group having less than about 12 carbons, while in another aspect the R group is a lower alkyl group.

"Cycloalkylalkyl" means a cycloalkyl group bound to the parent moiety through an alkyl group. Non-limiting examples include: cyclopropylmethyl and cyclohexylmethyl.

"Cycloalkylaryl" means a cycloalkyl group bound to the parent moiety through an aryl group. Non-limiting examples include: cyclopropylphenyl and cyclohexylphenyl.

"Effective amount" or "therapeutically effective amount" is meant to describe an amount of compound or a composition of the present disclosure effective in decreasing or increasing (i.e., modulating) the action of a CXC chemokine at a CXC chemokine receptor and thus producing the desired therapeutic effect in a suitable patient.

"Fluoroalkoxy" means an alkoxy group as defined above wherein one or more hydrogen atoms on the alkoxy is or are replaced by a fluoro group.

"Fluoroalkyl" means an alkyl group as defined above wherein one or more hydrogen atoms on the alkyl are replaced by a fluoro group.

"Halo" means fluoro, chloro, bromo, or iodo groups. Preferred are fluoro, chloro or bromo, and more preferred are fluoro and chloro.

"Halogen" means fluorine, chlorine, bromine, or iodine. Preferred are fluorine, chlorine and bromine.

"Heteroalkyl" is a saturated or unsaturated, straight or branched, chain containing carbon and at least one heteroatom. The heteroalkyl group may, in various embodiments, have on heteroatom, or 1-2 heteroatoms, or 1-3 heteroatoms, or 1-4 heteroatoms. In one aspect the heteroalkyl chain contains from 1 to 18 (i.e., 1-18) member atoms (carbon and heteroatoms), and in various embodiments contain 1-12, or 1-6, or 1-4 member atoms. Independently, in various embodiments, the heteroalkyl group has zero branches (i.e., is a straight chain), one branch, two branches, or more than two branches. Independently, in one embodiment, the heteroalkyl group is saturated. In another embodiment, the heteroalkyl group is unsaturated. In various embodiments, the unsaturated heteroalkyl may have one double bond, two double bonds, more than two double bonds, and/or one triple bond, two triple bonds, or more than two triple bonds. Heteroalkyl chains may be substituted or unsubstituted. In one embodiment, the heteroalkyl chain is unsubstituted. In another embodiment, the heteroalkyl chain is substituted. A substituted heteroalkyl chain may have 1 substituent (i.e., by monosubstituted), or may have 1-2 substituents, or 1-3 substituents, or 1-4 substituents, etc. Exemplary heteroalkyl substituents include esters (—C(O)—O—R) and carbonyls (—C(O)—).

"Heterocyclic" (or "heterocycloalkyl" or "heterocyclyl") refers to a non-aromatic saturated monocyclic or multicyclic ring system comprising 3 to 10 ring atoms (e.g., 3 to 7 ring atoms), or 5 to 10 ring atoms, in which one or more of the atoms in the ring system is an element other than carbon, for example nitrogen, oxygen or sulfur, alone or in combination. There are no adjacent oxygen and/or sulfur atoms present in the ring system. Examples of heterocyclics or heterocycloalkyls include rings having 5 to 6 ring atoms. The prefix aza, oxa or thia before the heterocyclic or heterocycloalkyl root name means that at least a nitrogen, oxygen or sulfur atom, respectively, is present as a ring atom. The nitrogen or sulfur atom of the heterocyclic or heterocycloalkyl can be optionally oxidized to the corresponding N-oxide, S-oxide or S,S-dioxide. Any nitrogen atoms may be optionally quaternized. Non-limiting examples of monocyclic heterocyclic or heterocycloalkyl rings include: piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophen-yl, and tetrahydrothiopyranyl The heterocyclyl may be unsubstituted or substituted. In one embodiment, the heterocyclyl is unsubstituted. In another embodiment, the heterocyclyl is substituted. The substituted heterocyclyl ring may contain 1 substituent, or 1-2 substituents, or 1-3 substituents, or 1-4 substituents, etc. In one embodiment, the substituents that may be present on the heterocyclyl ring are selected from acyl (—C(O)—R), alkoxy (—O—R), alkyl, aryl, alkylamino (—N(H)—R and —N(R)R), alkylthio (—S—R), amino ($—NH_2$), azido ($—N_3$), boronyl (—B(R)R or $—B(OH)_2$ or $—B(OR)_2$), carboxy (—C(O)—OH), alkoxycarbonyl (—C(O)—OR), aminocarbonyl (—C(O)—$NH_2$), aminosulfonyl (—$S(O)_2$—$NH_2$), alkylaminocarbonyl (—C(O)—N(H)R and —C(O)—N(R)R), cyano, halo (fluoro, bromo, chloro, iodo), haloalkyl, haloalkoxy, heterocyclyl, heteroalkyl, hydroxyl (—OH), acyloxy (—O—C(O)—R), ketone (—C(O)—R), substituted halomethylketone (—C(O)—$CH_mX_n$, where m+n=3, X=F, Cl, Br), mercapto (—SH and —S—R) and nitro (—$NO_2$) In one aspect, the R group which is, or is part of the substituent attached to the heterocyclic ring is an alkyl group having less than about 12 carbons, while in another aspect the R group is a lower alkyl group.

"Heterocycloalkylalkyl" means a heterocycloalkyl-alkyl group, wherein said heterocycloalkyl and said alkyl are as defined above, bound to a parent moiety through the alkyl group.

"Heteroaryl" means an aromatic monocyclic or multicyclic ring system comprising 5 to 14 ring atoms, or 5 to 10 ring atoms, in which one or more of the ring atoms is an element other than carbon, for example nitrogen, oxygen or sulfur, alone or in combination. Heteroaryls can contain 5 to 6 ring atoms. The prefix aza, oxa or thio before the heteroaryl root name means that at least a nitrogen, oxygen or sulfur atom respectively, is present as a ring atom. A nitrogen atom of a heteroaryl can be optionally oxidized to the corresponding N-oxide. Any nitrogen atoms may be optionally quaternized. Non-limiting examples of heteroaryls include: pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, and benzothiazolyl. The heteroaryl may be unsubstituted or substituted. In one embodiment, the heteroaryl is unsubstituted. In another embodiment, the heteroaryl is substituted. The substituted heteroaryl ring may contain 1 substituent, or 1-2 substituents, or 1-3 substituents, or 1-4 substituents, etc. In one embodiment, the substituents that may be present on the heteroaryl ring are selected from acyl (—C(O)—R), alkoxy (—O—R), alkyl, aryl, alkylamino (—N(H)—R and —N(R)R), alkylthio (—S—R), amino (—$NH_2$), azido (—$N_3$), boronyl (—B(R)R or —$B(OH)_2$ or —$B(OR)_2$), carboxy (—C(O)—OH), alkoxycarbonyl (—C(O)—OR), aminocarbonyl (—C(O)—$NH_2$), aminosulfonyl (—$S(O)_2$—$NH_2$), alkylaminocarbonyl (—C(O)—N(H)R and —C(O)—N(R)R), cyano, halo (fluoro, bromo, chloro, iodo), haloalkyl, haloalkoxy, heterocyclyl, heteroalkyl, hydroxyl (—OH), acyloxy (—O—C(O)—R), ketone (—C(O)—R), substituted halomethylketone (—C(O)—$CH_mX_n$, where m+n=3, X=F, Cl, Br), mercapto (—SH and —S—R) and nitro (—$NO_2$) In one aspect, the R group which is, or is part of the substituent attached to the heteroaryl ring is an alkyl group having less than about 12 carbons, while in another aspect the R group is a lower alkyl group.

"Heteroaralkyl" or "heteroarylalkyl" means a heteroaryl-alkyl-group, in which the heteroaryl and alkyl are as previously described. Preferred heteroaralkyls can contain a lower alkyl group. Non-limiting examples of suitable aralkyl groups include pyridylmethyl, 2-(furan-3-yl)ethyl and quinolin-3-ylmethyl. The bond to the parent moiety is through the alkyl.

"Hydroxyalkyl" means an HO-alkyl-group, in which alkyl is previously defined. Preferred hydroxyalkyls contain lower alkyl. Non-limiting examples of suitable hydroxyalkyl groups include hydroxymethyl and 2-hydroxyethyl.

"Hydrate" is a solvate wherein the solvent molecule is $H_2O$.

"Solvate" means a physical association of a compound of this disclosure with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like.

The term "substituted" means substitution with specified groups other than hydrogen, or with one or more groups, moieties or radicals which can be the same or different, with each, for example, being independently selected.

Examples of "disease modifying antirheumatic drugs" (i.e., DMARDs) include, for example, methotrexate, aminopterin, sulfasalzine, leflunomide, TNFα directed agents (e.g., infliximab, etanercept, and adalimumab), IL-1 directed agents (e.g., anakinra) B cell directed agents (e.g., rituximab), T cell directed agents (e.g., alefacept, efalizumab, and CTLA4-1g), TNFα-converting enzyme inhibitors, interleukin-1 converting enzyme is inhibitors, and p38 kinase inhibitors.

The term "other classes of compounds indicated for the treatment of rheumatoid arthritis", as used herein, unless indicated otherwise, means: compounds selected from the group consisting of: IL-1 directed agents (e.g., anakinra); B cell directed agents (e.g., rituximab); T cell directed agents (e.g., alefacept, efalizumab, and CTLA4-1g), TNFα-converting enzyme inhibitors, interleukin-1 converting enzyme inhibitors, and p38 kinase inhibitors.

The compounds of formula (1) and formula (2) form salts that are also within the scope of this disclosure. Reference to a compound of formula (1) or formula (2) herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of formula (1) or formula (2) contains both a basic moiety, such as, but not limited to a pyridine or imidazole, and an acidic moiety, such as, but not limited to a carboxylic acid, zwitterions ("inner salts") may be formed and are included within the term "salt(s)" as used herein. The salts can be pharmaceutically acceptable (i.e., non-toxic, physiologically acceptable) salts, although other salts are also useful. Salts of the compounds of the formula (1) or formula (2) may be formed, for example, by reacting a compound of formula (1) or formula (2) with an amount of acid or base, such as an equivalent amount, in a medium such as one in which the salt precipitates or in an aqueous medium followed by lyophilization.

Exemplary acid addition salts include acetates, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, 2-napthalenesulfonates, nicotinates, nitrates, oxalates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates) undecanoates, and the like. Additionally, acids which are generally considered suitable for the formation of pharmaceutically useful salts from basic pharmaceutical compounds are discussed, for example, by S. Berge et al, J. Pharmaceutical Sciences (1977) 66(1)1-19; P. Gould, International J. Pharmaceutics (1986) 33 201-217; Anderson et al, The Practice of Medicinal Chemistry (1996), Academic Press, New York; and in The Orange Book (Food & Drug Administration, Washington, D.C. on their website). These disclosures are incorporated herein by reference herein.

Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine and the like. Basic nitrogen-containing groups may be quarternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl, and stearyl chlorides, bromides and iodides), arylalkyl halides (e.g., benzyl and phenethyl bromides), and others.

All such acid and base salts are intended to be pharmaceutically acceptable salts within the scope of the disclosure and all acid and base salts are considered equivalent to the free forms of the corresponding compounds for purposes of the disclosure.

Compounds of formula (1) or formula (2) can exist in unsolvated and solvated forms, including hydrated forms. In general, the solvated forms, with pharmaceutically acceptable solvents such as water, ethanol and the like, are equivalent to the unsolvated forms for the purposes of this disclosure.

Compounds of formula (1) or formula (2) and salts, solvates and prodrugs thereof, may exist in their tautomeric form (for example, as an amide or imino ether). All such tautomeric forms are contemplated herein as part of the present disclosure.

Also within the scope of the present disclosure are polymorphs of the compounds of this disclosure (i.e., polymorphs of the compounds of formula 1 are within the scope of this disclosure).

Prodrugs of the compounds of formula (1) or formula (2) or pharmaceutically acceptable salts or solvates thereof are within the scope of this disclosure.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this disclosure. Individual stereoisomers of the compounds of this disclosure may, for example, be substantially free of other isomers, or may be admixed, for example, as racemates or with all other, or other selected, stereoisomers. The chiral centers of the compounds herein can have the S or R configuration as defined by the IUPAC 1974 Recommendations. The use of the terms "salt", "solvate", "prodrug" and the like, is intended to equally apply to the salt, solvate and prodrug of enantiomers, stereoisomers, rotamers, tautomers, racemates or prodrugs of the disclosed compounds.

Classes of compounds that can be used as the chemotherapeutic agent (antineoplastic agent) include: alkylating agents, antimetabolites, natural products and their derivatives, hormones and steroids (including synthetic analogs), and synthetics. Examples of compounds within these classes are given below.

Alkylating agents (including nitrogen mustards, ethylenimine derivatives, alkyl sulfonates, nitrosoureas and triazenes): Uracil mustard, Chlormethine, Cyclophosphamide, Ifosfamide, Melphalan, Chlorambucil, Pipobroman, Triethylene-melamine, Triethylenethiophos-phoramine, Busulfan, Carmustine, Lomustine, Streptozocin, Dacarbazine, and Temozolomide.

Antimetabolites (including folic acid antagonists, pyrimidine analogs, purine analogs and adenosine deaminase inhibitors): Methotrexate, Aminopterin, 5-Fluorouracil, Floxuridine, Cytarabine, 6-Mercaptopurine, 6-Thioguanine, Fludarabine phosphate, Pentostatine, and Gemcitabine.

Natural products and their derivatives (including vinca alkaloids, antitumor antibiotics, enzymes, lymphokines and epipodophyllotoxins): Vinblastine, Vincristine, Vindesine, Bleomycin, Dactinomycin, Daunorubicin, Doxorubicin, Epirubicin, Idarubicin, paclitaxel (Taxol®), Mithramycin, Deoxycoformycin, Mitomycin-C, L-Asparaginase, Interferons (especially IFN-□, etoposide, and Teniposide.

Hormones and steroids (including synthetic analogs): 17β-Ethinylestradiol, Diethylstilbestrol, Testosterone, Prednisone, Fluoxymesterone, Dromostanolone propionate, Testolactone, Megestrolacetate, Tamoxifen, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, Zoladex.

Synthetics (including inorganic complexes such as platinum coordination complexes): Cisplatin, Carboplatin, Hydroxyurea, Amsacrine, Procarbazine, Mitotane, Mitoxantrone, Levamisole, and Hexamethylmelamine.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR), e.g., 2008 edition (Thomson P D R, Montvale, N.J. 07645-1742, 25 USA); the disclosure of which is incorporated herein by reference herein.

As used herein, a microtubule affecting agent is a compound that interferes with cellular mitosis, i.e., having an anti-mitotic effect, by affecting microtubule formation and/or action. Such agents can be, for instance, microtubule stabilizing agents or agents that disrupt microtubule formation.

Microtubule affecting agents useful in this disclosure are well known to those of skilled in the art and include, but are not limited to allocolchicinc (NSC 406042), Halichondrin B (NSC 609395), colchicine (NSC 757), colchicine derivatives (e.g., NSC 33410), dolastatin 10 (NSC 376128), maytansine (NSC 153858), rhizoxin (NSC 332598), paclitaxel (Taxol, NSC 125973), Taxol derivatives (e.g., derivatives (e.g., NSC 608832), thiocolchicine (NSC 361792), trityl cysteine (NSC 83265), vinblastine sulfate (NSC 49842), vincristine sulfate (NSC 67574), epothilone A, epothilone, and discodermolide (see Service, (1996) Science, 274:2009) estramustine, nocodazole, MAP4, and the like. Examples of such agents are also described in the scientific and patent literature, see, e.g., Bulinski (1997) J. Cell Sci. 110:3055-3064; Panda (1997) Proc. Natl. Acad. Sci. USA 94:10560-10564; Muhlradt (1997) Cancer Res. 57, 3344-3346; Nicolaou (1997) Nature 387:268-272; Vasquez (1997) Mol. Biol. Cell. 8:973-985; Panda (1996) J. Biol. Chem. 271:29807-29812.

Particularly, agents can be compounds with paclitaxel-like activity. These include, but are not limited to paclitaxel and paclitaxel derivatives (paclitaxel-like compounds) and analogues. Paclitaxel and its derivatives are available commercially. In addition, methods of making paclitaxel and paclitaxel derivatives and analogues are well known to those of skilled in the art (see, e.g., U.S. Pat. Nos. 5,569,729; 5,565,478; 5,530,020; 5,527,924; 5,508,447; 5,489,589; 5,488,116; 5,484,809; 5,478,854; 5,478,736; 5,475,120; 5,468,769; 5,461,169; 5,440,057; 5,422,364; 5,411,984; 5,405,972; and 5,296,506, the disclosures of which are incorporated by reference herein).

Additional microtubule affecting agents can be assessed using one of many such assays known in the art, e.g., a semiautomated assay which measures the tubulin-polymerizing activity of paclitaxel analogs in combination with a cellular assay to measure the potential of these compounds to block cells in mitosis (see Lopes (1997) Cancer Chemother. Pharmacol. 41:37-47).

Compounds

Tables 1-5 list examples of species within the genus of formula 1 of compounds. Each compound listed is given a number, and if efficacy data as a CXCR2 inhibitor or agonist is available, the right-hand column lists the relative efficacy of the compound on an $IC_{50}$ or $EC_{50}$ basis to describe the compound's inhibitory or agonist activity, respectively. The synthetic method is either A, B, C or D and each method is disclosed below.

TABLE 1

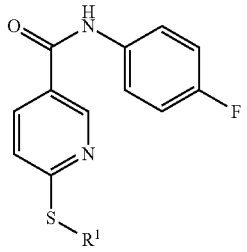

| Compound number | Synthetic method | $R^1$ | ESI-MS m/z $[M + H]^+$ | $IC_{50}$ (μM) |
|---|---|---|---|---|
| 1 (SX-517) | Synthesis Example 2 | 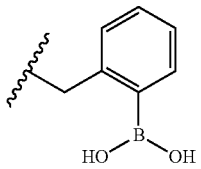 | 383.1 | 0.038 ± 0.003 |
| 2 (SX-576) | Synthesis Example 4 | 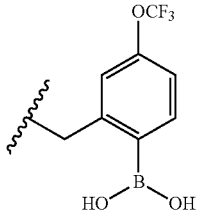 | 467.2 | 0.022 ± 2.9 |
| 3 | As in preparation of cmpd. 2 | 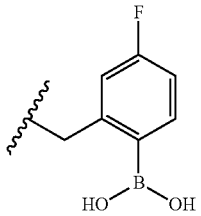 | 400.9 | 0.052 ± 0.005 |
| 4 | Synthesis Example 7 | 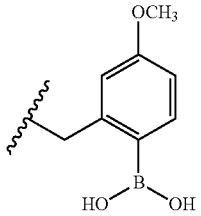 | 413.2 | 0.079 |

TABLE 1-continued
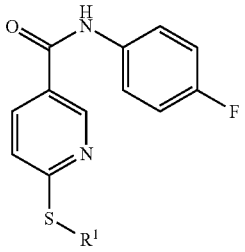
| Compound number | Synthetic method | $R^1$ | ESI-MS m/z $[M + H]^+$ | $IC_{50}$ (μM) |
|---|---|---|---|---|
| 5 | Synthesis Example 10 | | 443.1 | >10 |
| 6 | As in preparation of cmpd. 5 | | 427.2 | >10 |
| 7 | A | 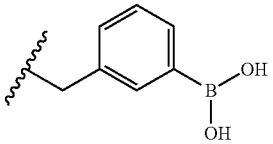 | 383.1 | 1.97 ± 0.75 |
| 8 | A | 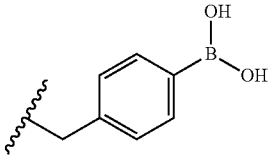 | 383.1 | 0.899 ± 0.15 |
| 9 | As in preparation of cmpd. 2 | 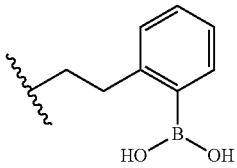 | 397.2 | 0.387 ± 0.125 |
| 10 | As in preparation of cmpd. 2 | 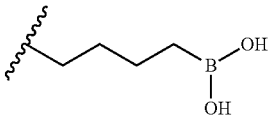 | 349.2 | 0.689 ± 0.23 |
| 12 | A | 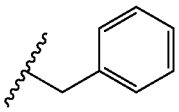 | 338.9 | 0.393 ± 0.16 |
| 13 (SX-578) | E | 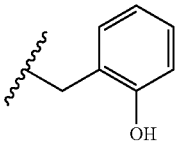 | 355.4 | 0.277 ± 0.089 |
| 13a | Synthesis Example 35 | 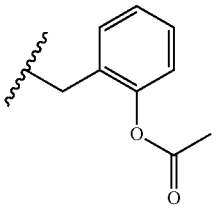 | 397.0 | >5 |

TABLE 1-continued
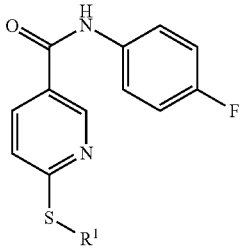
| Compound number | Synthetic method | $R^1$ | ESI-MS m/z $[M + H]^+$ | $IC_{50}$ (μM) |
|---|---|---|---|---|
| 14 (SX-585) | Synthesis Example 5 | 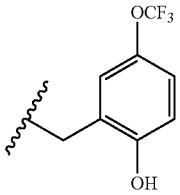 | 439.4 | 0.028 ± 0.006 |
| 14a | As in preparation of cmpd. 13a | 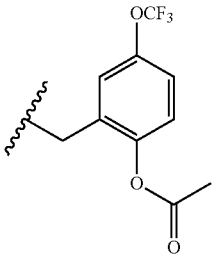 | 480.9 | 1.06 ± 0.27 |
| 15 | A | 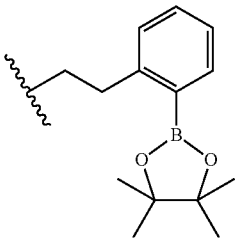 | 479.4 | 0.611 |
| 16 | A | 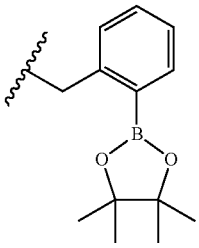 | 465.4 | 0.275 ± 0.103 |
| 17 | A | 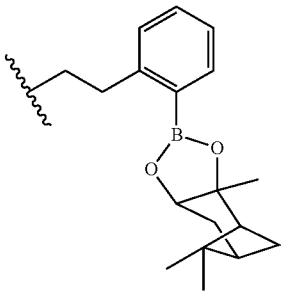 | 517.3 | 0.059 ± 0.029 |

TABLE 1-continued
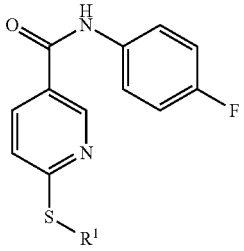
| Compound number | Synthetic method | $R^1$ | ESI-MS m/z $[M + H]^+$ | $IC_{50}$ (μM) |
|---|---|---|---|---|
| 18 | A | 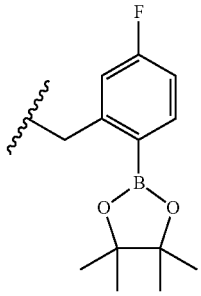 | 483.0 | 1.23 ± 0.12 |
| 19 | Synthesis Example 3 | 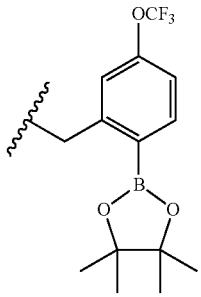 | 549.1 | 0.072 ± 0.007 |
| 20 | A | 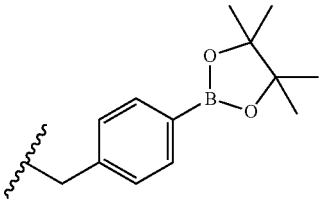 | 465.4 | 0.112 ± 0.067 |
| 21 | As in preparation of cmpd. 22 | 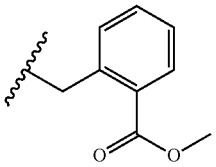 | 396.9 | 0.759 ± 0.19 |
| 22 | Synthesis Example 11 | 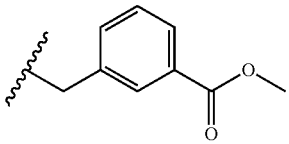 | 397.1 | >5 |

TABLE 1-continued
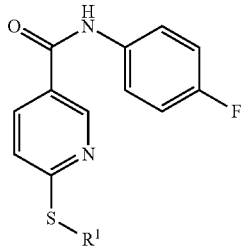
| Compound number | Synthetic method | $R^1$ | ESI-MS m/z $[M + H]^+$ | $IC_{50}$ (μM) |
|---|---|---|---|---|
| 23 | C | 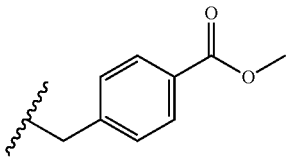 | 397.1 | >10 |
| 24 | As in preparation of cmpd. 25 | 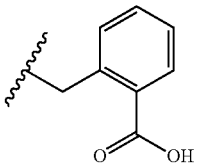 | 382.9 | 1.48 ± 0.49 |
| 25 | Synthesis Example 12 | 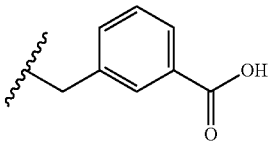 | 382.9 | 2.12 ± 0.74 |
| 26 | Synthesis Example 13 | 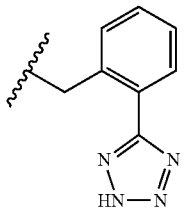 | 407.2 | 0.173 ± 0.046 |
| 27 | C | 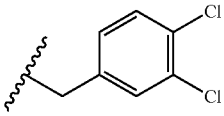 | 407.0 | 1.61 |
| 28 | C | 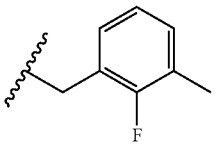 | 371.1 | >10 |
| 29 | C | 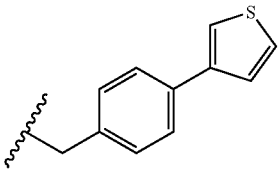 | 421.0 | >10 |

TABLE 1-continued
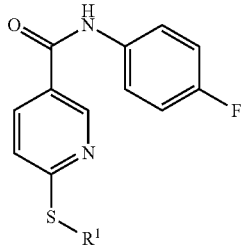
| Compound number | Synthetic method | $R^1$ | ESI-MS m/z $[M + H]^+$ | $IC_{50}$ (μM) |
|---|---|---|---|---|
| 30 | C | 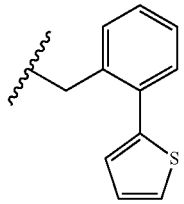 | 421.1 | >5 |
| 31 | C | 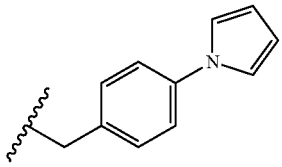 | 404.1 | >10 |
| 32 | C | 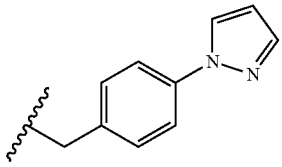 | 405.1 | >10 |
| 33 | C | 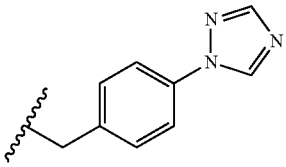 | 406.1 | >10 |
| 34 | C | 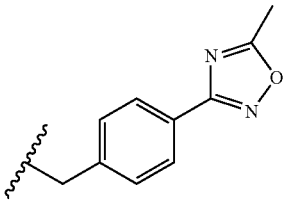 | 421.1 | >10 |
| 35 | C | 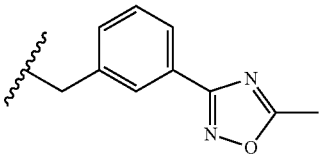 | 421.1 | >10 |

TABLE 1-continued
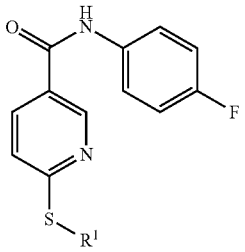
| Compound number | Synthetic method | $R^1$ | ESI-MS m/z $[M + H]^+$ | $IC_{50}$ (μM) |
|---|---|---|---|---|
| 36 | C | 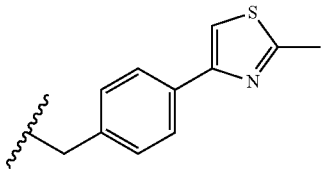 | 436.1 | >10 |
| 37 | C | 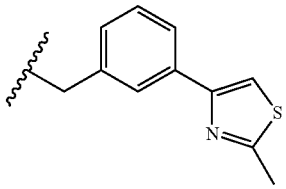 | 436.1 | >5 |
| 38 | C | 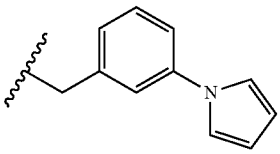 | 404.1 | >10 |
| 39 | C | 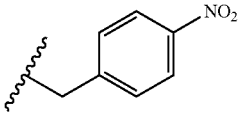 | 384.0 | >10 |
| 40 | B | 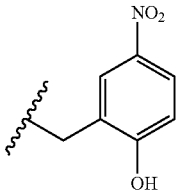 | 400.1 | >5 |
| 41 | C | 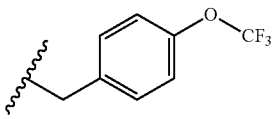 | 423.1 | >10 |
| 42 | C | 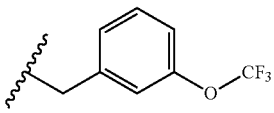 | 423.1 | >10 |
| 43 | B | 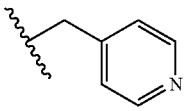 | 340.4 | >5 |

TABLE 1-continued
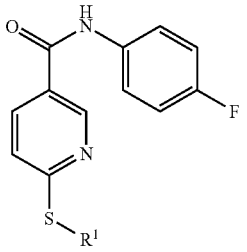
| Compound number | Synthetic method | $R^1$ | ESI-MS m/z $[M + H]^+$ | $IC_{50}$ (μM) |
|---|---|---|---|---|
| 44 | C | 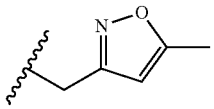 | 344.1 | >5 |
| 45 | C | 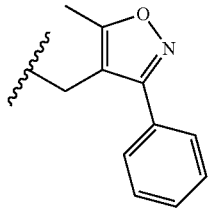 | 420.1 | >5 |
| 46 | C | 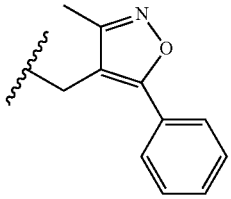 | 420.1 | >10 |
| 47 | C | 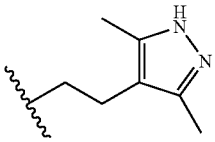 | 371.1 | >5 |
| 48 | C | 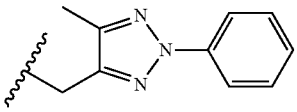 | 420.1 | >5 |
| 49 | Synthesis Example 14 | 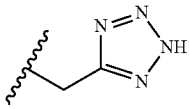 | 331.3 | 3.9 ± 1.2 |
| 50 | C | 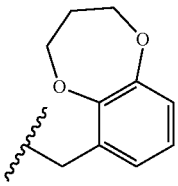 | 411.1 | 0.35 |
| 51 | C | 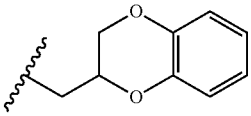 | 397.1 | 0.76 |

TABLE 1-continued
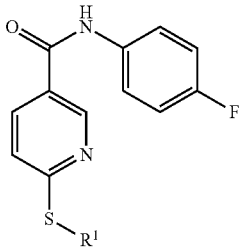
| Compound number | Synthetic method | $R^1$ | ESI-MS m/z $[M + H]^+$ | $IC_{50}$ (μM) |
|---|---|---|---|---|
| 52 | C | 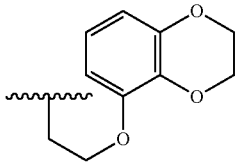 | 427.1 | 1.585 |
| 53 | C | 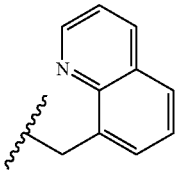 | 390.1 | >5 |
| 54 | C | 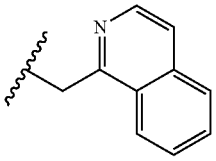 | 390.1 | >5 |
| 55 | C | 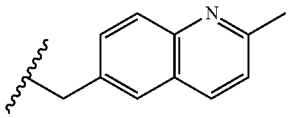 | 404.1 | >10 |
| 56 | C | 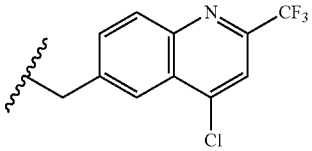 | 492.0 | >5 |
| 57 | B | 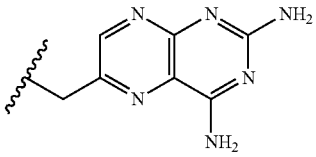 | 423.0 | >10 |
| 58 | C | 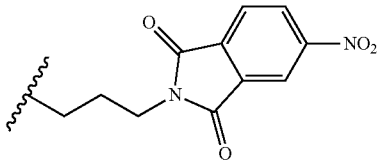 | 481.1 | >5 |

TABLE 1-continued
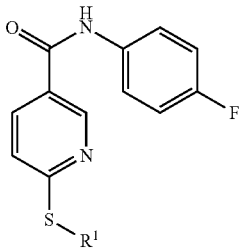
| Compound number | Synthetic method | $R^1$ | ESI-MS m/z $[M + H]^+$ | $IC_{50}$ (μM) |
|---|---|---|---|---|
| 59 | C | 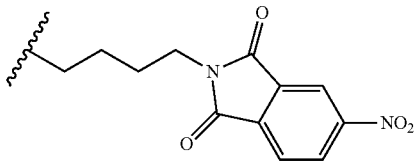 | 495.0 | >10 |
| 60 | C | 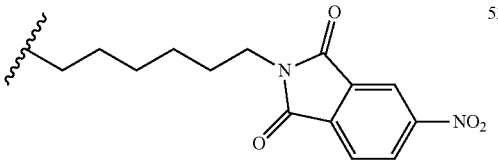 | 523.2 | >10 |
| 61 | C | 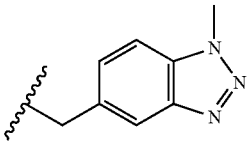 | 412.1 | >10 |
| 62 | C | 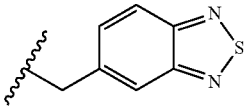 | 397.0 | >10 |
| 63 | C | 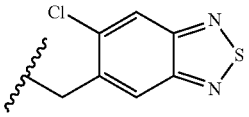 | 431.0 | >10 |
| 64 | C | 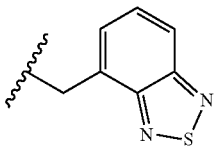 | 397.0 | >5 |
| 65 | C | 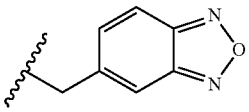 | 381.1 | 0.216 ± 0.066 |
| 66 | C | 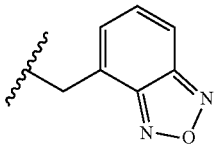 | 381.1 | >5 |

TABLE 1-continued
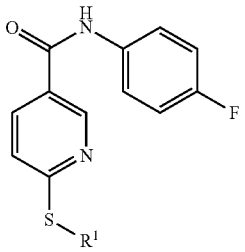
| Compound number | Synthetic method | $R^1$ | ESI-MS m/z $[M + H]^+$ | $IC_{50}$ (μM) |
|---|---|---|---|---|
| 67 | C | 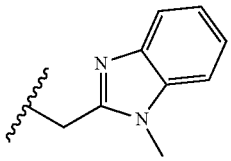 | 393.1 | >10 |
| 68 | C | 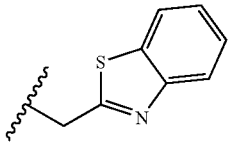 | 396.1 | >10 |
| 69 | C | 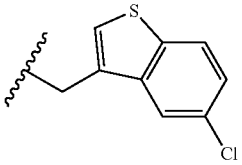 | 429.0 | >10 |
| 70 | C | 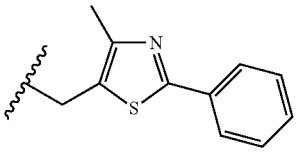 | 436.1 | 1.21 ± 0.39 |
| 71 | C | 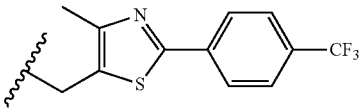 | 504.1 | >10 |
| 72 | C | 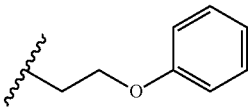 | 369.1 | >10 |
| 73 | C | 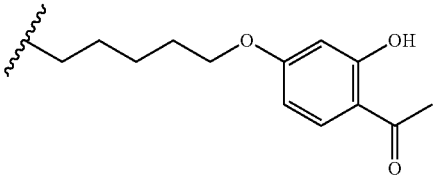 | 468.5 | >5 |
| 74 | C | 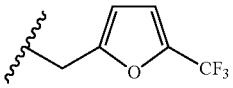 | 397.1 | >5 |

TABLE 1-continued
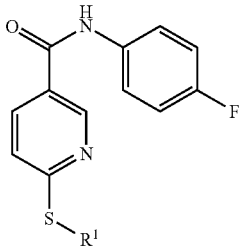
| Compound number | Synthetic method | $R^1$ | ESI-MS m/z $[M + H]^+$ | $IC_{50}$ (μM) |
|---|---|---|---|---|
| 75 | B | 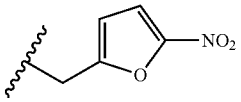 | 374.1 | >5 |
| 76 | C | 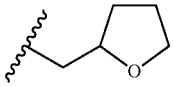 | 333.1 | 0.542 ± 0.104 |
| 77 | C | 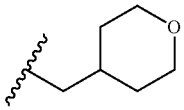 | 347.1 | >10 |
| 78 | A | 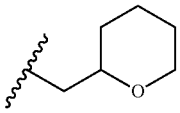 | 346.9 | >5 |
| 79 | C | 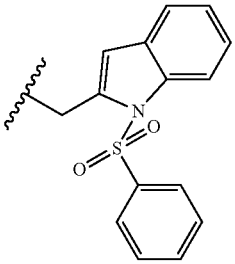 | 518.1 | >5 |
| 80 | C | 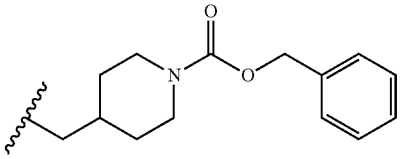 | 495.0 | >10 |
| 81 | B | 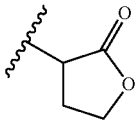 | 333.3 | >5 |
| 82 | B | 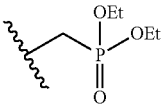 | 399.4 | >10 |
| 83 | B | 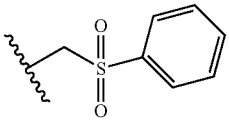 | 403.3 | >5 |

TABLE 1-continued
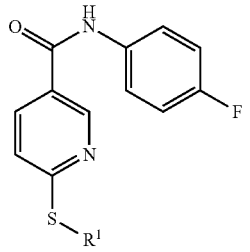
| Compound number | Synthetic method | $R^1$ | ESI-MS m/z $[M + H]^+$ | $IC_{50}$ (μM) |
|---|---|---|---|---|
| 84 | B | 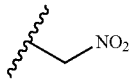 | 308.1 | >10 |
Abbreviation: cmpd. = compound.
TABLE 2
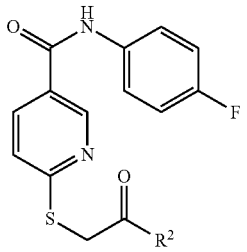
| Compound number | Synthetic method | $R^2$ | ESI-MS m/z $[M + H]^+$ | $IC_{50}$ (μM) |
|---|---|---|---|---|
| 85 | C | 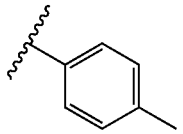 | 381.1 | >10 |
| 86 | C | 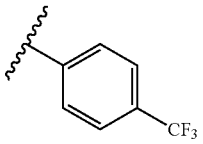 | 435.1 | >10 |
| 87 | C | 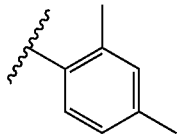 | 395.1 | >5 |
| 88 | C | 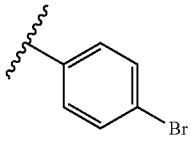 | 446.9 | >10 |

TABLE 2-continued
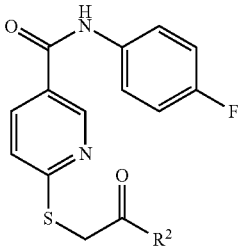
| Compound number | Synthetic method | $R^2$ | ESI-MS m/z $[M + H]^+$ | $IC_{50}$ (μM) |
|---|---|---|---|---|
| 89 | C | 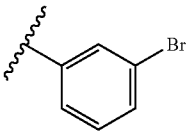 | 446.9 | 0.852 ± 0.292 |
| 90 | C | 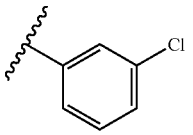 | 401.1 | 0.21 ± 0.19 |
| 91 | C | 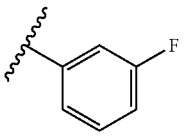 | 385.0 | >10 |
| 92 | C | 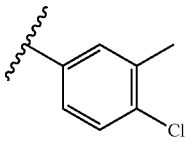 | 415.0 | >5 |
| 93 | C | 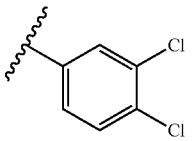 | 435.1 | 1.85 ± 0.55 |
| 94 | B | 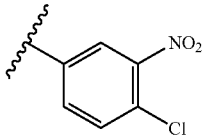 | 446.0 | 0.016 |
| 95 | C | 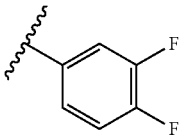 | 403.1 | >5 |
| 96 | C | 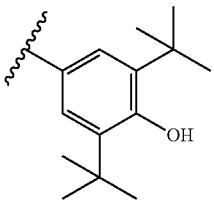 | 495.2 | >10 |

TABLE 2-continued
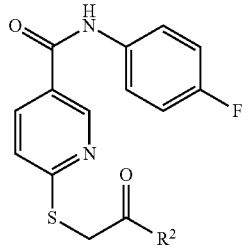
| Compound number | Synthetic method | $R^2$ | ESI-MS m/z $[M + H]^+$ | $IC_{50}$ (μM) |
|---|---|---|---|---|
| 97 | C | 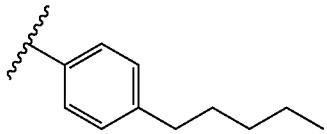 | 437.1 | >10 |
| 98 | C | 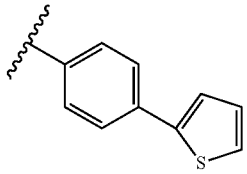 | 449.0 | >10 |
| 99 | C | 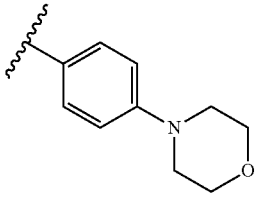 | 452.1 | >5 |
| 100 | C | 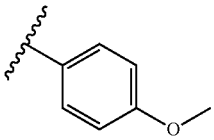 | 397.1 | >10 |
| 101 | C | 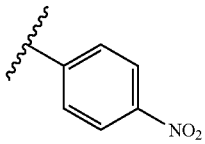 | 412.1 | >10 |
| 102 | C | 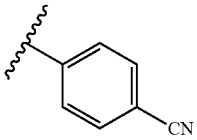 | 392.1 | >10 |
| 103 | C | 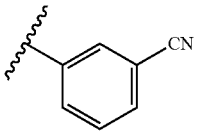 | 392.1 | >5 |

TABLE 2-continued
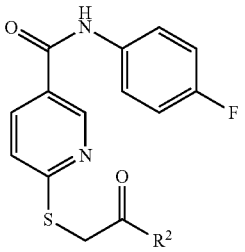
| Compound number | Synthetic method | $R^2$ | ESI-MS m/z $[M + H]^+$ | $IC_{50}$ (μM) |
|---|---|---|---|---|
| 104 | Synthesis Example 15 | 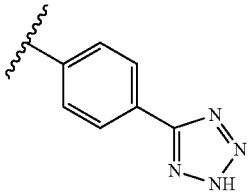 | 434.9 | 1.15 ± 0.47 |
| 105 | C | 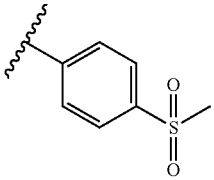 | 445.1 | >10 |
| 106 | C | 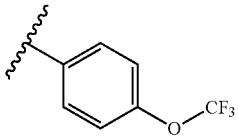 | 451.0 | >10 |
| 107 | C | 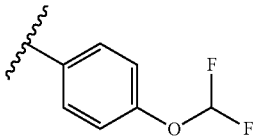 | 433.0 | >10 |
| 108 | C | 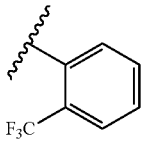 | 435.1 | >10 |
| 109 | C | 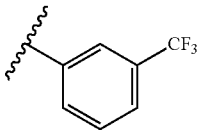 | 435.1 | >10 |
| 110 | C | 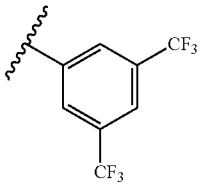 | 503.1 | >10 |

TABLE 2-continued
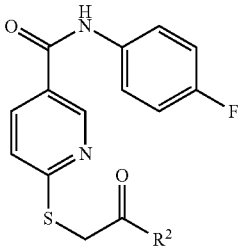
| Compound number | Synthetic method | $R^2$ | ESI-MS m/z $[M + H]^+$ | $IC_{50}$ (μM) |
|---|---|---|---|---|
| 111 | C | 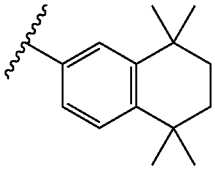 | 477.2 | >5 |
| 112 | C | 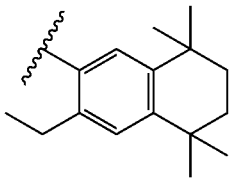 | 505.2 | 3.69 ± 0.72 |
| 113 | C | 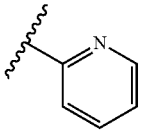 | 368.1 | >10 |
| 114 | C | 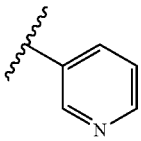 | 368.1 | >5 |
| 115 | C | 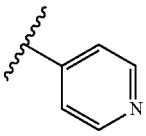 | 368.1 | >10 |
| 116 | C | 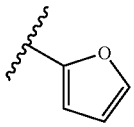 | 357.1 | >10 |
| 117 | C | 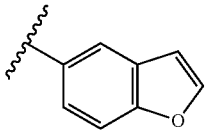 | 407.1 | >5 |
| 118 | C | 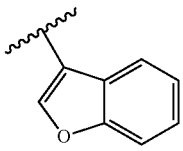 | 407.0 | >10 |

TABLE 2-continued
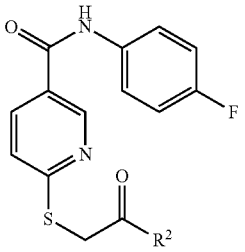
| Compound number | Synthetic method | $R^2$ | ESI-MS m/z $[M + H]^+$ | $IC_{50}$ (μM) |
|---|---|---|---|---|
| 119 | C | 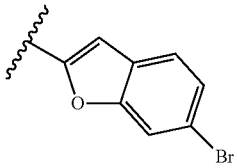 | 486.9 | 0.981 ± 0.29 |
| 120 | C | 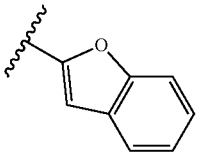 | 407.0 | >10 |
| 121 | C | 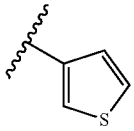 | 373.0 | >10 |
| 122 | C | 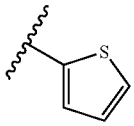 | 373.0 | >5 |
| 123 | C | 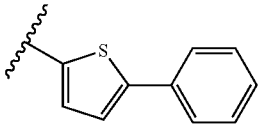 | 449.1 | >10 |
| 124 | C | 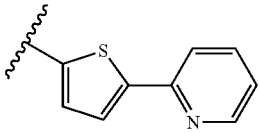 | 450.0 | >10 |
| 125 | C | 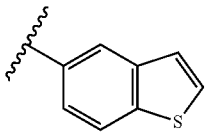 | 423.0 | >10 |
| 126 | C | 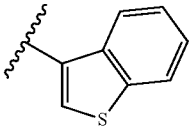 | 423.0 | >5 |

TABLE 2-continued
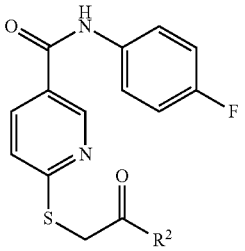
| Compound number | Synthetic method | $R^2$ | ESI-MS m/z $[M + H]^+$ | $IC_{50}$ (μM) |
|---|---|---|---|---|
| 127 | C | 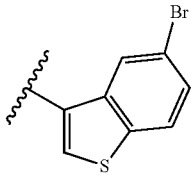 | 502.9 | 1.25 ± 0.32 |
| 128 | C | 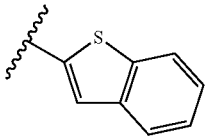 | 423.0 | 1.81 ± 0.52 |
| 129 | C | 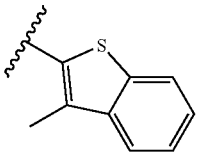 | 437.1 | >10 |
| 130 | C | 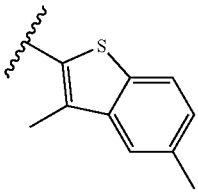 | 451.1 | >10 |
| 131 | C | 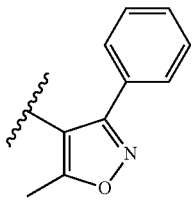 | 448.1 | >5 |
| 132 | C | 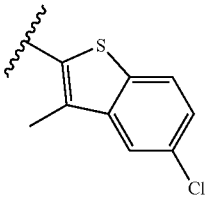 | 471.1 | 0.78 ± 0.51 |

TABLE 2-continued
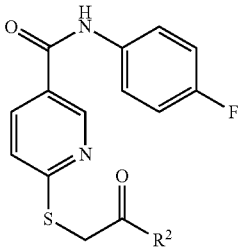
| Compound number | Synthetic method | $R^2$ | ESI-MS m/z $[M + H]^+$ | $IC_{50}$ (μM) |
|---|---|---|---|---|
| 133 | C | 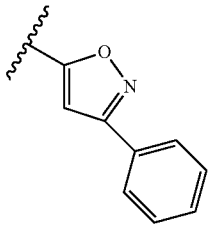 | 434.1 | >5 |
| 134 | C | 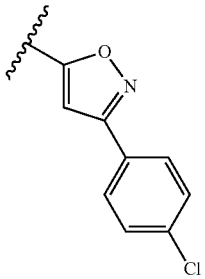 | 468.0 | >10 |
| 135 | C | 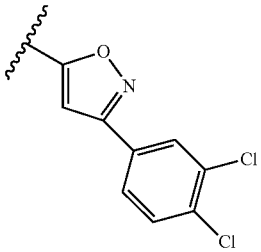 | 502.0 | >10 |
| 136 | C | 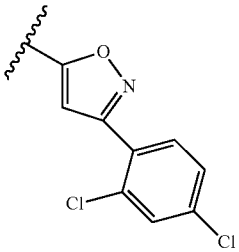 | 502.0 | >5 |
| 137 | Synthesis Example 36 | 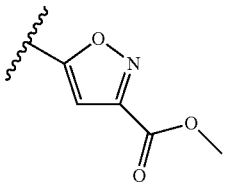 | 430.1 | 0.014 ± 0.003 |

TABLE 2-continued
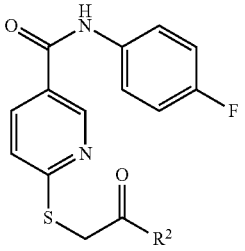
| Compound number | Synthetic method | $R^2$ | ESI-MS m/z $[M + H]^+$ | $IC_{50}$ (μM) |
|---|---|---|---|---|
| 138 | Synthesis Example 37 | 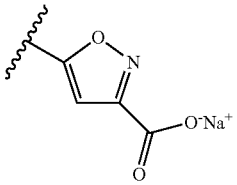 | 401.9 | 0.081 ± 0.010 |
| 139 | C | 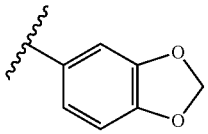 | 411.0 | >5 |
| 140 | C | 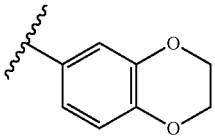 | 425.1 | 0.194 ± 0.052 |
| 141 | C | 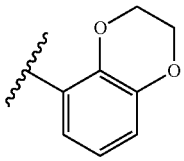 | 425.1 | >5 |
| 142 | C | 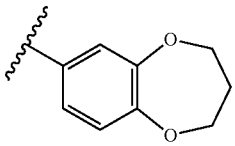 | 439.1 | >5 |
| 143 | C | 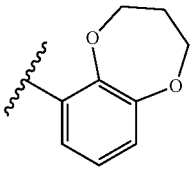 | 439.1 | >10 |
| 144 | C | 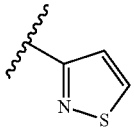 | 374.0 | 2.24 ± 0.71 |

TABLE 2-continued
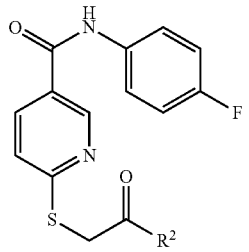
| Compound number | Synthetic method | $R^2$ | ESI-MS m/z $[M + H]^+$ | $IC_{50}$ (μM) |
|---|---|---|---|---|
| 145 | C | 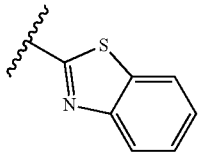 | 424.0 | >5 |
| 146 | C | 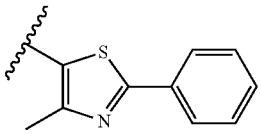 | 464.1 | >10 |
| 147 | C | 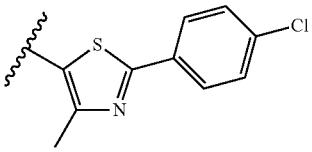 | 498.0 | >5 |
| 148 | C | 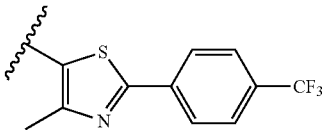 | 532.1 | >5 |
| 149 | C | 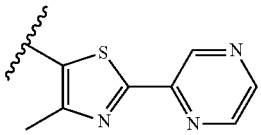 | 466.1 | >10 |
| 150 | C | 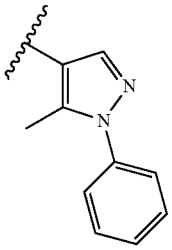 | 447.1 | >10 |
| 151 | C | 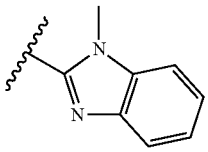 | 421.1 | 0.703 ± 0.291 |

TABLE 2-continued
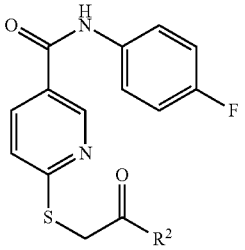
| Compound number | Synthetic method | $R^2$ | ESI-MS m/z $[M + H]^+$ | $IC_{50}$ (μM) |
|---|---|---|---|---|
| 152 | C | 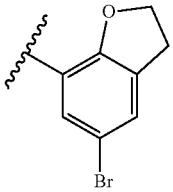 | 488.9 | 0.529 ± 0.44 |
| 153 | C | 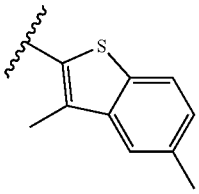 | 457.1 | 1.23 |
TABLE 3
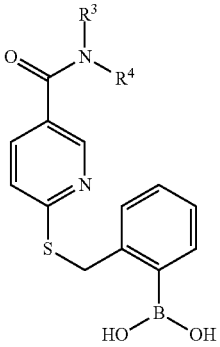
| Compound number | Synthetic method | $R^3$ | $R^4$ | ESI-MS m/z $[M + H]^+$ | $IC_{50}$ (μM) |
|---|---|---|---|---|---|
| 1 | Synthesis Example 2 | H | 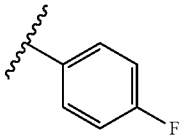 | 383.1 | 0.038 ± 0.003 |
| 154 | Synthesis Example 38 | 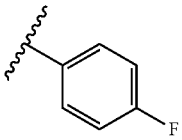 | 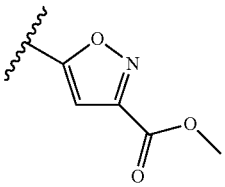 | 397.0 | >5 |

TABLE 3-continued
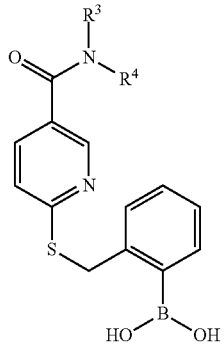
| Compound number | Synthetic method | $R^3$ | $R^4$ | ESI-MS m/z $[M + H]^+$ | $IC_{50}$ (μM) |
|---|---|---|---|---|---|
| 155 | Synthesis Example 18 | 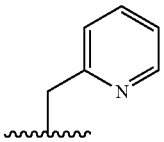 | 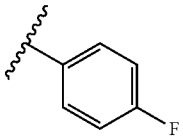 | 473.9 | 0.078 ± 0.018 |
| 156 | Synthesis Example 21 | 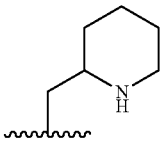 | 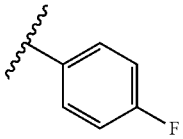 | 480.1 | >5 |
| 157 | As in preparation of cmpd. 155 | 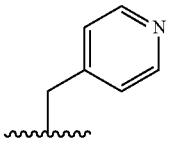 | 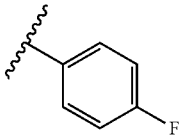 | 473.9 | 0.890 ± 0.67 |
| 158 | Synthesis Example 23 | 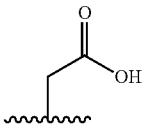 | 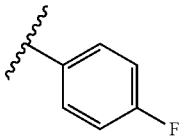 | 440.9 | 1.99 ± 0.46 |
| 159 | Synthesis Example 24 | H | 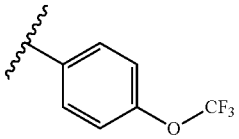 | 449.1 | 0.278 ± 0.148 |
| 160 | Synthesis Example 27 | H | 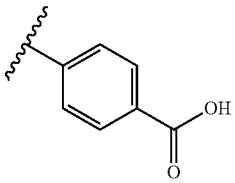 | 409.2 | >10 |
| 161 | Synthesis Example 28 | H | 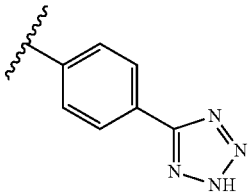 | 433.2 | >10 |

TABLE 3-continued
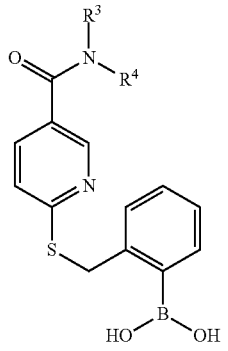
| Compound number | Synthetic method | $R^3$ | $R^4$ | ESI-MS m/z $[M + H]^+$ | $IC_{50}$ (μM) |
|---|---|---|---|---|---|
| 162 | As in preparation of cmpd. 160 | H | 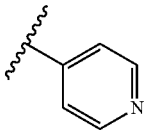 | 366.2 | 0.520 ± 0.263 |
| 163 | As in preparation of cmpd. 160 | H | 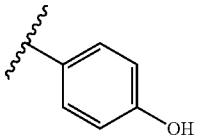 | 381.3 | 0.105 ± 0.044 |
| 164 | As in preparation of cmpd. 160 | H | 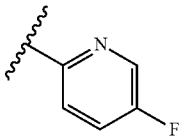 | 383.9 | 0.294 ± 0.119 |
| 165 | Synthesis Example 39 | H | 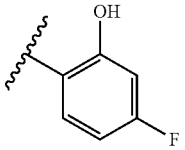 | 398.9 | 0.037 ± 0.007 |
| 166 | Synthesis Example 40 | H | 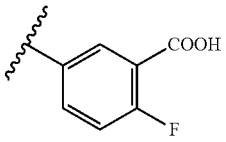 | 426.9 | >10 |
Abbreviation: cmpd. = compound.

TABLE 4

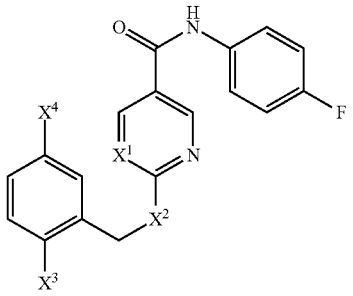

| Compound number | Synthetic method | $X^1$ | $X^2$ | $X^3$ | $X^4$ | ESI-MS m/z $[M + H]^+$ | $IC_{50}$ (μM) |
|---|---|---|---|---|---|---|---|
| 1 | Synthesis Example 2 | C | S | $B(OH)_2$ | H | 383.1 | 0.038 ± 0.003 |
| 167 | Synthesis Example 29 | N | S | $B(OH)_2$ | H | 384.0 | 0.116 ± 0.029 |
| 168 | Synthesis Example 33 | C | O | $B(OH)_2$ | H | 367.1 | 0.032 ± 0.002 |
| 169 | Synthesis Example 41 | C | O | H | H | 323.1 | 3.1 ± 0.49 |
| 170 | Synthesis Example 34 | 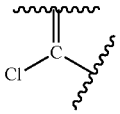 | S | $B(OH)_2$ | H | 471.0 | 0.166 ± 0.056 |
| 171 | F, cmpd 12 + 1 eq. mCPBA | C | S(O) | H | H | 355.0 | >10 |
| 172 | F, cmpd 12 + 2 eq. mCPBA | C | $S(O)_2$ | H | H | 371.1 | >10 |
| 173 | F, cmpd 1 + 2 eq. mCPBA | C | S(O) | OH | H | 371.1 | 7.21 ± 2.56 |
| 174 | F, cmpd 1 + 5 eq. mCPBA | C | S(O) | OH | H | 387.1 | 10.23 ± 0.86 |
| 175 | F, cmpd 2 + 2 eq. mCPBA | C | $S(O)_2$ | OH | $OCF_3$ | 455.0 | 1.23 ± 0.28 |
| 176 | F, cmpd 2 + 5 eq. mCPBA | C | $S(O)_2$ | OH | $OCF_3$ | 471.0 | 1.19 ± 0.28 |

In Tables 1-5, the $IC_{50}$ or $EC_{50}$ values were determined using the following assay. This assay measures intracellular calcium release via fluorescence as an indication of CXCR2 receptor activation by the physiologic agonist GROα. The assay is a $Ca^{2+}$ mobilization assay that measures changes in intracellular $Ca^{2+}$ with a FlexStation II scanning fluorometer using a FLIPR-3 Calcium Assay Kit (Molecular Devices, Sunnyvale, Calif.). The procedure is as follows:

1. Human neutrophils were suspended in $HBSS^-$ (without $Ca^{2+}$ and $Mg^{2+}$) containing 10 mM HEPES and FLIPR Calcium 3 dye ($3.1\times10^7$ cells in total volume 1.7 mL).
2. Cells were aliquoted (200 μL of the cell suspension per tube, 8 tubes total) and 2 μL of the designated compound (with appropriate dilutions) were added to each of 6 tubes. As controls, 2 μL of DMSO (1% final concentration) were added to other 2 tubes.
3. Cells were incubated for 30 min at 37° C.
4. After dye loading, tubes were centrifuged at 6,000 rpm for 1 min, supernatant was removed and cell pellet was re-suspended in 200 μL of $HBSS^+$ (with $Ca^+$ and $Mg^{2+}$) containing 10 mM HEPES.

5. The compound or DMSO (control) was added again at the same concentrations that were used during cell loading.
6. The cell suspension was aliquoted into a 96-well Reading Plate (Corning) in a volume of 90 μL ($10^5$ cells/well). The Compound Plate contained physiologic agonist (GROα in $HBSS^-$) or $HBSS^-$ (control).
7. After 15 sec of reading the basal level of fluorescence using the FlexStation II instrument, 10 μL of GROα or $HBSS^-$ were automatically transferred from the Compound Plate into the Reading Plate (final concentration of GROα was 25 nM).
8. Changes in fluorescence were monitored ($\lambda_{ex}$=485 nm, $\lambda_{em}$=525 nm) every 5 s for 240 to 500 s at room temperature.
9. The maximum change in fluorescence, expressed in arbitrary units over baseline (Max-Min) was used to determine the GROα response. The effect of each compound on the GROα response was normalized and expressed as a percent of the DMSO control, which was designated as "100% response." Curve fitting and calculation of the compound inhibitory concentration that reduces the level of the GROα response by 50% ($IC_{50}$), or the compound agonist concentration that increases the level of the calcium release by 50% of its maximum induced change ($EC_{50}$) in the absence of GROα were determined by nonlinear regression analysis of the dose-response curves generated using Prism 4 (GraphPad Software, Inc., San Diego, Calif.).

Therapeutic Activity

Modulators of neutrophil activity can have great therapeutic benefit in a number of indications. In disease states characterized by an improperly heightened neutrophil response, an inhibitor of neutrophil activity would be indicated. In patients suffering from, for example neutropenia, a neutrophil agonist or activator has clinical benefit. In vivo evaluation of two lead compounds 1 (SX-517) and 2 (SX-576) in the murine air-pouch model of inflammation, revealed that both inhibitory and agonist activity on neutrophils were achieved, depending on the dose given (see FIGS. 1 and 2).

TABLE 5

| Compound number | structure | $EC_{50}$ (μM) | Magnitude of Agonist Response (% of GROα only Control) |
|---|---|---|---|
| 1 (SX-517) | 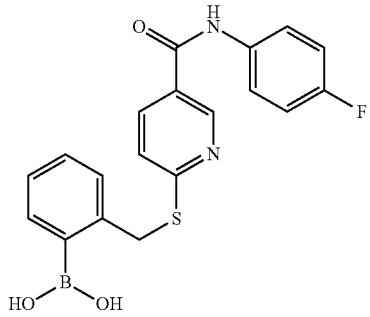 | ND | ND |
| 2 (SX-576) | 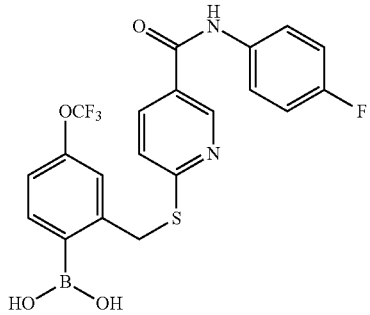 | 1.25 | 100 |
| 13 (SX-578) | 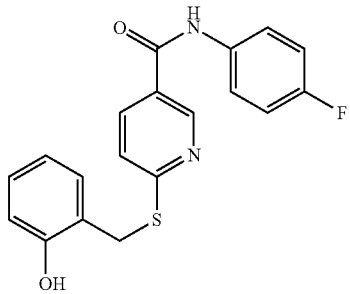 | 2.4 | 60 |

TABLE 5-continued

| Compound number | structure | $EC_{50}$ (μM) | Magnitude of Agonist Response (% of GROα only Control) |
|---|---|---|---|
| 14 (SX-585) | 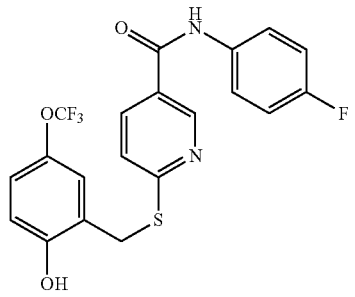 | 1.81 | 15 |

Abbreviation: ND = no agonist activity detected.

Preparation of the Compounds

In the processes described below, functional groups of intermediate compounds may need to be protected by suitable protecting groups. Such functional groups include boronic acids, and mercapto-, hydroxy- and amino-functionalities. Suitable protecting groups, for example, include pinacol, neopentyl glycol, and other diol-based protecting groups for boronic acids; benzyl- or triphenylmethyl- for mercapto- and hydroxyl-functionalities; and tert-butyl-, 9-fluorenylmethyl-, or benzyl-carbamates for amines. Compounds may be prepared from readily available starting materials according to methodology set forth in the synthetic schemes below.

Scheme 1

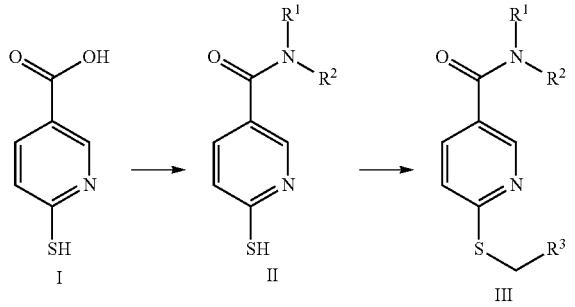

In Scheme 1,6-mercaptonicotinic acid derivative I is coupled to a primary or secondary amine by way of a suitable amide bond forming reagent commonly used in peptide synthesis, such as 2-ethoxy-1-ethoxycarbonyl-1,2-dihydroquinoline (EEDQ). The resulting thiol can then be alkylated with the appropriate alkyl halide using a suitable base.

Scheme 2

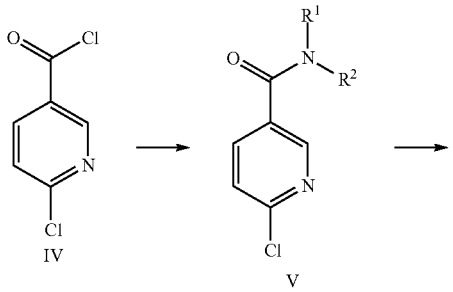

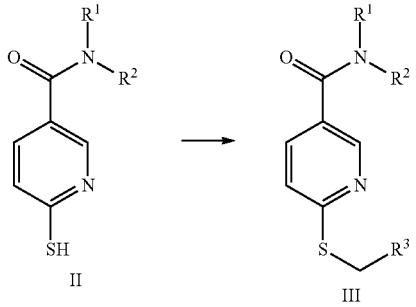

In Scheme 2, an alternative method to prepare thiol-substituted nicotinamide III is presented. In this alternative synthesis, 6-chloronicotinoyl chloride is directly amidated with either a primary or secondary amine to give 6-chloronicotinamide V. The aryl chloride is then displaced with the alkali salt of hydrogen sulfide to yield the thio-substituted nicotinamide. The resulting thiol can then be alkylated with the appropriate alkyl halide using a suitable base.

Scheme 3

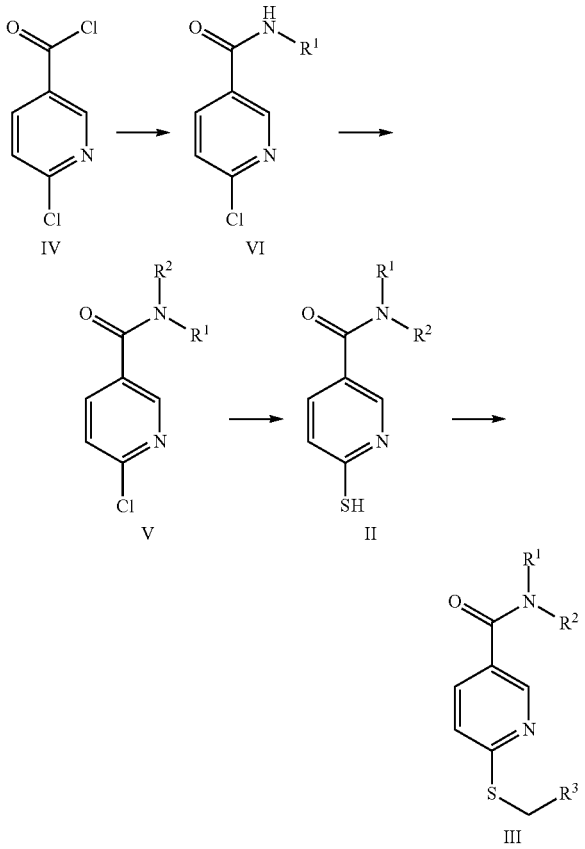

In Scheme 3, an alternative method to prepare N-dialkylated derivatives is presented. In this alternative synthesis, 6-chloronicotinoyl chloride IV is directly amidated with a primary amine to form N-monoalkylated derivative VI. The amide is then deprotonated with either a strong base such as n-butyllithium, or under phase transfer conditions with 50% aq. sodium hydroxide and suitable organic solvent with a suitable phase transfer catalyst. The deprotonated amide is then alkylated with a suitable alkyl halide to form N-dialkylated derivative V. The aryl chloride is then displaced with the alkali salt of hydrogen sulfide to form the thio-nicotinamide derivative II. The resultant thiol can then be alkylated with the appropriate alkyl halide using a suitable base to provide either the substituted thionicotinamide derivative III.

Scheme 4

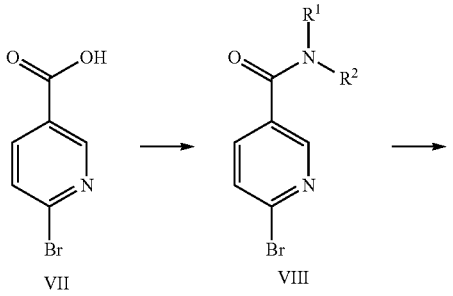

-continued

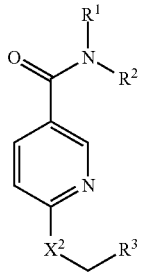

In scheme 4, a method to prepare hydroxyl- and amino-substituted derivatives is presented. In this synthesis, 6-bromonicotinic acid VII coupled to a primary or secondary amine by way of a suitable amide bond forming reagent commonly used in peptide synthesis, such as 2-ethoxy-1-ethoxycarbonyl-1,2-dihydroquinoline (EEDQ). The resulting heteroaryl bromide VIII nucleophilic aromatic substitution with hydroxyl- or amino-substituted synthons using a suitably strong base (i.e., potassium tert-butoxide) or under phase transfer catalytic conditions, to yield the oxygen or nitrogen substituted nicotinamide derivative IX.

Synthetic Methods

Compounds of formula (1) and formula (2) may be produced by processes known to those skilled in the art, in the preceding reaction schemes, and in the preparations and examples below.

General Procedures for the Preparation of S-Substituted N-(4-Fluoro-Phenyl) Nicotinamides:

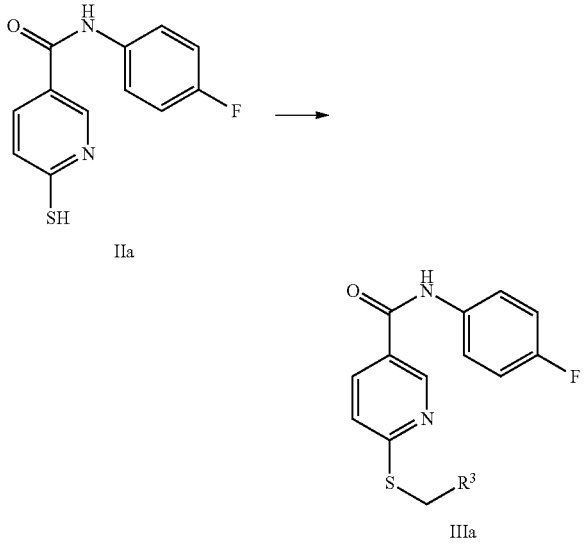

Method A: Thionicotinamide IIa (1 eq.) and corresponding bromomethyl derivative (1 eq.) was suspended in EtOH (5 ml/mmol) in a round bottom flask. To the suspension, 1N NaOH (1 eq.) was added, and the reaction mixture was brought to gentle reflux, and monitored by either TLC or LC-MS until complete (0.5-2 hours). The crude product IIIa is then precipitated out of solution by the addition of water (5-20 ml/mmol). If necessary, further purification may be achieved by using either flash silica gel chromatography or preparative HPLC.

Method B: Thionicotinamide IIa (1 eq.) and corresponding bromomethyl derivative (1 eq.) was dissolved in anhydrous DMF (2 ml/mmol) in a round bottom flask. To the solution, a tertiary amine base (diisopropylethylamine, triethylamine or N-methylmorpholine, 1 eq) was added. The reaction was allowed to proceed at room temperature, and monitored by either TLC or LC-MS until complete (1-18 hours). The crude product IIIa is then precipitated out of solution by the addition of water (5-50 ml/mmol). If necessary, further purification may be achieved using either flash silica gel chromatography or preparative HPLC.

Method C: Thionicotinamide IIa (1 eq.) and N-methylmorpholino-substituted polystyrene resin (5 eq.) was added to a culture tube fitted with a screw cap enclosure. A solution of the appropriate alkyl bromide (2.5 eq.) was added as a solution in anhydrous dimethylformamide (5 ml/mmol) and the culture tube placed in a heat block preheated to 60° C. for 2 hours. Sulfhydryl-bearing scavenger resin (5 eq.) was then added to the reaction mixture, and the culture tube replaced in the heat block at 60° C. for 4 hours. After cooling, the organic reaction solution was filtered then diluted into water (100 ml/mmol) to precipitate the product. The resulting suspension was then centrifuged at 5000 rpm for 15 minutes, the aqueous supernatant was decanted, and the product IIIa dried in a vacuum oven overnight at 50° C. If necessary, further purification may be achieved using either flash silica gel chromatography or preparative HPLC.

Method D, general procedure for the deprotection of aryl boronic esters (from Yuen et al, Tetrahedron Letters 46:7899-7903, 2005): The aryl boronic ester was dissolved in methanol (2 ml/mmol) and aqueous potassium hydrogen fluoride (4.5 M, 5.6 eq.) was then added. The resulting white slurry was stirred at room temperature for 15-30 min, then concentrated in vacuo and dissolved in hot acetone. The mixture was filtered, and the solvent removed by rotary evaporation. The resulting material was then dissolved in acetonitrile (1 ml/mmol) and water (3 eq.), then trimethylsilyl chloride (3 eq.) was added to the reaction mixture. The resulting suspension was stirred for 1 h, then quenched with saturated aqueous sodium hydrogencarbonate and dried over sodium sulfate. The reaction mixture was filtered, and the solvent removed by rotary evaporation. If necessary, further purification may be achieved by preparative HPLC.

Method E, general procedure for the oxidative deboronylation of aryl boronic esters or boronic acids (from Webb, K. S. and Levy, D, Tetrahedron Letters 36:5117-5118, 1995). The boronic acid or boronic ester was suspended in aqueous sodium hydroxide (0.5 M, 2.7 eq.) and dissolved with a minimal amount of tetrahydrofuran and cooled to ~2° C. Then sodium bicarbonate (8 eq.) and acetone (0.001 mL/mmol) were added followed by Oxone® (1 eq., 0.3 M, in 0.4 mM aqueous EDTA). The reaction was then stirred for five minutes and quenched with sodium bisulfite (1 ml/mmol, 5M aqueous). The solvent was removed by reduced pressure rotary evaporation and then dried under vacuum.

Method F, general procedure for the preparation of S-oxidized derivatives. The thionicotinamide derivative was suspended in dichloromethane with m-chloroperbenzoic acid (stoichiometry varies depending on starting material and final desired oxidation state). The reaction suspension was stirred overnight at room temperature, then filtered, and washed with dichloromethane/hexanes (1:1), then dichloromethane. The resulting solid was reconstituted in dimethylformamide and precipitated from water. The resulting solid was filtered, washed with water and dried to yield the desired product Methods of Treatment One embodiment is directed to a pharmaceutical composition comprising at least one compound of formula (1) or formula (2), or a pharmaceutically acceptable salt or solvate thereof, in combination with a pharmaceutically acceptable carrier.

The methods of treatment of this disclosure are advantageous in treating diseases where the ELR-CXC chemokine binds to CXCR2. Another embodiment of the disclosure is directed to a method of treating CXCR2 chemokine mediated diseases in a patient in need of such treatment comprising administering to the patient a therapeutically effective amount of at least one compound of formula (1) or formula (2), or a pharmaceutically acceptable salt or solvate thereof.

Another embodiment of the disclosure is a method of treating CXCR2 chemokine mediated diseases in a patient in need thereof comprises administering to the patient (a) an effective amount of at least one compound of formula (1) or formula (2), or a pharmaceutically acceptable salt or solvate thereof, concurrently or sequentially with (b) at least one additional agent, drug, medicament, antibody and/or inhibitor useful for the treatment of CXCR2 chemokine mediated diseases. Examples of the additional medicament, drug or agent include, but are not limited to, disease modifying antirheumatic drugs; nonsteroidal antiinflammatory drugs (NSAIDs); COX-2 selective inhibitors; COX-1 inhibitors; immunosuppressives; steroids; biological response modifiers; and other anti-inflammatory agents or therapeutics useful for the treatment of CXCR2 chemokine mediated diseases.

Another embodiment of the method of treating a CXCR2 chemokine mediated disease is administering (a) a therapeutically effective amount of at least one compound of formula (1) or formula (2), or a pharmaceutically acceptable salt or solvate thereof, concurrently or sequentially with (b) at least one medicament selected from the group consisting of: disease modifying antirheumatic drugs; nonsteroidal anti-inflammatory drugs; COX-2 selective inhibitors; COX-1 inhibitors; immunosuppressives; steroids; biological response modifiers; and other anti-inflammatory agents or therapeutics useful for the treatment of CXCR1 and/or CXCR2 chemokine mediated diseases.

Another embodiment of this disclosure is a method for treating cancer in a patient in need of such treatment, the method comprises administering to said patient a therapeutically effective amount of a compound of formula (1) or formula (2), or a pharmaceutically acceptable salt or solvate thereof. Another embodiment of this disclosure is a method for treating cancer comprising administering to the patient a therapeutic amount of at least one compound of formula (1) or formula (2), or a pharmaceutically acceptable salt or solvate thereof, concurrently or sequentially with (a) at least one antineoplastic agent selected from the group consisting of: (1) gemcitabine, (2) paclitaxel, (3) 5-Fluorouracil (5-FU), (4) cyclo-phosphamide, (5) temozolomide and (6) Vincristine or (b) at least one agent selected from the group consisting of (1) microtubule affecting agents, (2) antineoplastic agents, (3) anti-angiogenesis agents, (4) VEGF receptor kinase inhibitors, (5) antibodies against the VEGF receptor, (6) interferon, and (7) radiation.

Another embodiment of this disclosure is a method for treating asthma in a patient in need of such treatment the method comprising administering to the patient a therapeutically effective amount of at least one compound of formula (1) or formula (2), or a pharmaceutically acceptable salt or solvate thereof. Another embodiment of this disclosure is a method for treating a pulmonary disease (e.g., COPD, asthma, or cystic fibrosis), in a patient in need of such treatment, the method comprising administering to the patient a therapeutically effective amount of: (a) at least one compound of formula (1) or formula (2), or a pharmaceutically acceptable salt or solvate thereof, concurrently or sequentially with (b) at least one compound selected from the group consisting of: glucocorticoids, 5-lipoxygenase inhibitors, beta-2 adrenoceptor agonists, muscarinic M1 antagonists, muscarinic M3 antagonists, muscarinic M2 agonists, NK3 antagonists, LTB4 antagonists, cysteinyl leukotriene antagonists, bronchodilators, PDE4 inhibitors, PDE inhibitors, elastase inhibitors, MMP inhibitors, phospholipase A2 inhibitors, phospholipase D inhibitors, histamine H1 antagonists, histamine H3 antagonists, dopamine agonists, adenosine A2 agonists, NK1 and NK2 antagonists, GABA-β agonists, nociceptin agonists, expectorants, mucolytic agents, decongestants, antioxidants, anti-IL-8 antibodies, anti-IL-5 antibodies, anti-IgE antibodies, anti-TNF antibodies, IL-10, adhesion molecule inhibitors, and growth hormones.

Another embodiment of this disclosure is a method for treating multiple sclerosis, comprising administering to the patient: (a) a therapeutically effective amount of at least one compound of formula (1) or formula (2), or a pharmaceutically acceptable salt or solvate thereof, concurrently or sequentially with (b) a therapeutically effective amount of at least one compound selected from the group consisting of: glatiramer acetate, glucocorticoids, methotrexate, azothioprine, mitoxantrone, and CB2-selective inhibitors.

Another embodiment of this disclosure is a method of treating multiple sclerosis comprising concurrent or sequential administration of a therapeutically effective amount of: (a) at least one compound of formula (1) or formula (2), or a pharmaceutically acceptable salt or solvate thereof, and (b) at least one compound selected from the group consisting of: methotrexate, cyclosporin, leflunimide, sulfasalazine, β-methasone, β-interferon, glatiramer acetate, prednisone, etonercept, and infliximab.

Another embodiment of this disclosure is a method for treating rheumatoid arthritis in a patient in need of such treatment comprising administering to said patient a therapeutically effective amount of at least one compound of formula 1, or a pharmaceutically acceptable salt or solvate thereof.

Another embodiment of this disclosure is a method for treating rheumatoid arthritis in a patient in need of such treatment comprising administering to said patient a therapeutically effective amount of at least one compound of formula (1) or formula (2), or a pharmaceutically acceptable salt or solvate thereof, in combination with at least one compound selected from the group consisting of COX-2 inhibitors, COX-1 inhibitors, immunosuppressives (e.g., methotrexate, aminopterin, cyclosporin, leflunimide and sulfasalazine), steroids (e.g., betamethasone, cortisone and dexamethasone), PDE 4 inhibitors, anti-TNF-α compounds, MMP inhibitors, glucocorticoids, chemokine inhibitors, CB2-selective agents, and other classes of compounds indicated for the treatment of rheumatoid arthritis.

Another embodiment of this disclosure is a method for treating stroke and ischemia reperfusion injury in a patient in need of such treatment the method comprising administering to the patient a therapeutically effective amount of: (a) at least one compound of formula (1) or formula (2), or a pharmaceutically acceptable salt or solvate thereof, concurrently or sequentially with (b) at least one compound selected from the group consisting of: thrombolitics (e.g., tenecteplase, TPA, alteplase), antiplatelet agents (e.g., gpIIb/IIIa), antagonists (e.g., abciximab and eftiifbatide), anticoagulants (e.g., heparin), and other compounds indicated for the treatment of rheumatoid arthritis.

Another embodiment of this disclosure is a method for treating stroke and ischemia reperfusion injury in a patient in need of such treatment the method comprising administering to the patient a therapeutically effective amount of: (a) at least one compound of formula (1) or formula (2), or a pharmaceutically acceptable salt or solvate thereof concurrently or sequentially with (b) at least one compound selected from the group consisting of: tenecteplase, TPA, alteplase, abciximab, eftiifbatide, and heparin.

Another embodiment of this disclosure is a method for treating psoriasis in a patient in need of such treatment, the method comprising administering to the patient a therapeutically effective amount of: a) at least one compound of formula (1) or formula (2), or a pharmaceutically acceptable salt or solvate thereof, concurrently or sequentially with (b) at least one compound selected from the group consisting of: immunosuppressives (e.g., methotrexate, aminopterin, cyclosporin, efalizumab, alefacept, leflunimide and sulfasalazine), steroids (e.g., β-methasone) and anti-TNFα compounds (e.g., etonercept and infliximab).

This disclosure also provides a method for treating CXCR2 mediated disease or condition selected from the group consisting of: pain (e.g., acute pain, acute inflammatory pain, chronic inflammatory pain, and neuropathic pain), acute inflammation, chronic inflammation, rheumatoid arthritis, psoriasis, atopic dermatitis, asthma, bronchopulmonary dysplasia, COPD, adult respiratory disease, arthritis, inflammatory bowel disease, Crohn's disease, ulcerative colitis, septic shock, endotoxic shock, gram negative sepsis, toxic shock syndrome, stroke, ischemia reperfusion injury, renal reperfusion injury, glomerulonephritis, thrombosis, Alzheimer's disease, graft vs. host reaction (i.e., graft-versus-host disease), allograft rejections (e.g., acute allograft rejection, and chronic allograft rejection), malaria, acute respiratory distress syndrome, delayed type hypersensitivity reaction, atherosclerosis, cerebral ischemia, cardiac ischemia, osteoarthritis, multiple sclerosis, restinosis, angiogenesis, angiogenesis associated with tumor growth, osteoporosis, gingivitis, respiratory viruses, herpes viruses, hepatitis viruses, HIV, Kaposi's sarcoma associated virus (i.e., Kaposi's sarcoma), meningitis, cystic fibrosis, pre-term labor, cough, pruritis, multi-organ dysfunction, trauma, strains, sprains, contusions, psoriatic arthritis, herpes, encephalitis, CNS vasculitis, traumatic brain injury, systemic tumors, CNS tumors, tumors dependent on angiogenesis for growth, leukopenia and neutropenia, chemotherapy-induced leukopenia and neutropenia, opportunistic infections associated with neutropenia or leukopenia, subarachnoid hemorrhage, post surgical trauma, interstitial pneumonitis, hypersensitivity, crystal induced arthritis, acute pancreatitis, chronic pancreatitis, acute alcoholic hepatitis, necrotizing enterocolitis, chronic sinusitis, angiogenic ocular disease, ocular inflammation, retinopathy of prematurity, diabetic retinopathy, macular degeneration with the wet type preferred, corneal neovascularization, polymyositis, vasculitis, acne, gastric ulcers, duodenal ulcers, celiac disease, esophagitis, glossitis, airflow obstruction, airway hyperresponsiveness (i.e., airway hyperreactivity), bronchiectasis, bronchiolitis, bronchiolitis obliterans, chronic bronchitis, cor pulmonae, dyspnea, emphysema, hypercapnea, hyperinflation, hypoxemia, hyperoxia-induced inflammations, hypoxia, surgical lung volume reduction, pulmonary fibrosis, pulmonary hypertension, right ventricular hypertrophy, peritonitis associated with continuous ambulatory peritoneal dialysis (CAPD), granulocytic ehrlichiosis, sarcoidosis, small airway disease, ventilation-perfusion mismatching, wheeze, colds, gout, alcoholic liver disease, lupus, burn therapy (i.e., the treatment of burns), periodontitis, cancer, transplant reperfusion injury, early transplantation rejection (e.g., acute allograft rejection) in a patient in need of such treatment comprising administering to said patient an effective amount of at least one compound of formula (1) or formula (2), or a pharmaceutically acceptable salt or solvate thereof.

Another embodiment of this disclosure is a method for treating diseases such as allograft rejections, early transplantation rejections, autoimmune deafness, myocarditis, neuropathies, autoimmune diseases and vasculitis syndromes wherein said:

(a) allograft rejections are selected from the group consisting of acute allograft rejections and chronic allograft rejections;

(b) early transplantation rejection is an acute allograft rejection;

(c) autoimmune deafness is Meniere's disease;

(d) myocarditis is viral myocarditis;

(e) neuropathies are selected from the group consisting of IgA neuropathy, membranous neuropathy and idiopathic neuropathy;

(f) autoimmune diseases are anemias; and (g) vasculitis syndromes are selected from the group consisting of giant cell arteries, Behcet's disease and Wegener's granulomatosis.

Another embodiment of this disclosure is a method for treating COPD in a patient in need of such treatment comprising administering to said patient a therapeutically effective amount of at least one (usually one) compound of formula (1) or formula (2), or a pharmaceutically acceptable salt or solvate thereof.

Another embodiment of this disclosure is a method for treating arthritis in a patient in need of such treatment comprising administering to said patient a therapeutically effective amount of at least one compound of formula (1) or formula (2), or a pharmaceutically acceptable salt or solvate thereof.

Another embodiment of this disclosure is a method for treating osteoarthritis in a patient in need of such treatment comprising administering to said patient a therapeutically effective amount of at least one compound of formula (1) or formula (2), or a pharmaceutically acceptable salt or solvate thereof.

Another embodiment of this disclosure is a method for treating pain in a patient in need of such treatment comprising administering to said patient a therapeutically effective amount of at least one compound of formula (1) or formula (2), or a pharmaceutically acceptable salt or solvate thereof.

Another embodiment of this disclosure is a method for treating pain in a patient in need of such treatment comprising administering to said patient a therapeutically effective amount of at least one compound of formula (1) or formula (2), or a pharmaceutically acceptable salt or solvate thereof, and administering a therapeutically effective amount of at least one medicament selected from the group consisting of: NSAIDs, COXIB inhibitors (e.g., COX-1 and COX-2 inhibitors), anti-depressants, and anti-convulsants.

Another embodiment of this disclosure is a method for treating acute pain in a patient in need of such treatment comprising administering to said patient a therapeutically effective amount of at least one (usually one) compound of formula (1) or formula (2), or a pharmaceutically acceptable salt or solvate thereof.

Another embodiment of this disclosure is a method for treating acute inflammatory pain in a patient in need of such treatment comprising administering to said patient a therapeutically effective amount of at least one compound of formula (1) or formula (2), or a pharmaceutically acceptable salt or solvate thereof.

Another embodiment of this disclosure is a method for treating chronic inflammatory pain in a patient in need of such treatment comprising administering to said-patient a therapeutically effective amount of at least one compound of formula (1) or formula (2), or a pharmaceutically acceptable salt or solvate thereof.

Another embodiment of this disclosure is a method for treating neuropathic pain in a patient in need of such treatment comprising administering to said patient a therapeutically effective amount of at least one compound of formula (1) or formula (2), or a pharmaceutically acceptable salt or solvate thereof.

Another embodiment of this disclosure is a pharmaceutical composition comprising at least one compound of formula (1) or formula (2), or a pharmaceutically acceptable salt or solvate thereof, and at least one other agent, medicament, antibody and/or inhibitor disclosed above, and a pharmaceutically acceptable carrier.

In general the compounds used to treat pain will have CXCR2 antagonistic activity.

NSAIDs are well known to those skilled in the art and can be used in their known dosages and dosage regimens. Examples of NSAIDs include but are not limited to: piroxicam, ketoprofen, naproxen, indomethacin, and ibuprofen COXIB inhibitors are well known to those skilled in the art and can be used in their known dosages and dosage regimens. Examples of COMB inhibitors include, but are not limited to: rofecoxib and celecoxib. Anti-depressants are well known to those skilled in the art and can be used in their known dosages and dosage regimens. Examples of anti-depressants include but are not limited to: amitriptyline and nortriptyline. Anti-convulsants are well known to those skilled in the art and can be used in their known dosages and dosage regimens. Examples of anti-convulsants include but are not limited to: gabapentin, carbamazepine, pregabalin, and lamotragine.

Pharmaceutical Compositions

For preparing pharmaceutical compositions from the compounds described by this disclosure, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington: The Science and Practice of Pharmacy, 20th Edition, (2000), Lippincott Williams & Wilkins, Baltimore, Md. which is incorporated herein by reference.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration. Liquid form preparations may also include dissolution in lipid-based, self-emulsifying drug delivery systems (SEDDS) such as Labrasol® or Gelucire® for oral administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compounds of this disclosure may also be deliverable transdermally. The transdermal composition can take the form of creams, lotions, aerosols and/or emulsions and can be included in a transdermal patch of the matrix or reservoir type as are conventional in the art for this purpose.

The compound can be administered orally.

A suitable pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 0.01 mg to about 1000 mg, or from about 0.01 mg to about 750 mg, or from about 0.01 mg to about 500 mg, or from about 0.01 mg to about 250 mg, according to the particular application.

The actual dosage employed may be varied depending upon the requirements of the patient and the severity of the condition being treated. Determination of the proper dosage regimen for a particular situation is within the skill of the art. For convenience, the total dosage may be divided and administered in portions during the day as required.

The amount and frequency of administration of the compounds of this disclosure and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 0.04 mg/day to about 4000 mg/day, in two to four divided doses.

The amount and frequency of administration of the compounds of either formula (1) or formula (2) and the chemotherapeutic agents and/or radiation therapy will be regulated according to the judgment of the attending clinician (physician) considering such factors as age, condition and size of the patient as well as severity of the disease being treated. A dosage regimen of the compound of either formula (1) or formula (2) can be oral administration of from 10 mg to 2000 mg/day, or 10 to 1000 mg/day, or 50 to 600 mg/day, in two to four (or two) divided doses, to block tumor growth. Intermittent therapy (e.g., one week out of three weeks or three out of four weeks) may also be used.

The chemotherapeutic agent and/or radiation therapy can be administered according to therapeutic protocols well known in the art. It will be apparent to those skilled in the art that the administration of the chemotherapeutic agent and/or radiation therapy can be varied depending on the disease being treated and the known effects of the chemotherapeutic agent and/or radiation therapy on that disease. Also, in accordance with the knowledge of the skilled clinician, the therapeutic protocols (e.g., dosage amounts and times of administration) can be varied in view of the observed effects of the administered therapeutic agents (i.e., antineoplastic agent or radiation) on the patient, and in view of the observed responses of the disease to the administered therapeutic agents.

If the compound of either formula (1) or formula (2), and the chemotherapeutic agent and/or radiation is not administered simultaneously or essentially simultaneously, then the initial order of administration of the compound of either formula (1) or formula (2), and the chemotherapeutic agent and/or radiation, may not be important. Thus, the compound of either formula (1) or formula (2) may be administered first, followed by the administration of the chemotherapeutic agent and/or radiation; or the chemotherapeutic agent and/or radiation may be administered first, followed by the administration of the compound of either formula (1) or formula (2). This alternate administration may be repeated during a single treatment protocol. The determination of the order of administration, and the number of repetitions of administration of each therapeutic agent during a treatment protocol, is well within the knowledge of the skilled physician after evaluation of the disease being treated and the condition of the patient.

For example, the chemotherapeutic agent and/or radiation may be administered first, especially if it is a cytotoxic agent, and then the treatment continued with the administration of the compound of either formula (1) or formula (2) followed, where determined advantageous, by the administration of the chemotherapeutic agent and/or radiation, and so on until the treatment protocol is complete.

The particular choice of a compound from either formula (1) or formula (2), and chemotherapeutic agent and/or radiation will depend upon the diagnosis of the attending physicians and their judgment of the condition of the patient and the appropriate treatment protocol.

Also, in general, the compound of either formula (1) or formula (2) and the chemotherapeutic agent do not have to be administered in the same pharmaceutical composition, and may, because of different physical and chemical characteristics, have to be administered by different routes. For example, the compound of either formula (1) or formula (2) may be administered orally to generate and maintain good blood levels thereof, while the chemotherapeutic agent may be administered intravenously. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

Thus, in accordance with experience and knowledge, the practicing physician can modify each protocol for the administration of a component (therapeutic agent; i.e., the compound from either formula (1) or formula (2), chemotherapeutic agent or radiation) of the treatment according to the individual patient's needs, as the treatment proceeds.

The attending clinician, in judging whether treatment is effective at the dosage administered, will consider the general well-being of the patient as well as more definite signs such as relief of disease-related symptoms, inhibition of tumor growth, actual shrinkage of the tumor, or inhibition of metastasis. Size of the tumor can be measured by standard methods such as radiological studies, e.g., CAT or MRI scan, and successive measurements can be used to judge whether or not growth of the tumor has been retarded or even reversed. Relief of disease-related symptoms such as pain, and improvement in overall condition can also be used to help judge effectiveness of treatment.

The disclosure provided herein is exemplified by the following preparations and examples that should not be construed to limit the scope of the disclosure. Alternative mechanistic pathways and analogous structures may be apparent to those skilled in the art.

SYNTHESIS EXAMPLE 1

Synthesis of
N-(4-fluoro-phenyl)-6-mercapto-nicotinamide IIa

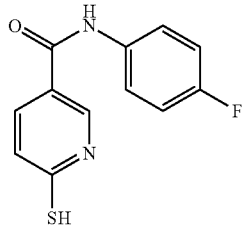

To a round bottom flask, 6-mercapto-nicotinic acid (50 mmol, 7.76 g) was added and stirred in dimethylformamide (150 mL). To the stirring reaction mixture 4-fluoroaniline (50 mmol, 4.8 mL) was added followed by the addition of 2-ethoxy-1-ethoxycarbonyl-1,2-dihydroquinoline (EEDQ, 50 mmol, 12.36 g). The dark brown mixture was stirred for 12 hours. The mixture was then diluted with water (500 mL) and the precipitate collected by filtration and washed repeatedly with water. The off-white solid was dried in an oven (50° C.) for 72 hours to afford 6.42 g (52%) of the thionicotinamide product: ESI-MS m/z=248.9 $[M+H]^+$; $^1H$ NMR (300 MHz, d6-DMSO) δ 10.2 (s, 1H), 8.28 (m, 1H), 7.83 (m, 1H), 7.68 (m, 2H), 7.33 (m, 1H), 7.15 (m, 2H); TLC (EtOAc/hexanes/MeOH 1:1:0.1) $R_f$ 0.7)

SYNTHESIS EXAMPLE2

Synthesis of Compound 1 (SX-517)

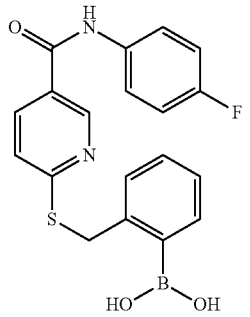

As described in Method A, N-(4-fluoro-phenyl)-6-mercapto-nicotinamide IIa (1.27 g, 5.10 mmol) and 2-bromomethyl-phenylboronic acid (1.09 g, 5.10 mmol) were suspended in ethanol (50 ml). To the suspension, 1 N sodium hydroxide (5.1 ml, 5.10 mmol) was added, and the reaction mixture heated to gentle reflux for 2 hours, then water (50 ml) was added to the reaction mixture while still hot. Upon cooling, a white precipitate formed, and this was filtered, washed with 50% aqueous ethanol, then water and dried in the oven to yield 1.53 g (78%) of 6-(2-borono-2-yl-benzylsulfanyl)-N-(4-fluoro-phenyl)-nicotinamide as an off-white solid. ESI-MS m/z=383.1 $[M+H]^+$; 1H NMR (300 MHz, d4-MeOH) δ 7.48 (s, 1H), 6.55 (dd, 1H), 6.15 (q, 2H), 5.92, (d, 1H), 5.85 (d, 1H), 5.7 (m, 3H), 5.56 (t, 2H); Calcd. for $C_{19}H_{16}BFN_2O_3S$: C, 59.71; H, 4.22; N, 7.33; S, 8.39. Found: C, 59.54; H, 4.38; N, 7.48; S, 8.49.

SYNTHESIS EXAMPLE 3

Synthesis of Compound 19

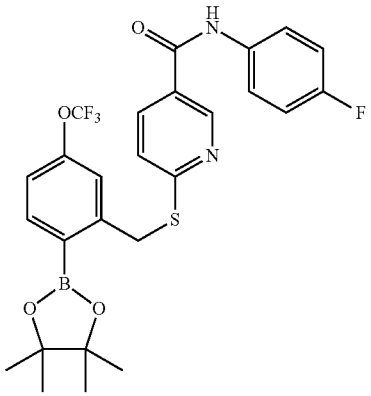

As described in Method B, N-(4-fluoro-phenyl)-6-mercapto-nicotinamide IIa (372 mg, 1.5 mmol) and 2-bromomethyl-5-trifluoromethoxy-phenylboronic acid (572 mg, 1.5 mmol) were suspended in DMF (15 ml). To the reaction flask DIPEA (261 μL, 1.5 mmol) was added and the reaction was stirred for 30 minutes. Reaction completion was monitored by LC-MS. Cold water (100 mL) was added and the precipitate was collected by filtration and washed several times with cold water to afford 724.8 mg (88% yield, >90% purity by LC-MS) of the off-white solid product, 6-(2-boronic pinacol ester-5-trifluoromethoxy-benzylsulfanyl)-N-(4-fluoro-phenyl)-nicotinamide. ESI-MS m/z=549.1 $[M+H^+]$.

SYNTHESIS EXAMPLE 4

Synthesis of Compound 2 (SX-576)

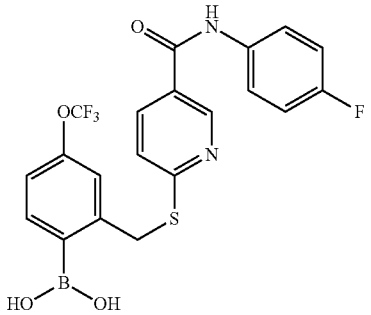

Compound 2 was obtained from compound 19 by deprotection of the boronic acid pinacol ester using Method D (modified from Yuen et al, Tetrahedron Letters 46:7899-

7903). Compound 15 (450 mg, 0.8 mmol, 1 eq.) was dissolved in methanol (20 mL). The reaction vessel was charged with 4.5 M aqueous potassium hydrogen fluoride (5 eq.) and the resulting white slurry was stirred for 1 hour. The methanol was reduced by rotary evaporation at room temperature and the resulting mixture was diluted with cold water (100 mL) and placed in the refrigerator. The resulting white precipitate was collected by filtration to afford 328.2 mg (87.5% yield, >90% purity by LC-MS) of 6-(2-boronic acid-5-trifluoromethoxy-benzylsulfanyl)-N-(4-fluoro-phenyl)-nicotinamide. ESI-MS m/z=467.2 $[M+H]^+$. 1H NMR (300 MHz, d4-MeOH) d 9.0 (s, 1H), 8.1 (dd, 2H), 7.86 (s, 1H), 7.7 (q, 2H), 7.6 (d, 1H), 7.4 (d, 1H), 7.3 (d, 1H), 7.1 (t, 2H), 4.5 (s, 2H).

Calcd. for $C_{20}H_{15}BF_4N_2O_4S$: C, 51.52; H, 3.24; N, 6.01; S, 6.88; F, 16.3. Found: C, 51.27; H, 3.33; N, 5.95; S, 6.67; F, 16.45.

SYNTHESIS EXAMPLE 5

Synthesis of Compound 14 (SX-585)

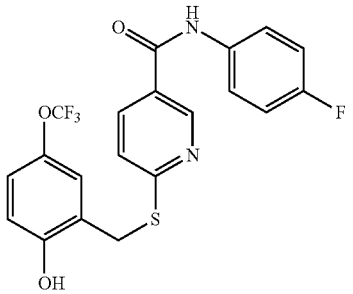

Compound 14 was obtained from compound 19 by Method E (from Webb, K. S. and Levy, D, Tetrahedron Letters 36:5117-5118, 1995). Compound 19 was suspended in a solution of sodium hydroxide (150 μL, 0.5 M aqueous, 2.7 eq.) and dissolved with a minimal amount of tetrahydrofuran. The mixture was cooled to ~2° C. followed by the addition sodium bicarbonate (0.42 mmol, 8 eq.) and acetone (50 μL). The reaction vessel was then charged with Oxone® (1 eq., 0.055 mmol in 180 μL aqueous 0.4 mM EDTA). The reaction was stirred at ~2° C. for five minutes and quenched with sodium bisulfate (1 ml/mmol, 5M aqueous). Solvent was reduced by rotary evaporation and dried in vacuo to afford 25 mg (83% yield, >90% purity by LC-MS) yellow 6-(2-hydroxy-5-trifluoromethoxy-benzylsulfanyl)-N-(4-fluoro-phenyl)-nicotinamide. ESI-MS m/z=439.4 $[M+H]^+$.

SYNTHESIS EXAMPLE 6

Synthesis of S-(2-bromo-5-methoxy)benzyl nicotinamide Intermediate VII

As described in Method A, N-(4-fluoro-phenyl)-6-mercapto-nicotinamide IIa (745 mg, 3 mmol, 1 eq.) and 2-bromomethyl-4-methoxyphenyl bromide (0.84 g, 3 mmol, 1 eq.) were suspended in ethanol (36 ml). To the suspension, 1 N sodium hydroxide (5.1 ml, 6 mmol, 2 eq.) was added, and the reaction mixture heated to gentle reflux for 2 hours, then water (200 ml) was added to the reaction mixture while still hot. Upon cooling, a white precipitate formed, and this was filtered, washed with 50% aqueous ethanol, then water and dried in the oven to afford 1.33 g (99% yield, >95% purity by LC-MS) of 6-(2-bromo-5-methoxy-benzylsulfanyl)-N-(4-fluoro-phenyl)-nicotinamide, intermediate VII, as an off-white solid. ESI-MS m/z=448.9 $[M+H]^+$.

SYNTHESIS EXAMPLE 7

Synthesis of Compound 4

The bromide was then converted to the boronic ester using borylation chemistry (from Billingsley, K. L. and Buchwald, S. L. Journal of Organic Chemistry 73:5589-5591, 2008): In a dry pressure tube 6-(2-bromo-5-methoxy-benzylsulfanyl)-N-(4-fluoro-phenyl)-nicotinamide VII (895 mg, 2 mmol, 1 eq.), $PdCl_2(CH_3CN)_2$ (0.08 mmol, 4 mol %) and SPhos (0.32 mmol, 16 mol %) were combined, the tube sealed, degassed and back-filled with argon (×2). Anhydrous 1,4-dioxane (2 mL) was added by syringe followed by addition of triethylamine (6 mmol, 6 eq.) and then pinacol borane (3 mmol, 3 eq.). The septum was replaced by a Teflon screw-cap and the pressure tube was heated to 110° C. and the reaction stirred for 24 hours. The reaction progress was monitored by LC-MS. Upon complete consumption of starting material the mixture was cooled and filtered through a thin pad of celite, the celite rinsed with ethyl acetate several times. The final mixture was purified by preparative HPLC to afford 9.2 mg (>99% purity by HPLC) of 6-(2-boronic pinacol ester-5-methoxy-benzylsulfanyl)-N-(4-fluoro-phenyl)-nicotinamide. The boronic ester deprotection was achieved using Method D (modified from Yuen et al, Tetrahedron Letters 46:7899-7903). The boronic ester (9.2 mg, 8 μmol) was dissolved in methanol (1 mL). The reaction vessel was charged with 4.5 M aqueous potassium hydrogen fluoride (5 eq.) and the resulting white slurry was stirred for 1 hour. The methanol was reduced by rotary evaporation at room temperature and the resulting mixture was diluted with cold water (10 mL) and placed in the refrigerator. The resulting white precipitate was collected by filtration to afford 6 mg (65% yield, >90% purity by LC-MS) of Compound 4,6-(2-boronic acid-5-methoxy-benzylsulfanyl)-N-(4-fluoro-phenyl)-nicotinamide. ESI-MS m/z=413.1 $[M+H]^+$.

SYNTHESIS EXAMPLE 8

Synthesis of 6-bromo-3,4-dimethoxy-benzyl chloride Intermediate VIII

To a stirred solution of 6-bromoveratrumaldehyde (3 mmol, 1 eq.) in ethanol (10 mL) sodium borohydride (1 mmol, 4 eq.) was slowly added. The reaction was stirred for 2 hours and then the solvent was removed by rotary evaporation. The resulting white solid was treated with saturated ammonium chloride (15 mL). The aqueous was then extracted with chloroform, dried over magnesium sulfate, then removed by rotary evaporation to afford the alcohol (2.6 mmol, 87% yield). The alcohol (2 mmol, 1 eq.) was then stirred with pyridine (40 μL) in anhydrous chloroform (10 mL) to 0° C. Thionyl chloride (4 mmol, 2 eq.) was then added drop wise and the reaction was stirred at room temperature for 3 hours. The reaction progress was monitored by TLC. After complete consumption of starting material the reaction was poured into water (10 mL) and extracted with chloroform (1×20 mL). The organic layer was washed with $H_2O$ (2×10 brine (1×10 mL), dried over magnesium sulfate, filtered and evaporated to afford the benzyl chloride intermediate VIII (598 mg, 2 mmol, 100% yield). TLC (EtOAc/hexanes, 1:1) $R_f$=0.73; ESI-MS m/z=230.9 $[M-Cl]^+$.

SYNTHESIS EXAMPLE 9

Synthesis of S-(2-bromo-4,5-dimethoxy)benzyl nicotinamide Intermediate IX

Thionicotinamide IIa (prepared as described in Synthesis Example 1, 2 mmol, 1 eq.) was suspended in ethanol (20 mL). The mixture was heated to 80° C. 1N and sodium hydroxide (4 mL) was then added followed by the benzyl chloride intermediate VIII (1.7 mmol, 1 eq.). The mixture was stirred at 80° C., monitored for consumption of thiol by TLC and then diluted with $H_2O$. The precipitate was collected by filtration and dried to afford 0.91 g (75%) of the dimethoxy nicotinamide intermediate IX as a white solid. TLC (EtOAc/hexanes, 1:1) Rf=0.69; ESI-MS m/z=478.9 $[M+H]^+$.

SYNTHESIS EXAMPLE 10

Synthesis of Compound 5

The aryl bromide intermediate IX was combined with $PdCl_2(CH_3CN)_2$ (4 mol %), and XPhos (16 mol %) in a dry pressure tube, sealed, evacuated and backfilled with argon (×2). Anhydrous 1,4-dioxane (2 mL) was then added, followed by triethylamine (6 mmol, 3 eq.) and pinacol borane (3 mmol, 1.5 eq.). The septum was replaced by a Teflon screw cap and the mixture was stirred at 110° C. for 24 hours. The reaction mixture was filtered through a thin pad of celite and eluted with acetonitrile. The organic solvent was concentrated in vacuo and diluted in water, the resulting precipitate was collected by filtration, LC-MS analysis revealed >90% starting material, 5% debrominated, <5% product. The crude mixture was then taken forward to the deprotection step by stirring the crude material in methanol (1 mL) followed by the addition of 4.5 M potassium hydrogen fluoride, monitoring the reaction by LC-MS. The methanol was removed by rotary evaporation and the solution diluted with hot acetone, filtered, and the solvent removed by rotovap. The final product was purified by preparative HPLC to afford 1.2 mg (2%) of the 6-(2-boronic acid-4,5-di-methoxy-benzylsulfanyl)-N-(4-fluoro-phenyl)-nicotinamide, compound 5. ESI-MS m/z=443.1 $[M+H]^+$.

SYNTHESIS EXAMPLE 11

Synthesis of Compound 22

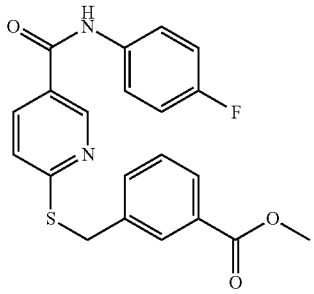

Methyl-3-methyl benzoate (1.5 g, 10 mmol) and N-bromosuccinimide (5.34 g, 30 mmol) was suspended in cyclohexane (50 ml). To the suspension, a catalytic amount of hydrogen peroxide was added, and the reaction mixture was heated to reflux for 16 h. The reaction mixture was then filtered, and evaporated to yield 0.231 g (10%) as a yellow oil. Compound 21 was then formed by coupling methyl 3-bromomethylbenzoate to thionicotinamide intermediate IIa in the manner of Method A to yield 180 mg (45%) of compound 22 as a crystalline material. ESI-MS m/z=397.1 $[M+H]^+$.

SYNTHESIS EXAMPLE 12

Synthesis of Compound 25

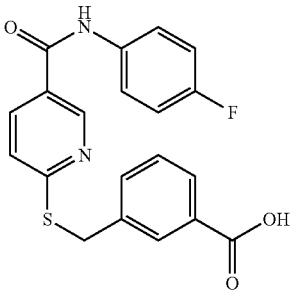

The thionicotinamide methyl ester 21 (100 mg, 0.25 mmol) was saponified using 1N NaOH (1.1 eq.) in MeOH at r.t. for 1 h. The reaction mixture was acidified using 1 N HCl, and extracted into EtOAc. The organic layer was washed with saturated NaCl, dried over $Na_2SO_4$, filtered and evaporated to yield 81 mg (83%) of compound 25 as a white solid. ESI-MS m/z=382.9 $[M+H]^+$.

SYNTHESIS EXAMPLE 13

Synthesis of Compound 26

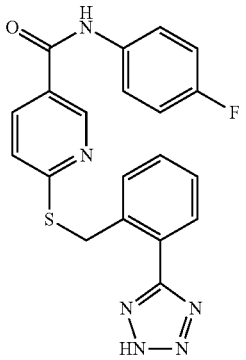

The S-(2-cyanobenzyl)nicotinamide intermediate was prepared via Method B using thionicotinamide IIa and 2-(bromomethyl)-benzonitrile. The cyanobenzyl intermediate (363 mg, 1 mmol) was suspended in anhydrous toluene (25 ml). Dibutyl tin oxide (25 mg, 0.1 mmol) was added, followed by trimethylsilyl azide (131 μl, 1 mmol). The reaction mixture was then heated to reflux for 18 h. The dark yellow brown solution was allowed to cool to room temperature, at which time a brown precipitate was seen to form. The precipitate was filtered and washed with toluene to yield 190 mg (47%) of compound 22. ESI-MS m/z=407.2 $[M+H]^+$.

SYNTHESIS EXAMPLE 14

Synthesis of Compound 49

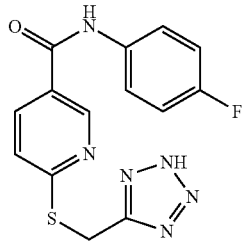

Thionicotinamide IIa (248 mg. 1.00 mmol) was dissolved in anhydrous dimethylformamide (3 ml). Chloroacetonitrile (63 μl, 1.0 mmol) was then added, followed by triethylamine (140 μl, 1.00 mmol). After 4 hours, the organic reaction solution was diluted into water (60 mL), and the resulting precipitate was filtered and washed with water to yield the product as a white solid (259 mg, 90%). The cyano-intermediate (190 mg, 0.66 mmol) and dibutyltin oxide (33 mg, 0.14 mmol) was suspended in toluene (50 mL) and refluxed for 24 hours. The reaction mixture was allowed to cool to room temperature, and the resulting precipitate was filtered and washed with toluene to yield 160 mg (73%) of compound 49 as a light yellow solid. TLC (1% AcOH/EtOAc): $R_f$=0.32. ESI-MS m/z=331.3 $[M+H]^+$.

SYNTHESIS EXAMPLE 15

Synthesis of Compound 104

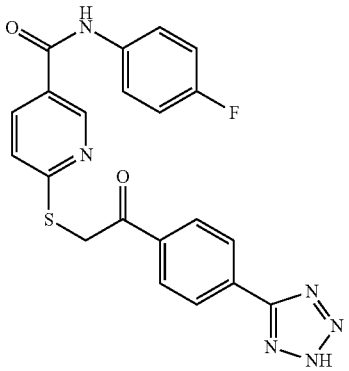

The benzonitrile intermediate was prepared using Method B, and purified using silica gel flash chromatography (EtOAc/hexanes 1:2) to yield 0.9 g (53%) as a yellow solid. As in Synthesis Example 14, the tetrazole moiety was prepared from the nitrile using TMS-azide and dibutyl tin oxide as a catalyst. Silica gel chromatography (MeOH/EtOAc 1:3) was used to purify compound 104 as a yellow solid (160 mg, 93%). TLC (15% MeOH/EtOAc) $R_f$=0.15. ESI-MS m/z=434.9 $[M+H]^+$.

SYNTHESIS EXAMPLE 16

Synthesis of N-(4-fluoro-phenyl)-N-pyridin-2-ylmethyl-6-chloro-nicotinamide Intermediate X

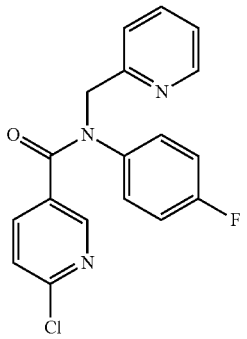

In a round bottom flask, N-(4-fluoro-phenyl)-6-chloro-nicotinamide (0.905 g, 3.62 mmol) and 2-bromomethyl-pyridine hydrobromide (0.915 g, 3.62 mmol) was suspended in toluene (5 ml). 50% aqueous sodium hydroxide (2.0 mL) was added to the reaction mixture, followed by tetra-n-butyl-ammonium hydroxide (100 ul). The biphasic reaction mixture was vigorously stirred overnight, and the aqueous layer removed by pipette. The organic layer was diluted with ethyl acetate (20 mL) and washed with water, saturated aqueous sodium chloride and dried over sodium sulfate. The organic layer was filtered and removed by rotary evaporation to yield 1.19 g (96%) of nicotinamide intermediate X as an off white solid. ESI-MS m/z=341.9, 343.9 $[M+H]^+$.

SYNTHESIS EXAMPLE 17

Synthesis of N-(4-fluoro-phenyl)-N-pyridin-2-ylmethyl-6-mercapto-nicotinamide Intermediate XI

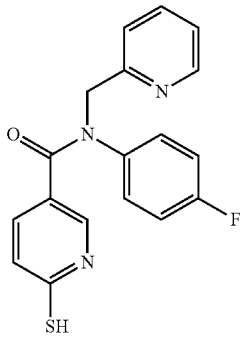

In a round bottom flask, N-(4-fluoro-phenyl)-N-pyridin-2-ylmethyl-6-chloro-nicotinamide intermediate X (1.078 g, 3.16 mmol) and anhydrous sodium hydrogen sulfide (0.354 g, 6.32 mmol) was suspended in anhydrous dimethylformamide (10 mL). The suspension was heated to reflux, and the reaction mixture turned a deep green color. After 1 h, the reaction mixture was diluted with ethyl acetate (50 mL) and washed with water (20 mL). The aqueous layer was back extracted with ethyl acetate (2×20 ml), and the organic layers combined and washed with saturated aqueous sodium chloride, dried over sodium sulfate, filtered and evaporated by rotary evaporation to yield 0.88 g (82%) of thionicotinamide intermediate XI as a dark yellow oil. TLC (EtOAc/hexanes, 2:1) $R_f$=0.1; ESI-MS m/z=339.9 $[M+H]^+$.

SYNTHESIS EXAMPLE 18

Synthesis of Compound 155

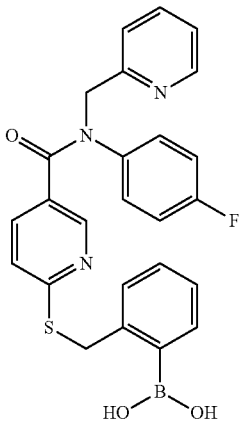

In a round bottom flask, N-(4-fluoro-phenyl)-N-pyridin-2-ylmethyl-6-mercapto-nicotinamide intermediate XI (0.88 g, 2.59 mmol) and 2-bromomethyl-phenylboronic acid (0.56 g, 2.59 mmol) was suspended in ethanol (30 mL). 1 N aqueous sodium hydroxide (2.59 mL, 2.59 mmol) was added to the reaction mixture, and the suspension brought to reflux. After 1 hour, the reaction mixture was diluted with ethyl acetate (30 mL) and washed with water, saturated aqueous sodium chloride, dried over sodium sulfate, filtered and evaporated to yield 0.96 g (79%) of compound 153 as a light yellow foam. ESI-MS m/z=473.9 $[M+H]^+$.

SYNTHESIS EXAMPLE 19

Synthesis of N-substituted Aniline Intermediate XII

The purchased N-Boc-2-piperidine methanol (1.4 g, 1 eq.) was dissolved in ethyl acetate (50 mL) and charged with 2-iodoxybenzoic acid (3.4 g, 1.1 eq.). The resulting slurry was stirred under inert atmosphere and DMSO (781 μL, 2.2 eq.) was added via syringe and the reaction was stirred overnight. Solid material was removed by filtration and the filtrate washed with 10% $NaS_2O_3$/saturated $NaHCO_3$ (1:1, 3×20 mL), water (1×20 mL) and brine (1×20 mL). The organic layer was then removed in vacuo to afford 1.3 g of the aldehyde (94% yield). Coupling was then achieved by dissolving the aldehyde (1.1 g, 1 eq.) and 4-fluoroaniline (481 μL, 1 eq.) in dichoroethane (20 mL). Under an inert atmosphere $NaBH(OAc)_3$ (1.5 g, 1.4 eq.) and concentrated acetic acid (294 μL, 1 eq.) were added and the reaction was monitored by TLC and LC-MS. The mixture was diluted with ethyl acetate and washed with 10% citric acid (×3), brine (x1) and dried over magnesium sulfate. The mixture was filtered and the solvent removed by rotary evaporation and dried in vacuo to afford 1.4 g of the intermediate XII secondary aniline (90% yield). ESI-MS m/z=309.1 $[M+H]^+$.

SYNTHESIS EXAMPLE 20

Synthesis of thionicotinamide Intermediate XIII

The aniline intermediate XII (0.5 g, 1 eq.) was stirred in DMF (5 mL) at 80° C. followed by the addition of 1,8-Diazabicyclo[5.4.0]undec-7-ene (DBU, 240 μL, 1 eq.) and 6-chloronicotinoyl chloride (0.3 g, 1 eq.). The reaction was monitored by TLC and LC-MS and was stirred overnight at 80° C. The mixture was then diluted with ethyl acetate (25 mL) washed with water, saturated sodium bicarbonate, 10% citric acid, water, brine, dried with sodium sulfate and filtered. The organic solvent was then removed by rotary evaporation and dried in vacuo to afford 0.56 g of the tertiary amide (78% yield). Thiolation was then achieved by suspending the tertiary amide (0.56 g, 1 eq.) and sodium hydrogen sulfide (0.14 g, 2 eq.) in anhydrous DMF (2 mL) under an inert atmosphere. The reaction was gently refluxed for two hours and then diluted with ethyl acetate (30 mL) and extracted with water (3×20 mL). The aqueous layer was then acidified with 10% citric acid and stored at 2-8° C. The fine white precipitate was then collected by filtration to afford 0.09 g of thionicotinamide intermediate XIII (16% yield).

SYNTHESIS EXAMPLE 21

Synthesis of Compound 156

Thiol alkylation was achieved by suspending the thionicotinamide intermediate XIII (90 mg, 1 eq.) and 2-bromomethylphenyl boronic acid (50 mg, 1.1 eq.) in ethanol (1 mL). Then 1 N sodium hydroxide (0.2 mL, 1 eq.) was added and the reaction was gently refluxed for 2 hours. Alkylated product was extracted with ethyl acetate (3×5 mL), washed with water (3×5 mL), brine (3×5 mL) and dried over magnesium sulfate. The organic layer was filtered to remove magnesium sulfate, then removed by rotary evaporation and dried in vacuo to afford 90 mg of the boc-protected piperidine boronic acid. The Boc group was then removed by adding 4 M HCl in dioxane (1 mL) to the Boc-protected piperidine boronic acid (20 mg). The resulting piperidine compound 154 was then purified using preparative HPLC to yield 5 mg (29%) as a white solid. ESI-MS m/z=480.1 $[M+H]^+$.

SYNTHESIS EXAMPLE 22

Synthesis of tert-butyl ester nicotinamide Intermediate XIV

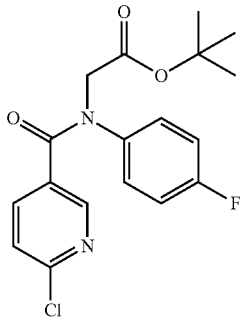

A solution of 4-fluoroaniline (1.00 ml, 10 mmol) and diisopropylethylamine (1.74 mL, 10 mmol) in anhydrous DMF (10 mL) was warmed to 60° C., then a solution of tert-butyl bromoacetate (1.47 mL, 10 mmol) in anhydrous DMF (10 ml) was added drop-wise over 1 hour. After addition, the reaction mixture was kept at 60° C. for 4 hours.

The reaction mixture was then concentrated by rotary evaporation, then partitioned between EtOAc and water. The organic layer was washed with water, then evaporated to yield a dark brown liquid (1.96 g, 87%) TLC (EtOAc/hexanes, 1:4) Rf=0.31; ESI-MS m/z=225.9 $[M+H]^+$. The disubstituted aniline derivative (0.41 g, 2.31 mmol) and was then coupled to 6-chloronicotinoyl chloride (0.52 g, 2.31 mmol) in anhydrous DMF (2 mL) using DBU (344 ml, 2.31 mmol). The reaction mixture was heated to 65° C. for 48 h. The reaction mixture was diluted with EtOAc, and the organic layer washed with $H_2O$. The crude material was concentrated by rotary evaporation, and purified by flash chromatography (EtOAc/hex 1:2) to yield 387 mg (46%) of 6-chloronicotinamide intermediate XIV as a clear oil. TLC (EtOAc/hexanes, 1:2) Rf=0.28; ESI-MS m/z=364.9 $[M+H]^+$.

SYNTHESIS EXAMPLE 23

Synthesis of Compound 158

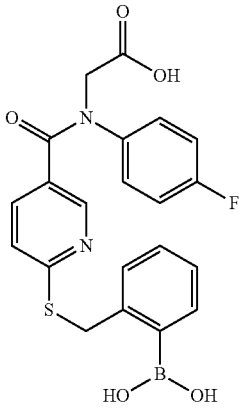

The 6-chloronicotinamide derivative XIV (211 mg, 0.58 mmol) and sodium hydrogen sulfide (74 mg) was dissolved in DMF (1 mL). The reaction mixture was heated to 85° C. for 15 min, then allowed to cool to r.t. The reaction mixture was diluted in EtOAc, and washed with $H_2O$, saturated $NaHCO_3$, $H_2O$, 10% citric acid, $H_2O$, saturated NaCl, and dried over $Na_2SO_4$. The crude material was filtered and evaporated to yield 123 mg (58%) as a yellow oil. TLC (EtOAc) Rf=0.53; ESI-MS m/z=362.9 $[M+H]^+$. The resulting thionicotinamide (110 mg, 0.3 mmol) and 2-bromomethylphenyl boronic acid was coupled using Method B to yield the tert-butyl ester thionicotinamide intermediate (138 mg, 93%). TLC (EtOAc) Rf=0.6; ESI-MS m/z=496.9 $[M+H]^+$. The tert-butyl ester derivative was dissolved in 90% aq. TFA, and let stand at r.t. for 2 h. The TFA was removed by rotary evaporation to yield 74 mg (61%) of compound 156 as an off white hygroscopic solid. ESI-MS m/z=440.9 $[M+H]^+$.

SYNTHESIS EXAMPLE 24

Synthesis of Compound 159

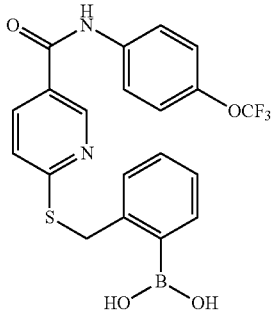

As in Synthesis Example 1,6-mercaptonicotinic acid was coupled to 4-trifluoromethoxyaniline using EEDQ to yield the trifluoromethoxy anilide derivative. Flash silica gel chromatography, using a step gradient (ethyl acetate/hexanes 1:4, then ethyl acetate/hexanes 1:1, then ethyl acetate/hexanes 2:1), was required to purify the compound to yield 318 mg (35%) as a light yellow solid. The trifluoromethoxy thionicotinamide derivative 157 was then prepared via Method B and purified using flash silica gel chromatography (EtOAc/hexanes 1:2 as eluent). Yield of 157: 53 mg (37% yield based on 0.32 mmol scale). ESI-MS m/z=449.1 $[M+H]^+$.

SYNTHESIS EXAMPLE 25

Synthesis of Intermediate XV

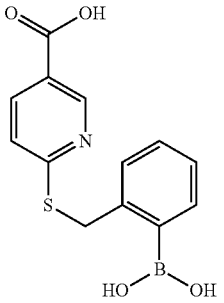

6-Mercaptonicotinic acid (1.55 g, 10 mmol) and 2-bromomethyl-phenylboronic acid (2.14 g, 10 mmol) was dissolved in anhydrous DMF (20 ml), then triethylamine (2.78 mL, 20 mmol) was added. The reaction mixture was warmed to 60° C. for 1 h, then removed from heat and let cool to r.t. The reaction solution was acidified with 1N HCl, and extracted with EtOAc. The EtOAc layer was washed with $H_2O$, saturated NaCl, dried over $Na_2SO_4$ and evaporated to yield intermediate XV as a yellow solid (1.54 g, 53%). TLC (AcOH/EtOAc/EtOH, 0.1:80:20) Rf=0.52; ESI-MS m/z=290.1 $[M+H]^+$.

SYNTHESIS EXAMPLE 26

Synthesis of Intermediate XVI

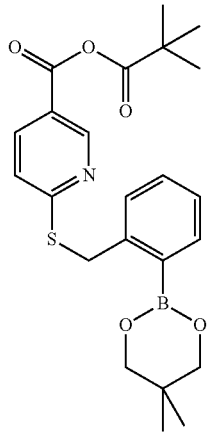

Intermediate XV (290 mg, 1 mmol) and neopentyl glycol (1 mmol) was suspended in anhydrous toluene (5 mL) and set to reflux over 24 h. Without isolation, the resulting mixture containing the boronic ester was cooled in an ice bath under Ar. Pivaloyl chloride (120 μl, 1 mmol) and triethylamine (140 μl, 1 mmol) was then added to the cooled solution. The reaction was allowed to proceed at the lowered temperature for 1 h, then warmed to r.t. for an additional hour. The resulting crystalline triethylammonium salt was filtered away, and the reaction mixture concentrated by rotary evaporation. The resulting oil was diluted with anhydrous DMF (3 ml). This solution was used without further isolation.

SYNTHESIS EXAMPLE 27

Synthesis of Compound 160

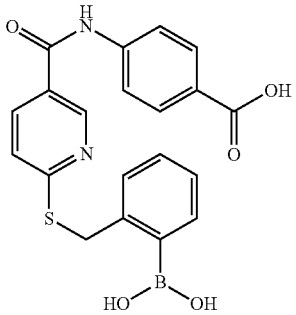

Intermediate XVI was reacted with 4-aminobenzoic acid (70 mg, 0.5 mmol, 1 eq.) and triethylamine (70 ml, 0.5 mmol, 1 eq.) in anhydrous DMF. The reaction mixture was heated to 60° C. for 16 h. The crude material was diluted with EtOAc, and the organic layer washed with $H_2O$ and saturated $NaHCO_3$. The combined aqueous washes were acidified with 1 N HCl, and the resulting crude material was purified using preparative HPLC to yield 23 mg (11%) of compound 158 as a white solid. ESI-MS m/z=409.2 $[M+H]^+$

SYNTHESIS EXAMPLE 28

Synthesis of Compound 161

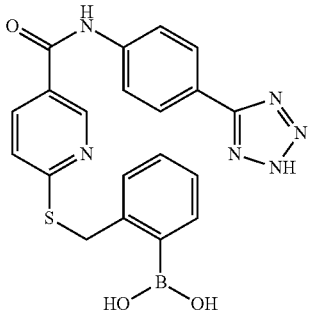

4-Aminobenzonitrile (1.18 g, 10 mmol), trimethylsilylazide (1.31 mL, 10 mmol) and dibutyl tin oxide (248 mg, 1 mmol) was suspended in anhydrous toluene (100 ml) and set to reflux overnight. The reaction solution was decanted to an Erlenmeyer flask while still hot, and a precipitate formed upon cooling to room temperature. The precipitate was filtered and washed with toluene to yield the intermediate 4-tetrazole-aniline (217 mg, 13%). As in Synthesis Example 27, the resulting 4-tetrazole-aniline was reacted with intermediate XVI to yield the crude tetrazole nicotinamide derivative. The crude material was purified using preparative HPLC to yield 38 mg (18%) of compound 159 as a white solid. ESI-MS m/z=433.2 $[M+H]^+$.

SYNTHESIS EXAMPLE 29

Synthesis of Compound 167

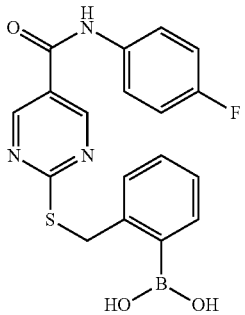

Ethyl-2-(methylthio)-5-pyrimidine carboxylate (1 g, 5 mmol) was dissolved in MeOH (15 mL). 1N NaOH (6 mL) was added, and the reaction mixture stirred for 1 h. The MeOH was removed by rotary evaporator and conc. HCl (500 μl) was added. The resulting precipitate was filtered and washed with $H_2O$ and dried in vacuo to yield 811 mg (95%). The resulting pyrimidine carboxylic acid was coupled to 4-fluoroaniline using EEDQ (as in Synthesis Example 1) to yield 911 mg (73%) of the pyrimidine carboxamide intermediate. The thiomethyl ether moiety of the pyrimidine carboxamide (800 mg, 3.1 mmol) was oxidized with m-CPBA (530 mg, 3.1 mmol) in MeCN (150 mL) for 1 h at r.t., and the resulting precipitate was filtered and dried in vacuo to yield 300 mg (35%) of the oxidized material. The crude mixture (300 mg) was dissolved in anhydrous DMF (20 mL) and sodium hydrogen sulfide (124 mg, 2 mmol) was added. The reaction mixture was brought to gentle reflux for 2 h, then EtOAc (100 mL) was added, and the organic layer washed with $H_2O$. The organic solvent was removed by rotary evaporator, and the 6-mercapto-pyrimidine carboxamide intermediate was purified by preparative HPLC to yield 18 mg of product. The 6-mercapto-pyrimidine carboxamide was then alkylated with 2-bromomethyl-phenylboronic acid via Method B to yield 10 mg (36%) of compound 163 as a white solid. ESI-MS m/z=384.0 $[M+H]^+$.

SYNTHESIS EXAMPLE 30

Bromonicotinamide Intermediate XVII

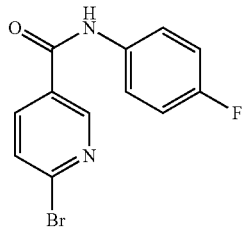

6-Bromonicotinic acid (5.28 g, 26 mmol) and 4-fluoroaniline (2.90 g, 26 mmol) was dissolved in anhydrous DMF (30 mL). EEDQ was added, and the reaction was allowed to progress overnight at room temperature. The solvent was removed by rotary evaporation, and the crude material was dissolved in hot EtOAc (50 mL). Upon cooling, the product crystallized from the solution. The product was filtered, washed with cold EtOAc to yield 3.29 g (43%) as a white solid. ESI-MS m/z=294.9, 296.8 $[M+H]^+$.

SYNTHESIS EXAMPLE 31

Synthesis of N-(4-Fluorophenyl)-6-(2-iodo-benzyloxy)-nicotinamide Intermediate XVIII

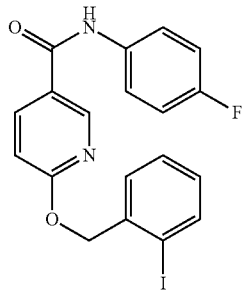

Bromonicotinamide intermediate XVII (1.24 g, 4.21 mmol), 2-iodo-benzyl alcohol (0.986 g, 4.21 mmol), potassium tert-butoxide (0.943 g, 8.42 mmol) and 18-crown-6 (55 mg, 0.21 mmol) was suspended in anhydrous dioxane (15 mL). The reaction mixture was then brought to reflux for 2 hours. The reaction was then cooled to room temperature, and the solution diluted into $H_2O$ (200 mL). The resulting suspension was cooled to 5° C. overnight, then filtered, washed with water and dried to yield 1.199 (64%) as a brown solid. ESI-MS m/z=448.98 $[M+H]^+$.

SYNTHESIS EXAMPLE 32

Synthesis of Boronate Ester Intermediate XIX

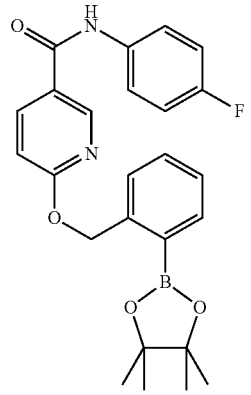

Iodobenzyl nicotinamide intermediate XVIII (200 mg, 0.44 mmol) was dissolved in degassed anhydrous N-methylpyrrolidone (3 mL). Bis(pinacolato) diboron (112 mg, 0.44 mmol), potassium acetate (128 mg, 1.32 mmol) and [1,1'-bis(dipheylphosphino)-ferrocene]-dichloropalladium (II) complex with dichloromethane (12 mg, 0.012 mmol) was added to the solution under a nitrogen atmosphere. The reaction mixture was heated to 80° C. under nitrogen for 16 hours. The solvent was then removed by rotary evaporation, and the crude material reconstituted in EtOAc (30 mL) and washed with $H_2O$ (3×20 mL), saturated NaCl, dried over $Na_2SO_4$, filtered and evaporated to yield 201 mg as a dark oil. The product was purified by radial preparative layer chromatography with EtOAc/hexanes (1:3) as eluent to yield 93 mg (46%) as a clear glass. ESI-MS m/z=449.23 $[M+H]^+$.

SYNTHESIS EXAMPLE 33

Synthesis of Compound 168

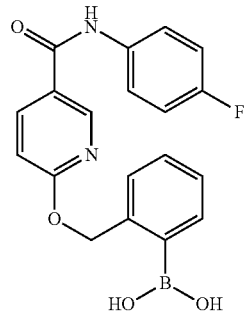

Boronate ester intermediate XIX (75 mg, 0.167 mmol) was deprotected as described in Method D and purified using radial preparative layer chromatography with EtOAc/hexanes (1:1) as eluent to yield 12 mg (20%) as a glass. ESI-MS m/z=367.1 $[M+H]^+$.

SYNTHESIS EXAMPLE 34

Synthesis of Compound 170

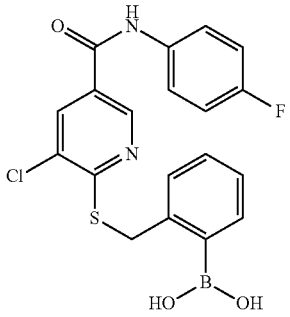

A round bottom was charged with 5,6-dichloronicotinic acid (1 eq, 5 mmol) in DMF (0.5 mmol/mL) followed by the addition of 4-fluoroaniline (1 eq, 5 mmol) and EEDQ (2-Ethoxy-1-ethoxycarbonyl-1,2-dihydroquinoline, 1 eq, 5 mmol). The mixture was stirred overnight then diluted with EtOAc (75 mL), washed with $H_2O$, saturated $NaHCO_3$, $H_2O$, 1N HCl, $H_2O$, brine, dried over sodium sulfate, filtered and solvent removed by rotovap to afford the nicotinamide (92% yield, 4.6 mmol). The nicotinamide (2 mmol) and sodium hydrogen sulfide (4 mmol, 2 eq) were suspended in anhydrous DMF (5 mL) and refluxed for 2 hours. The mixture was diluted with EtOAc (40 mL) and extracted with $H_2O$ (3×20 mL). The water layers were combined and acidified to pH 6-7 with glacial acetic acid. The precipitate was collected by filtration to afford the thiol product (62% yield, 1.23 mmol). The thiol (1.2 mmol) was stirred in EtOH and 1N NaOH (1.2 mmol, 1.2 mL) and charged with 2-bromomethylphenyl boronic acid (1.1 eq, 1.3 mmol). The reaction was stirred at reflux for two hours, diluted with cold water (150 mL), and the precipitate collected by filtration to afford the final boronic acid as an off-white solid, compound 165 (73% yield, 0.88 mmol). ESI-MS m/z=417.03 $[M+H]^+$.

SYNTHESIS EXAMPLE 35

Synthesis of Compound 13a

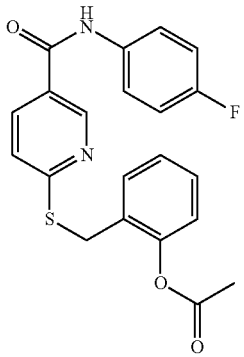

Compound 13 (117 mg, 0.33 mmol) was dissolved in anhydrous DMF (0.5 mL). DMAP (44 mg, 0.36 mmol) was added to the solution, followed by $CH_2Cl_2$ (1 mL). Acetic anhydride (56 μL, 0.59 mmol) was added to the reaction solution, and reaction was stirred at room temperature for 2 hours. By TLC analysis, the reaction was complete. The reaction was quenched with MeOH (5 mL) for 30 min, then concentrated by rotary evaporator. The resulting oil was diluted with EtOAc, and the organic layer washed with $H_2O$, 10% aq. $Na_2CO_3$, $H_2O$, 0.1 N aq. HCl, $H_2O$, brine and dried over $Na_2SO_4$. The organic layer was filtered and evaporated to yield 105 mg (80%) as a white solid. ESI-MS m/z=396.96 $[M+H]^+$.

SYNTHESIS EXAMPLE 36

Synthesis of Compound 137

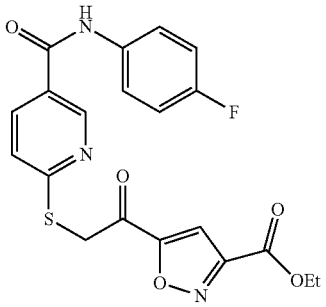

Thionicotinamide intermediate IIa (0.9671 g, 3.82 mmol) and ethyl 5-(2-bromoacetyl)isoxazole-3-carboxylate (0.946 g, 3.82 mmol) was dissolved in anhydrous DMF (10 mL) in a round bottom flask at room temperature. After 4 hours, the reaction was complete. The solvent was removed by rotary evaporation, and the resulting yellow-brown oil was dissolved in EtOAc, washed with $H_2O$, brine, and dried over $Na_2SO_4$. The organic layer was filtered, and evaporated to yield 1.61 g (98%) as a dark colored solid. ESI-MS m/z=430.05 $[M+H]^+$

SYNTHESIS EXAMPLE 37

Synthesis of Compound 138

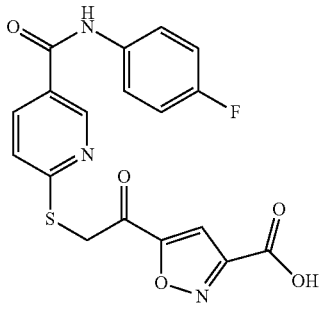

Compound 137 (496 mg, 1.16 mmol) was dissolved in dioxane (8 mL) and 1 N NaOH (2 mL) was added. The reaction mixture was placed in a water bath pre-heated to 40° C. for 4 hours. The reaction mixture was neutralized with 1N HCl (2 mL) and partitioned between EtOAc and $H_2O$. The organic layer was washed with brine, dried over $Na_2SO_4$, filtered and evaporated to yield 355 mg (76%) as a reddish glass. ESI-MS m/z=401.92 $[M+H]^+$

SYNTHESIS EXAMPLE 38

Synthesis of Compound 154

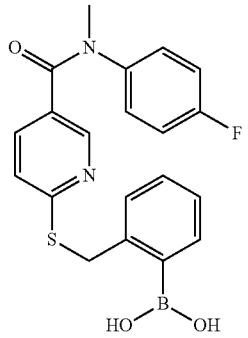

6-Chloronicotinoyl chloride (353 mg, 2.0 mmol) was dissolved in anhydrous DMF (2 mL) and slowly added to a stirring solution of 4-fluoro-N-methylaniline (242 μL, 2.0 mmol) and DBU (300 μL, 2.0 mmol) in anhydrous DMF (2 mL). After 90 minutes, the DMF was removed in vacu and the reaction was partitioned between ethyl acetate and water. The ethyl acetate layer was washed with water and brine, dried over sodium sulfate, filtered, and dried in vacu. The crude solid was purified by silica plug (1:1 ethyl acetate/hexanes) to yield 6-Chloro-N-(4-fluoro-phenyl)-N-methyl-nicotinamide as an off-white, glassy solid (411 mg, 77%).

6-Chloro-N-(4-fluoro-phenyl)-N-methyl-nicotinamide (396 mg, 1.5 mmol) was dissolved in anhydrous DMF (6 mL) under nitrogen. Sodium hydrogen sulfide (181 mg, 1.5 mmol) was added and the solution was refluxed for 70 minutes. After cooling, the solution was diluted with ethyl acetate and washed with water. The water was washed with ethyl acetate, and the combined aqueous layers were acidified with 1 N HCl and extracted with ethyl acetate. The combined ethyl acetate layers were washed with water, saturated sodium bicarbonate, water, and brine, dried over sodium sulfate, filtered, and dried in vacu to yield N-(4-Fluoro-phenyl)-6-mercapto-N-methyl-nicotinamide as a yellow solid (283 mg, 72%).

N-(4-Fluoro-phenyl)-6-mercapto-N-methyl-nicotinamide (274 mg, 1.0 mmol) and 2-Bromomethylphenylboronic acid (230 mg, 1.1 mmol) were dissolved in anhydrous DMF (2 mL). Upon the addition of triethylamine (292 μL, 2.1 mmol), a solid immediately began to crystallize out of the solution, which was left to stand at room temperature for 3 hours. The reaction solution was added to water (50 mL), cooled, and filtered. The solid was purified by silica gel column chromatography (ethyl acetate) to yield Compound 154 as a white foam (90 mg, 22%). ESI-MS m/z=397.04 $[M+H]^+$

SYNTHESIS EXAMPLE 39

Synthesis of Compound 165

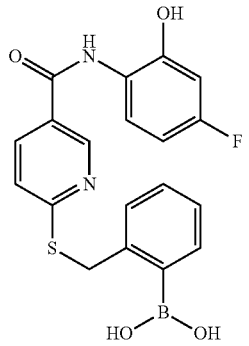

A DMF solution (2 mL) containing 4-fluoro-2-hydroxyaniline (127 mg, 1 mmol), 6-mercaptonicotinic acid (155 mg, 1 mmol) and EEDQ (248 mg, 1 mmol) was stirred under $N_2$ overnight at room temperature. 2-Bromomethylphenyl boronic acid (215 mg, 1 mmol) was added to the reaction mixture for another 16 hours at room temperature. The solvent was then removed by rotary evaporation, and the residue dissolved in EtOAc (25 mL), The organic layer was washed with $H_2O$, 10% $Na_2CO_3$, $H_2O$, 1 N HCl, $H_2O$, brine, and dried over $Na_2SO_4$. The organic layer was filtered and evaporated to yield 215 mg (54%) as a dark glass. ESI-MS m/z=398.94 $[M+H]^+$

SYNTHESIS EXAMPLE 40

Synthesis of Compound 166

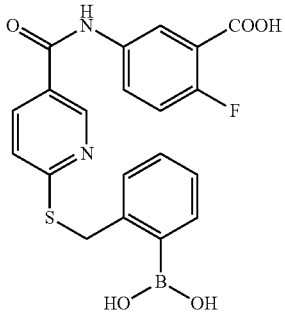

A solution of 5-amino-2-fluorobenzoic acid methyl ester (340 mg, 2 mmol), 6-mercaptonicotinic acid (310 mg, 2 mmol), and EEDQ (500 mg, 2 mmol) in anhydrous DMF (4 mL) was stirred overnight under $N_2$ at room temperature. 2-Bromomethylphenyl boronic acid (428 mg, 2 mmol) was added to the reaction mixture for another 16 hours at room temperature. The solvent was then removed by rotary evaporation, and the residue dissolved in EtOAc (25 mL), The organic layer was washed with $H_2O$, 10% $Na_2CO_3$, $H_2O$, 1 N HCl, $H_2O$, brine, and dried over $Na_2SO_4$. The organic layer was filtered and evaporated to yield 597 mg (68%) of the methyl ester derivative as a light yellow solid. The methyl ester intermediate (200 mg, 0.45 mmol) was dissolved in MeOH (6 mL) and 1 N NaOH (1.35 mL) was added to the reaction mixture. The reaction was stirred for 16 hours at room temperature. The MeOH was removed by rotary evaporation, and the resulting solution acidified with 1N HCl. The resulting solid was washed and dried to yield 87 mg (45%) as an off white solid. ESI-MS m/z=426.93 $[M+H]^+$

SYNTHESIS EXAMPLE 41

Synthesis of Compound 169

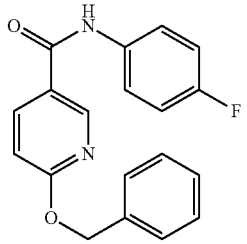

A suspension of bromonicotinamide intermediate XVII (100 mg, 0.339 mmol), benzyl alcohol (176 mL, 1.69 mmol), potassium tert-butoxide (190 mg, 1.69 mmol) and 18-crown-6 (5 mg, 0.02 mmol) in anhydrous THF (3 mL) was heated to reflux for 3 hours. The reaction mixture was then diluted into $H_2O$ (100 mL) and the resulting precipitate was filtered, washed and dried to yield 75 mg (69%) as a white solid. ESI-MS m/z=323.10 $[M+H]^+$

PHARMACOLOGY EXAMPLE 1

In vitro Inhibition of Intracellular Calcium Release

This example shows the results of in vitro assays of several of the compounds listed in Tables 1-5 herein.

An in vitro assay showed inhibition of CXCR2-mediated intracellular calcium release. Briefly, human neutrophils were suspended in HBSS (without $Ca^{2+}$ and $Mg^{2+}$) containing 10 mM HEPES and FLIPR Calcium 3 dye ($3.1\times10^7$ cells in total volume 1.7 mL). Cells were aliquoted (200 μL of the cell suspension per tube, 8 tubes total) and 2 μL of the designated compound (with appropriate dilutions) were added to each of 6 tubes. As controls, 2 μL of DMSO (1% final concentration) were added to 2 other tubes. Cells were incubated for 30 min at 37° C. After dye loading, tubes were centrifuged at 6,000 rpm for 1 min, supernatant was removed and the cell pellet was re-suspended in 200 μL of $HBSS^+$ (with $Ca^{2+}$ and $Mg^{2+}$) containing 10 mM HEPES. The test compound or DMSO (control) was added again at the same concentrations that were used during cell loading. The cell suspension was aliquoted into a 96-well Reading Plate (Corning) in a volume of 90 μL ($10^5$ cells/well). The Compound Plate contained agonist (GROα in $HBSS^-$) or $HBSS^-$ (control). After 15 sec of reading the basal level of fluorescence by FlexStation II, 10 μL of GROα or $HBSS^-$ were automatically transferred from the Compound Plate into the Reading Plate (final concentration of GROα was 25 nM). Changes in fluorescence were monitored ($\lambda_{ex}$=485 nm, $\lambda_{em}$=525 nm) every 5 s for 240 to 500 s at room temperature.

The maximum change in fluorescence, expressed in arbitrary units over baseline (Max-Min), was used to determine the GROα response. The effect of each compound on the GROα response was normalized and expressed as a percent of the DMSO control, which was designated as "100% response." Curve fitting and calculation of the compound inhibitory concentration that reduces the level of the GROα response by 50% ($IC_{50}$), or the compound agonist concentration that increases the level of the calcium release by 50% of the maximum agonist-induced change ($EC_{50}$) were determined by nonlinear regression analysis of the dose-response curves generated using Prism 4 (GraphPad Software, Inc., San Diego, Calif.).

PHARMACOLOGY EXAMPLE 2

Wash-Resistant Inhibition of Intracellular Calcium Release

Compounds 1 (SX-517) and 2 (SX-576) contain a boronic acid functional group, which has the potential to form a covalent linkage with hydroxyl groups located at the binding site of the protein target. Such a covalent linkage could result in a wash-resistant, long-lasting inhibition of CXCR2. In order to test this, SX-576 was incubated with isolated human neutrophils at various concentrations, washed, resuspended in assay buffer containing 2% serum, and assayed for GROα-mediated calcium response at time points up to 6 h after inhibitor washout. Briefly, human neutrophils were isolated as in Pharmacology Example 1. The cells were washed and resuspended in RPMI/2% serum (serum was obtained from the same donor as the neutrophils). The concentration of the neutrophil suspension was $10^7$ cells/mL. Neutrophil aliquots were incubated with the following final concentrations of SX-576 (μM): 0 (positive control), 0 (negative control), 0.4, 2, and 10. Incubation with SX-576 proceeded for 30 minutes at 37° C. The neutrophils were washed and resuspended in RPMI/2% serum and maintained at room temperature. At 30 minutes before each time point, a 56.25 μL aliquot of the neutrophils were removed and loaded for 30 minutes at room temperature in the dark with FLIPR-3 reagent (262.5 μL per tube). Following FLIPR-3 incubation, neutrophils were assayed for GROα mediated intracellular calcium release as in Pharmacology Example 1. In FIG. 1, evidence of dose-dependent and wash-resistant inhibition of GROα mediated intracellular calcium release can be seen out to 6 hours.

PHARMACOLOGY EXAMPLE 3

In vitro Agonist Activity

An in vitro assay showed agonism of CXCR2-mediated intracellular calcium release. Compounds SX-517, SX-576, SX-578, and SX-585 (see Table 5) were evaluated for intracellular calcium release in human neutrophils (i.e., agonist activity). Intracellular calcium release is a hallmark of CXCR2 activation by endogenous agonists, such as GROα and IL-8. Treatment of human neutrophils with compound 1 (SX-517) did not show agonist activity with respect to the release of intracellular calcium. Compound 2 (SX-576) acted as a potent agonist with an $EC_{50}$ of 1.25 μM that generated a maximum response in intracellular calcium release equal to 100% of the response generated by 25 nM GROα. Compounds 13 (SX-578) and 14 (SX-585) exhibited less potent agonism, with responses of 60% and 15% of the maximal response obtained with 25 nM GROα, respectively. The agonist $EC_{50}$ values for Compounds 13 (SX-578) and 14 (SX-585) were 2.4 and 1.8 μM, respectively.

PHARMACOLOGY EXAMPLE 4

Inhibition of β-Arrestin Recruitment

Figure 2:
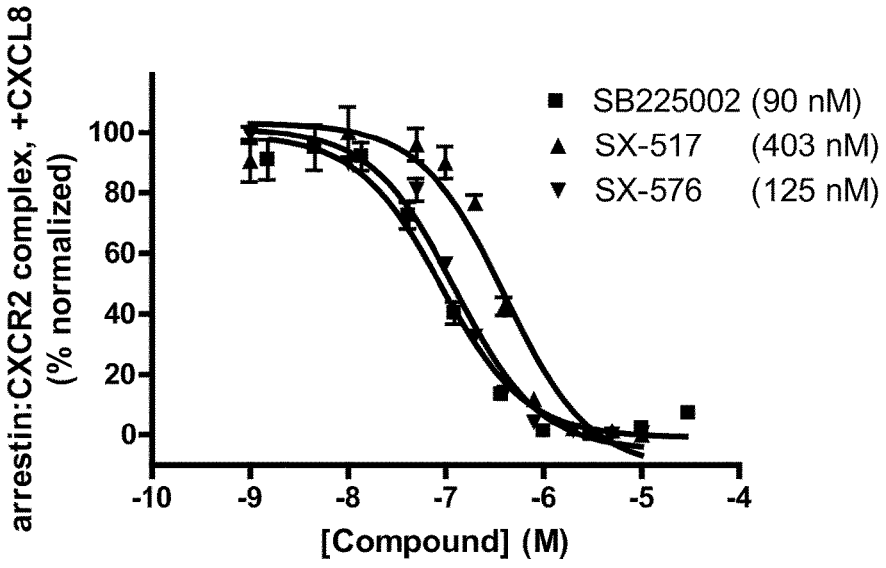
FIG. 2 shows the effect of SX-517 and SX-576 (compounds #1 and #2 in Table 1) on IL8 mediated β-arrestin complexation with CXCR2. SB225002 is included as a positive control.
Figure 3:
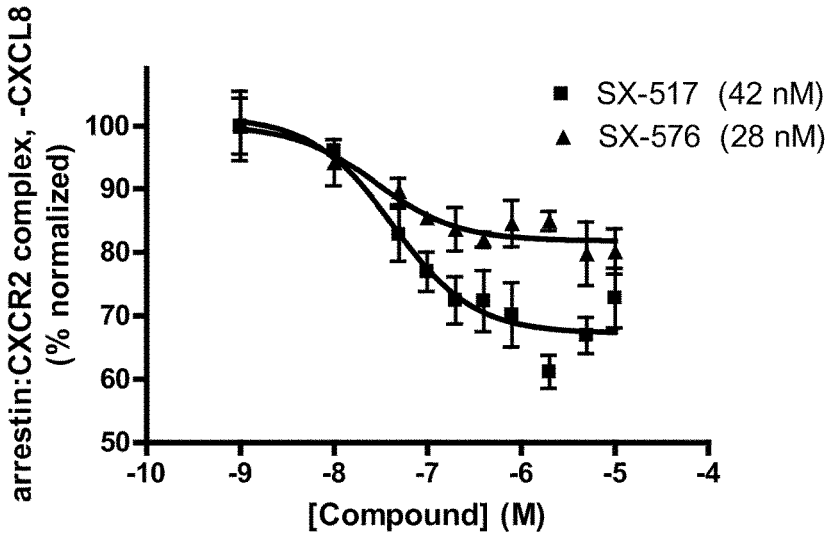
FIG. 3 illustrates the reverse agonist activity of SX-517 and SX-576 (compounds #1 and #2 in Table 1) on β-arrestin complexation with CXCR2 in the absence of IL8.

Compounds 1 (SX-517) and 2 (SX-576) were assayed for inhibition of 13-arrestin recruitment following CXCR2 activation with IL8. The assays were performed by DiscoveRx (Fremont, Calif.). The assay utilized fragment complementation with β-galactosidase (β-Gal) as the functional reporter. β-Gal was split into two complimentary portions expressed as fusion proteins in the cell. One portion was fused to β-arrestin, the other portion is fused to the CXCR2 receptor. Upon CXCR2 activation by IL8, β-arrestin was recruited to the receptor for desensitization, bringing the two fragments of β-Gal together and generating an active enzyme. The active β-Gal converted a chemiluminescent substrate that was detected on a microplate reader. Both SX-517 and SX-576 inhibited arrestin recruitment to the receptor following CXCR2 activation with IL-8 (FIG. 2). SX-576 was a more potent inhibitor than SX-517, comparable to the diarylurea SB225002. In the absence of IL8, SX-517 and SX-576 acted as inverse agonists at CXCR2 (FIG. 3).

PHARMACOLOGY EXAMPLE 5

$^{125}$I-IL-8 Binding Inhibition

In vitro experiments, in addition to those measuring calcium release from human PMNs, provided evidence that the mechanism of action of Compounds 1 and 2 are most consistent with an allosteric (non-competitive) mode of action. In a radioligand binding inhibition experiment, SX-517 (compound 1) was unable to significantly displace radiolabeled IL-8 binding to CXCR2 receptors even at concentrations up to 10 μM. In contrast, the $IC_{50}$ of SX-517 in vitro was approximately 60 nM.

PHARMACOLOGY EXAMPLE 6

Murine Air Pouch Model of Neutrophil Chemotaxis (p.o.)

Figure 4:
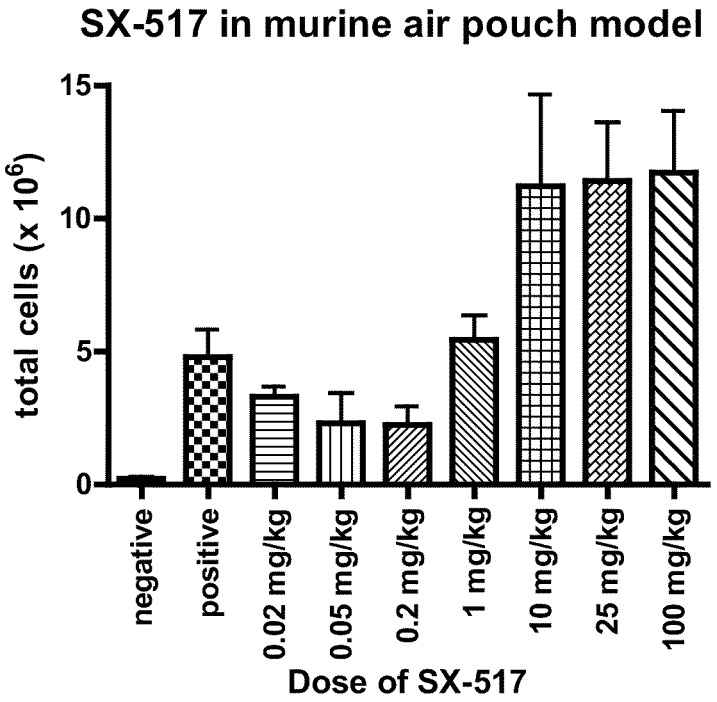
FIG. 4 shows the effect of oral dosing of SX-517 (compound #1 in Table 1) on neutrophil influx in the murine air pouch model as a function of dose.
Figure 5:
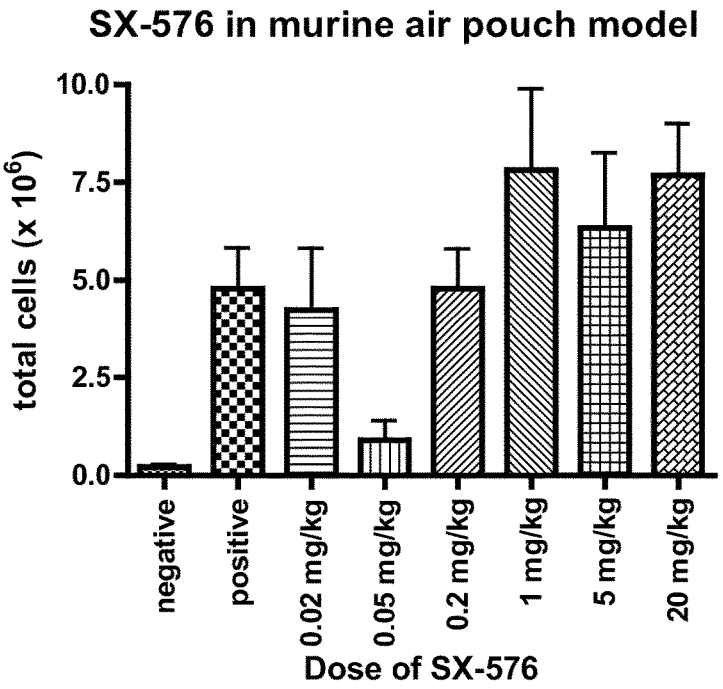
FIG. 5 shows the effect of oral dosing of SX-576 (compound #2 in Table 1) on neutrophil influx in the murine air pouch model as a function of dose.

Compounds 1 (SX-517) and 2 (SX-576) were also assayed in an in vivo air-pouch model of inflammation. SX-517 and SX-576 were able to attenuate neutrophil influx in the air-pouch model by about 50% at an oral dose of 0.2 and 0.05 mg/kg, respectively. At higher concentrations, both SX-517 and SX-576 exhibited agonist activity (i.e., increased neutrophil influx). More specifically, the procedure was performed by forming an air pouch on the backs of male CD-1 mice via the subcutaneous injection of air (2 mL). The next day, an additional subcutaneous injection of air (1.5 mL) was performed to reinflate the air pouch. The mice were given either vehicle control (Labrasol®) or test compound solubilized in Labrasol® via oral gavage. After 3 hours, either sterile phosphate buffered saline (PBS, 1 ml) or 2% carrageenan in sterile PBS (1 mL) was injected into the air pouch. After 4 hours, the mice were sedated with ketamine, and sacrificed by cervical dislocation. The exudate in the air pouch was collected by syringe, with an additional 2 mL wash with sterile PBS. The neutrophils were stained with trypan blue and counted on a hemocytometer under 20× magnification. The results presented in FIG. 4 show a decrease of neutrophil influx was seen when 0.005 and 0.2 of SX-517 (compound 1) was given p.o. The results presented in FIG. 5 show a decrease of neutrophil influx was seen when 0.05 mg/kg of SX-576 (compound 2) was given p.o. Additionally, the results presented in FIGS. 4 and 5 show an increase in neutrophil influx with doses in excess of 10 mg/kg of SX-517 (compound 1) and with doses in excess of 1 mg/kg of SX-576 (compound 2).

The in vivo potency of SX-517 and SX-576 mirrored the results from the in vitro inhibition assays. At higher doses, an increase in neutrophil influx was seen in the model, presumably due to the agonist activity observed in vitro. Without being bound by theory, while SX-517 did not exhibit any agonist activity in vitro, it is hypothesized that SX-517 is partially metabolized to SX-578. Therefore, the agonist activity observed at high doses of SX-517 in vivo can be attributable to high plasma levels of SX-578 due to metabolism. While neutrophil counts in the air pouch exudates were increased at high doses of SX-517 and SX-576, total neutrophil counts in the blood were not significantly changed (i.e., increased or decreased) as compared to control animals (data not shown).

PHARMACOLOGY EXAMPLE 7

Murine Air Pouch Model of Neutrophil Chemotaxis (i.v.)

Figure 6:
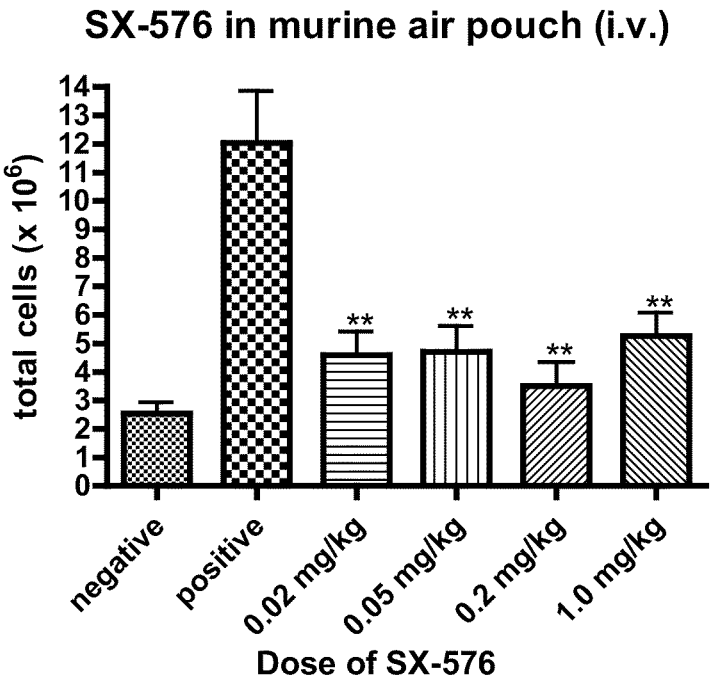
FIG. 6 shows the effect of intravenous dosing of SX-576 (compound #2 in Table 1) on neutrophil influx in the murine air pouch model as a function of dose.

Compound 2 (SX-576) was evaluated via i.v. administration in the murine air pouch model of inflammation. SX-576 was able to significantly attenuate neutrophil influx in the air pouch model at all tested dose levels (0.02, 0.05, 0.2, and 1.0 mg/kg). The procedure was performed by forming an air pouch on the backs of male CD-1 mice via the subcutaneous injection of air (2 mL). The next day, an additional subcutaneous injection of air (1.5 mL) was performed to reinflate the air pouch. The mice were given either vehicle control (dimethylformamide/PEG400/saline) or test compound solubilized in vehicle via tail vein injection. After 30 minutes, either sterile phosphate buffered saline (PBS, 1 ml) or 2% carrageenan in sterile PBS (1 mL) was injected into the air pouch. After 4 hours, the mice were sedated with ketamine, and sacrificed by cervical dislocation. The exudate in the air pouch was collected by syringe, with an additional 2 mL wash with sterile PBS. The neutrophils were stained with trypan blue and counted on a hemocytometer under 20× magnification. Significant decrease in neutrophil influx was observed at all dose levels of SX-576, including 0.02 mg/kg (FIG. 6)

PHARMACOLOGY EXAMPLE 8

Rat Model of Pulmonary Inflammation

Figure 7:
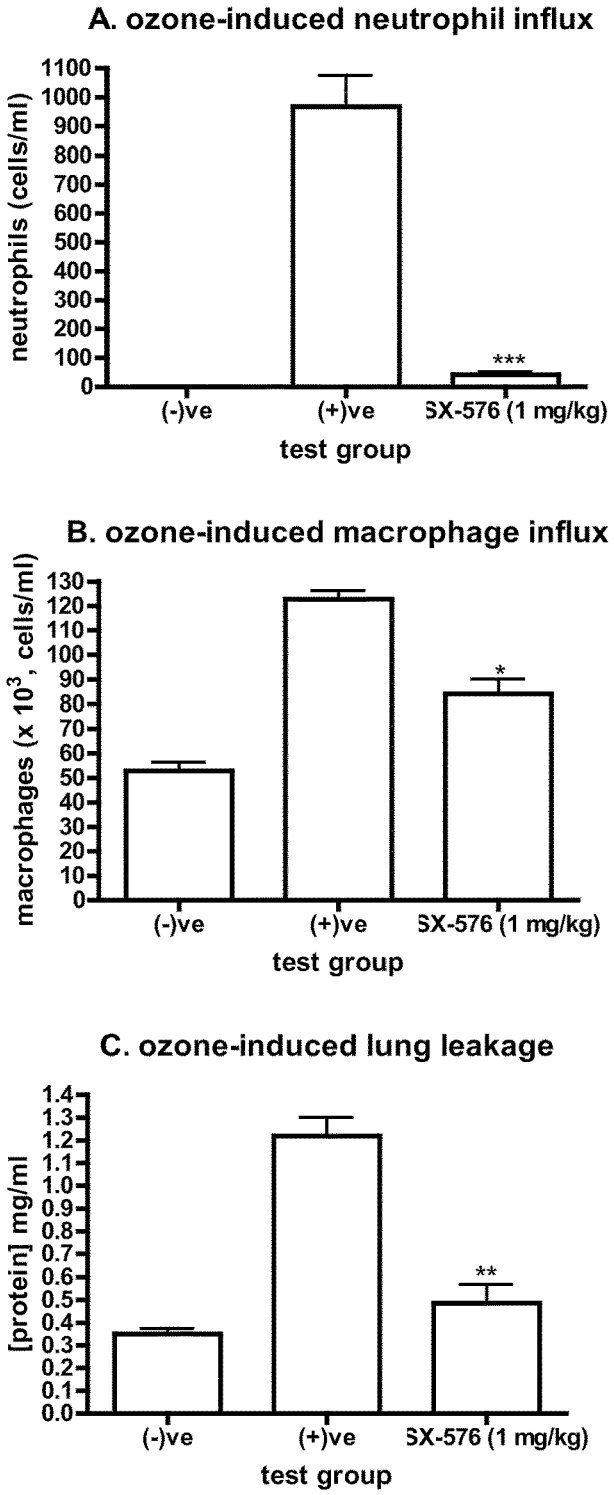
FIG. 7a shows the effect of intravenous dosing of SX-576 (compound #2 in Table 1) on neutrophil influx in the ozone rat model of pulmonary inflammation
FIG. 7b shows the effect of intravenous dosing of SX-576 (compound #2 in Table 1) on macrophage influx in the ozone rat model of pulmonary inflammation
FIG. 7c shows the effect of intravenous dosing of SX-576 (compound #2 in Table 1) on ozone-induced lung leakage in the ozone rat model of pulmonary inflammation

Compound 2 (SX-576) was assayed in an in vivo rat model of pulmonary inflammation. Activity in this model of pulmonary inflammation would provide direct relevance towards the treatment of a number of pulmonary inflammatory diseases, including chronic obstructive pulmonary disease (COPD) and bronchopulmonary dysplasia (BPD). In this experiment, Sprague-Dawley rats (n=4 per cohort) were dosed intravenously at t=0 with either vehicle (negative and positive groups, dimethylformamide/PEG400/saline, 40:40:20) or SX-576 (1 mg/kg). The rats were then placed in air (negative group) or 1 ppm ozone (positive and SX-576 groups) for 4 hours. The rats were dosed again at t=5 and 9 hours. The rats were then sacrificed at t=24 hours, and the bronchoalveolar lavage fluid (BALF) was collected. The cells were spun down, stained with Wright-Giemsa and counted. In the negative groups, no neutrophils were observed when stained. As a measure of lung leakage/damage, protein levels were quantified in BALF by Bradford protein assay analysis. The results are shown in FIGS. 7a-c. In the ozone rat model of pulmonary inflammation, SX-576 (1 mg/kg) significantly decreased the influx of both neutrophils and macrophages into the lungs (FIGS. 7a and 7b), and protected against ozone-induced lung damage (as measured by protein levels in the BALF, FIG. 7c). These results provide evidence that SX-576 is a potent inhibitor of pulmonary neutrophil chemotaxis in vivo, and is effective for treating diseases with a heightened pulmonary inflammation component, like COPD in a predictive in vivo model.

FORMULATION EXAMPLE 1

Crossover Pharmacokinetic Experiment in Beagle Dogs

Figure 8:
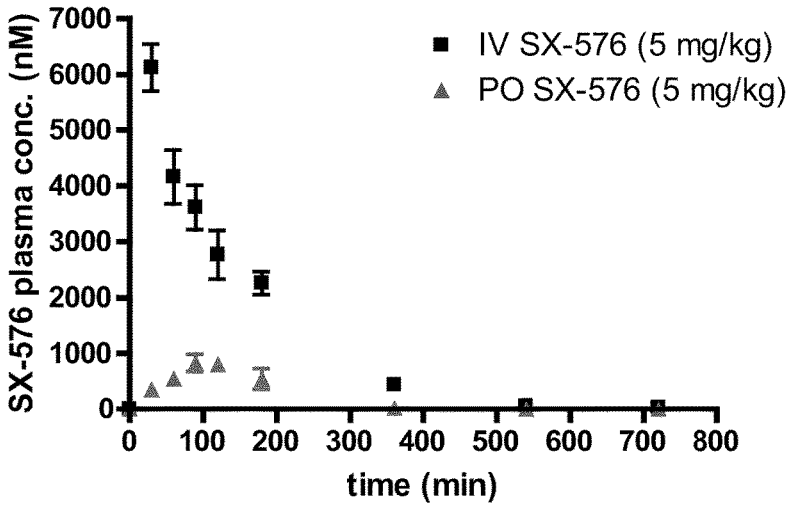
FIG. 8 shows the pharmacokinetic profile of SX-576 (compound #2 in Table 1) following intravenous and oral dosing

Compound 2 (SX-576) was evaluated for oral bioavailability in a crossover pharmacokinetic experiment in Beagle dogs. In this study, male Beagle dogs (n=5) were dosed intravenously on study day 1 with SX-576 in dimethylformamide/PEG400/saline (40:40:20) at a dose level of 5 mg/kg and a dose volume of 0.5 mL/kg. Blood samples were taken predose, and at time points 30, 60, 90, 120, 180, 360, 540 and 720 minutes. The blood was collected in tubes containing K2EDTA as an anticoagulant, and the tubes were centrifuged and the plasma fractions collected and frozen. After a one-week washout period, the same Beagle dogs were dosed orally with SX-576 in lipid based excipient Gelucire® 44/14 (Gattefosse) at a dose level of 5 mg/kg. Blood samples were then taken and plasma fractions collected as previously described. Prior to analysis, the plasma samples were thawed and diluted 1:3 into acetonitrile containing 1 μM of compound 153 as an internal standard. The resulting samples were centrifuged and the supernatant analyzed by LC-MS monitoring in multiple reaction monitoring mode. The samples were run concomitantly with a calibration curve of SX-576 in the same internal standard solution. The plasma levels of SX-576 in this crossover PK study is shown in FIG. 8.

Both SX-517 and SX-576 have poor aqueous solubility. The lipid based excipient Gelucire® 44/14 is a self-emulsifying drug delivery system (SEDDS) that is able to solubilize both SX-517 and SX-576 into aqueous solutions via micellular formation. When dosed to Beagle dogs without excipient, SX-517 and SX-576 were undetected in plasma (data not shown). Gelucire® 44/14 improved the bioavailability of SX-576 following oral administration. Therefore, lipid-based emulsifiers are important excipients for the oral delivery of SX-576.

We claim:

1. A compound comprising a compound from formula (1):

(1)

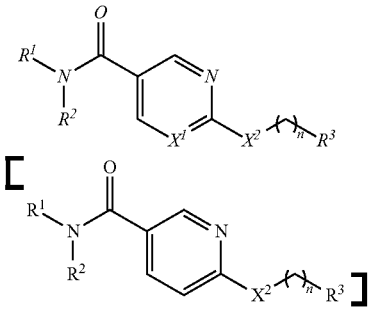

wherein $R^1$ is selected from the group consisting of hydrogen, [2- or 3- or 4-halo-phenyl,] heteroalkyl, alkyl, aryl, arylalkyl, heteroaryl, heteroarylalkyl, *heteroarylaryl, arylheteroaryl, heteroarylheteroaryl, heterocyclylaryl,* cycloalkyl, cycloalkylalkyl, heterocyclyl, and [heterocyclylalkyl] *heterocycloalkylalkyl*;

wherein $R^2$ is selected from the group consisting of [2- or 3- or 4-halo-phenyl,] heteroalkyl, lower alkyl, $C_{7-25}$ alkyl, aryl, arylalkyl, heteroaryl, heteroarylalkyl, *heteroarylaryl, arylheteroaryl, heteroarylheteroaryl, heterocyclylaryl,* cycloalkyl, cycloalkylalkyl, heterocyclyl, and [heterocyclylalkyl] *heterocycloalkylalkyl*, wherein, if substituted, the lower alkyl is selected from the group consisting of methyl, n-propyl, isopropyl, n-butyl, t-butyl, and n-pentyl, and wherein aryl in $R^2$ is unsubstituted or substituted [with] with one or more substituents selected from the group consisting of —C(O)R, —OR, alkyl, aryl, —N(H)R, -N(R)R, [—S—R], —$N_3$, —B(R)R, —$B(OH)_2$, —$B(OR)_2$, —C(O)OH, —C(O)OR, —$C(O)NH_2$, —$S(O)_2NH_2$, —C(O)N(H)R, —C(O)N(R)R, —SH, [—S—R] —*SR*, —$NO_2$, cyano, halo, haloalkyl, haloalkoxy, heterocyclyl, heteroalkyl, —OH, —OC(O)R, —C(O)R, and —$C(O)CH_aX_b$, wherein a+b=3 and X is [selected from the group consisting of] F, Cl or Br, and wherein R is alkyl having less than twelve carbons;

wherein [$R_3$] $R^3$ is selected from the group consisting of —$B(R^4R^5)$, —$R^6$—$B(R^4R^5)$, *substituted* aryl, arylalkyl, cycloalkyl, heteroaryl, heteroarylalkyl, heterocyclyl, [heterocyclylalkyl] *heterocycloalkylalkyl*, [—C(O)—$R^6$, —O—$R^6$, —$S(O)_y$—$R^6$] *heteroarylaryl, heterocyclylaryl, arylheteroaryl, heteroarylheteroaryl,* —$C(O)R^6$, —$OR^6$, —$S(O)_yR^6$ (wherein y =0, 1, or 2), [—P(O)—$(R^4R^5)$] —$P(O)(R^4R^5)$, and —$N(R^7R^8)$, *wherein a heterocyclyl in a bicyclic substituted aryl is a 5 or 6 membered ring*;

wherein $R^6$ is selected from the group consisting of alkyl, aryl, arylalkyl, cycloalkyl, heteroaryl, heteroarylalkyl, heterocyclyl, [and heterocyclylalkyl] *heterocycloalkylalkyl, alkylaryl, arylheteroaryl, heteroarylaryl, and heterocyclylaryl*;

wherein $R^4$ and $R^5$ are independently selected from the group consisting of hydrogen, hydroxyl, aryloxy, and alkoxy, or wherein $R^4$ and $R^5$ together form a cyclic ester, or an acid anhydride (either mixed or symmetrical);

wherein $R^7$ [and $R^8$ are independently] *is* selected from the group consisting of [from] hydrogen, *C7-C18* alkyl, haloalkyl, aryl, cycloalkyl, arylalkyl, heteroalkyl, heterocyclyl, and [heterocyclylalkyl] *heterocycloalkylalkyl*; *$R^8$ is selected from the group consisting of C7-C18 alkyl, haloalkyl, aryl, cycloalkyl, arylalkyl, heteroalkyl, heterocyclyl, and heterocycloalkylalkyl;* $R^7$ and $R^8$ are both oxygen; or $R^7$ and $R^8$ form a heterocyclyl; and wherein *$X^1$ is —CH— or —CCl—*, $X^2$ is [—$S(O)_y$-] —$S(O)_y$— (wherein y=0, 1, or 2) [or oxygen]; and n is an integer between 1 and 8*; or*

*a pharmaceutically acceptable solvated or unsolvated form thereof; a pharmaceutically acceptable salt thereof; or a pharmaceutical composition thereof.*

2. The compound of claim 1 wherein [$R^1$] $R^1$ is hydrogen and $R^2$ is 4-fluorophenyl.

3. The compound of claim 1 wherein y=0.

4. The compound of claim 1 wherein the compound is

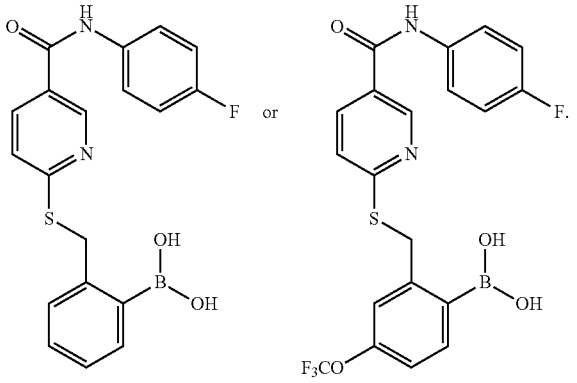

5. A compound comprising a compound from formula (1):

(1)

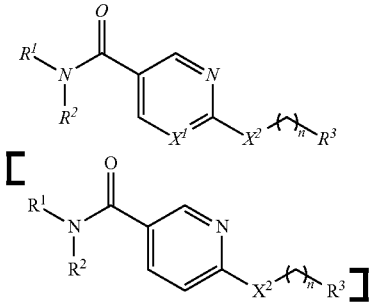

wherein [$R^1$] $R^1$ is selected from the group consisting of hydrogen, [2- or 3- or 4-halo-phenyl,] heteroalkyl, alkyl, aryl, arylalkyl, heteroaryl, heteroarylalkyl, *heteroarylaryl, arylheteroaryl, heteroarylheteroaryl, heterocyclylaryl,* cycloalkyl, cycloalkylalkyl, heterocyclyl, and [heterocyclylalkyl] *heterocycloalkylalkyl*;

wherein $R^2$ is [an unsubstituted or] *a* substituted $C_{1-18}$ alkyl, wherein the alkyl [substituents are] *substituent is* selected from the group consisting of hydroxy, alkylamino, boronyl, carboxy, nitro, and cyano;

wherein [$R_3$] $R^3$ is selected from the group consisting of —B($R^4R^5$), —$R^6$—B($R^4R^5$), *substituted* aryl, arylalkyl, cycloalkyl, heteroaryl, heteroarylalkyl, heterocyclyl, [heterocyclylalkyl] *heterocycloalkylalkyl, heteroarylaryl, arylheteroaryl, heteroarylheteroaryl, heterocyclylaryl,* —C(O)$R^6$, —O$R^6$, —S(O)$_y$$R^6$ (wherein y=0, 1, or 2), —P(O)($R^4R^5$), and —N($R^7R^8$);

wherein $R^4$ and $R^5$ are independently selected from the group consisting of hydrogen, hydroxyl, aryloxy, and alkoxy; or wherein $R^4$ and $R^5$ form a mixed or symmetrical cyclic ester or acid anhydride;

wherein $R^6$ is selected from the group consisting of alkyl, aryl, arylalkyl, cycloalkyl, heteroaryl, heteroarylalkyl, heterocyclyl [and heterocyclylalkyl], *heterocycloalkylalkyl, alkylaryl, arylheteroaryl, heteroarylaryl, and heterocyclylaryl*;

wherein $R^7$ and $R^8$ are independently selected from the group consisting of hydrogen, alkyl, haloalkyl, aryl, cycloalkyl, arylalkyl, heteroalkyl, heterocyclyl, and [heterocyclylalkyl] *heterocycloalkylalkyl*; $R^7$ and $R^8$ are both oxygen; or $R^7$ and $R^8$ form a heterocyclyl; and wherein *$X^1$ is —CH— or —CCl—*, $X^2$ is [—S(O)$_y$-] *—S(O)$_y$—* (wherein y=0, 1, or 2) or oxygen; and n is an integer between 1 and 8*; or*

*a pharmaceutically acceptable solvated or unsolvated form thereof; a pharmaceutically acceptable salt thereof; or a pharmaceutical composition thereof.*

6. A compound comprising a compound from formula (1):

(1)

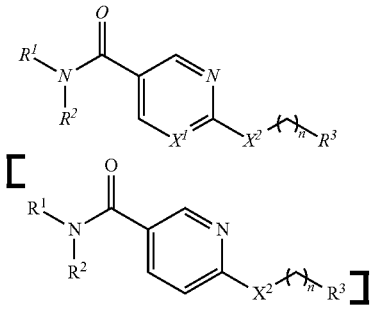

wherein [$R^1$] $R^1$ is selected from the group consisting of hydrogen, [2- or 3- or 4-halo-phenyl,] heteroalkyl, alkyl, aryl, arylalkyl, heteroaryl, heteroarylalkyl, cycloalkyl, cycloalkylalkyl, heterocyclyl, [and heterocyclylalkyl] *heterocycloalkylalkyl, alkylaryl, arylheteroaryl, heteroarylaryl, and heterocyclylaryl*;

wherein $R^2$ is [a fluoro-substituted hydrocarbon wherein the hydrocarbon is] selected from the group consisting of [aryl, arylalkyl,] *fluoro-substituted* heteroaryl, heteroarylalkyl, [cycloalkyl, cycloalkylalkyl,] heterocyclyl, [and heterocyclylalkyl] *heterocycloalkylalkyl, arylheteroaryl, heteroarylaryl, and heterocyclylaryl*;

wherein $R^3$ is selected from the group consisting of —B($R^4R^5$), —$R^6$—B($R^4R^5$), [aryl,] *substituted* arylalkyl, *substituted* cycloalkyl, *unsubstituted* heteroaryl, *heteroaryl substituted by one or more substituents selected from —C(O)R, —OR, alkyl, aryl, —N(H)R, —N(R)R, amino, azido, —B(R)R, —B(OH)$_2$, —B(OR)$_2$, —C(O)OR, aminocarbonyl, aminosulfonyl, —C(O)NHR, —C(O)N(R)R, cyano, halo, haloalkyl, haloalkoxy, heterocyclyl, heteroalkyl, hydroxyl, —OC(O)R, —C(O)R, substituted halomethylketone, —SH, —SR, and nitro, where R is an alkyl having less than 12 carbons,* heteroarylalkyl, heterocyclyl *selected from the group consisting of lactam, lactone, piperidyl, piperazinyl, thiomorpholinyl, thiazolidinyl, 1,3-dioxolanyl, 1,4-dioxanyl, tetrahydrofuranyl, tetrahydrothiophenyl and tetrahydrothiopyranyl, heterocycloalkylalkyl, heteroarylaryl, arylheteroaryl, heteroarylheteroaryl, heterocyclylaryl*, heterocyclylalkyl, —C(O)$R^6$, —O$R^6$, —S(O)$_y$$R^6$ (wherein y=0, 1, or 2), —P(O)($R^4R^5$), and —N($R^7R^8$);

wherein $R^4$ and $R^5$ are independently selected from the group consisting of hydrogen, hydroxyl, aryloxy, and alkoxy, or wherein $R^4$ and $R^5$ together form a mixed or symmetrical cyclic ester or acid anhydride;

wherein $R^6$ is selected from the group consisting of alkyl, aryl, arylalkyl, cycloalkyl, heteroaryl, heteroarylalkyl, heterocyclyl, [and heterocyclylalkyl] *heterocycloalkylalkyl, alkylaryl, arylheteroaryl, heteroarylaryl, and heterocyclylaryl*;

wherein $R^7$ and $R^8$ are independently selected from the group consisting of hydrogen, alkyl, haloalkyl, aryl, cycloalkyl, arylalkyl, heteroalkyl, heterocyclyl, and [heterocyclylalkyl] *heterocycloalkylalkyl*; $R^7$ and $R^8$ are both oxygen; or $R^7$ and $R^8$ form a heterocyclyl; and wherein *$X^1$ is —CH— or —CCl—*, $X^2$ is [—$S(O)_y$-] —*$S(O)_y$*— (wherein y=0, 1, or 2) or oxygen; and n is an integer between 0 and 8;

*a pharmaceutically acceptable solvated or unsolvated form thereof, a pharmaceutically acceptable salt thereof; or a pharmaceutical composition thereof.*

7. The compound of claim 6, wherein $R^3$ is —$R^6$—B($R^4R^5$).

8. The compound of claim 7, wherein $R^3$ is —$R^6$—B$(OH)_2$.

9. The compound of claim 7, wherein $R^6$ is an aryl substituted with an F, —$OCF_3$, or —$OCH_3$.

10. The compound of claim 6, wherein $R^3$ is a halo-substituted [hydrocarbon selected from the group consisting of aryl,] arylalkyl, *halo-substituted* cycloalkyl, *halo-substituted* heteroaryl, *halo-substituted* heteroarylalkyl, *halo-substituted* heterocyclyl [and heterocyclylalkyl], *or halo-substituted heterocycloalkylalkyl*.

11. The compound of claim 6, wherein $R^3$ is —C(O)$R^6$, wherein $R^6$ is a halo-substituted [hydrocarbon selected from the group consisting of aryl,] arylalkyl, *halo-substituted* cycloalkyl, *halo-substituted* heteroaryl, *halo-substituted* heteroarylalkyl, *halo-substituted* heterocyclyl, [and heterocyclylalkyl] *or halo-substituted heterocycloalkylalkyl*.

12. The compound of claim 11, wherein $R^6$ is a halo-substituted aryl.

13. The compound of claim 6, wherein y=0.

14. The compound of claim 6 wherein [$R_3$] *$R^3$* is

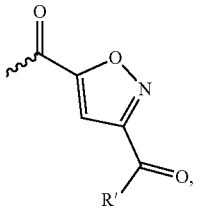

wherein R' is [OH, O-alkyl, or O-aryl] *—OH, —O-alkyl, or —O-aryl*.

15. The compound of claim 6, wherein $R^3$ is [—$R^6$ or] —C(O)$R^6$ wherein $R^6$ is [a hydroxy-substituted hydrocarbon] selected from the group consisting of [aryl,] *hydroxy-substituted* arylalkyl, *hydroxy-substituted* cycloalkyl, *hydroxy-substituted* heteroaryl, *hydroxy-substituted* heteroarylalkyl, *hydroxy-substituted* heterocyclyl, and [ heterocyclylalkyl] *hydroxy-substituted heterocycloalkylalkyl*.

16. The compound of claim 6, wherein[, $R^1$] *$R^1$* is hydrogen.

*17. A compound comprising a compound from formula (1):*

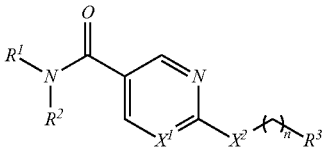

(1)

*wherein $R^1$ is selected from the group consisting of hydrogen, heteroalkyl, alkyl, aryl, arylalkyl, heteroaryl, heteroarylalkyl, cycloalkyl, cycloalkylalkyl, heterocyclyl, heterocycloalkylalkyl, alkylaryl, arylheteroaryl, heteroarylaryl, and heterocyclylaryl;*

*wherein $R^2$ is a fluoro-substituted substituent compound selected from the group consisting of fluoro-substituted heteroaryl, heteroarylalkyl, heterocyclyl, heterocycloalkylalkyl, arylheteroaryl, heteroarylaryl, and heterocyclylaryl;*

*wherein $R^3$ is selected from the group consisting of —B($R^4R^5$), —$R^6$—B($R^4R^5$), substituted aryl, arylalkyl, cycloalkyl, heteroaryl, heteroarylalkyl, heterocyclyl selected from the group consisting of lactam, lactone, piperidyl, piperazinyl, thiomorpholinyl, thiazolidinyl, 1,3-dioxolanyl, 1,4-dioxanyl, tetrahydrofuranyl, tetrahydrothiophenyl and tetrahydrothiopyranyl, heterocycloalkylalkyl, heteroarylaryl, arylheteroaryl, heteroarylheteroaryl, heterocyclylaryl, —C(O)$R^6$, —O$R^6$, —$S(O)_yR^6$ (wherein y=0, 1, or 2), —P(O)($R^4R^5$), and —N($R^7R^8$);*

*wherein $R^4$ and $R^5$ are independently selected from the group consisting of hydrogen, hydroxyl, aryloxy, and alkoxy, or wherein $R^4$ and $R^5$ together form a mixed or symmetrical cyclic ester or acid anhydride;*

*wherein $R^6$ is selected from the group consisting of-alkyl, aryl, arylalkyl, cycloalkyl, heteroaryl, heteroarylalkyl, heterocyclyl, heterocycloalkylalkyl, alkylaryl, arylheteroaryl, heteroarylaryl, and heterocyclylaryl;*

*wherein $R^7$ and $R^8$ are independently selected from the group consisting of hydrogen, alkyl, haloalkyl, aryl, cycloalkyl, arylalkyl, heteroalkyl, heterocyclyl, and heterocyclylalkyl; $R^7$ and $R^8$ are both oxygen; or $R^7$ and $R^8$ form a heterocyclyl; and*

*wherein $X^1$ is —CH— or —CCl—, $X^2$ is —$S(O)_y$— (wherein y=0, 1, or 2) or oxygen; and n is an integer between 1 and 8;*

*a pharmaceutically acceptable solvated or unsolvated form thereof; a pharmaceutically acceptable salt thereof; or a pharmaceutical composition thereof.*

*18. The compound of claim 1, wherein $R^3$ is —B($R^4R^5$), —$R^6$B($R^4R^5$), or —P(O)($R^4R^5$).*

*19. The compound of claim 18, wherein y is 0.*

*20. The compound of claim 18, wherein $R^6$ is an aryl substituted with an F, —$OCF_3$, or —$OCH_3$.*

*21. The compound of claim 5, wherein $R^3$ is —B($R^4R^5$), —$R^6$B($R^4R^5$), or —P(O)($R^4R^5$).*

*22. The compound of claim 21, wherein y is 0.*

*23. The compound of claim 21, wherein $R^6$ is an aryl substituted with one or more substituents selected from F, —$OCF_3$, and —$OCH_3$.*

*24. The compound of claim 3, wherein $R^3$ is an aryl substituted with one or more substituents selected from a halide, —OH, —OC(O)R, —$OCF_3$, —$OCH_3$, —C(O)R, —R, —$NO_2$, and —B($R^4R^5$), wherein R is alkyl having less than 12 carbons, or hydroxy.*

*25. The compound of claim 5, wherein $R^3$ is an aryl substituted with one or more substituents selected from a halide, —OH, —OC(O)R, —$OCF_3$, —$OCH_3$, —C(O)R, —R, —$NO_2$, and —B($R^4R^5$); and y is 0, wherein R is alkyl having less than 12 carbons, or hydroxy.*

*26. The compound of claim 13, wherein $R^3$ is a heteroaryl substituted with one or more substituents selected from a halide, —OH, —OC(O)R, —$OCF_3$, —$OCH_3$, —C(O)R, —$NO_2$, and —B($R^4R^5$).*

*27. The compound of claim 3, wherein $R^3$ is an aryl or a heteroaryl substituted with one or more substituents selected*

*from a halide, —OH, —OC(O)R, —$OCF_3$, —$OCH_3$, —C(O)R, —$CF_3$, —$NO_2$, —$SO_2$-phenyl, —$NH_2$, and —B($R^4R^5$), wherein R is alkyl having less than 12 carbons, or hydroxy.*

*28. The compound of claim 5, wherein $R^3$ is an aryl or a heteroaryl substituted with one or more substituents selected from a halide, —OH, —OC(O)R, —$OCF_3$, —$OCH_3$, —C(O)R, —$CF_3$, —$NO_2$, —$SO_2$-phenyl, —$NH_2$, and —B($R^4R^5$), wherein R is alkyl having less than 12 carbons, or hydroxy; and y is 0.*

*29. The compound of claim 13, wherein $R^3$ is a heteroaryl substituted with one or more substituents selected from a halo, —OH, —OC(O)R, —$OCH_3$, —C(O)R, —$CF_3$, —$NO_2$, —$NH_2$, and —B(R)R.*

*30. The compound of claim 3, wherein $R^3$ is —$OR^6$ or —C(O)$R^6$.*

*31. The compound of claim 5, wherein $R^3$ is —$OR^6$ or —C(O)$R^6$; and y is 0.*

*32. The compound of claim 13, wherein $R^3$ is —$OR^6$ or —C(O)$R^6$.*

*33. The compound of claim 3, wherein $R^3$ is arylalkyl, arylheteroaryl, heteroarylalkyl, heteroarylaryl, heteroarylheteroaryl, heterocyclylaryl, heterocyclyl, or heterocycloalkylalkyl.*

*34. The compound of claim 5, wherein $R^3$ is arylalkyl, arylheteroaryl, heteroarylalkyl, heteroarylaryl, heteroarylheteroaryl, heterocyclylaryl, heterocyclyl, or heterocycloalkylalkyl; and y is 0.*

*35. The compound of claim 13, wherein $R^3$ is arylalkyl, arylheteroaryl, heteroarylalkyl, heteroarylaryl, heteroarylheteroaryl, heterocyclylaryl, heterocyclyl, or heterocycloalkylalkyl.*

*36. The compound of claim 3, wherein $R^3$ is heterocyclyl or is selected from the group consisting of*

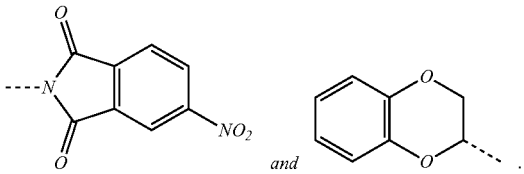

*37. The compound of claim 5, wherein y is 0, and $R^3$ is heterocyclyl or is selected from the group consisting of*

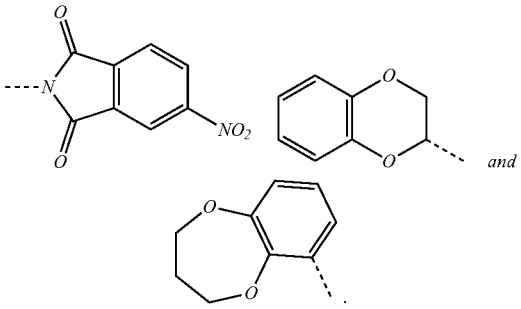

*38. The compound of claim 13, wherein $R^3$ is heterocyclyl or is selected from the group consisting of*

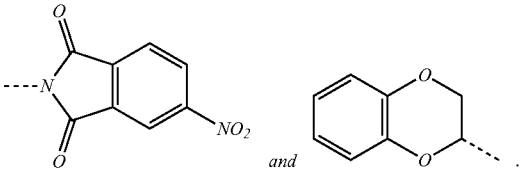

*39. The compound of claim 3, wherein $R^3$ is —C(O)$R^6$, and wherein $R^6$ is selected from the group consisting of*

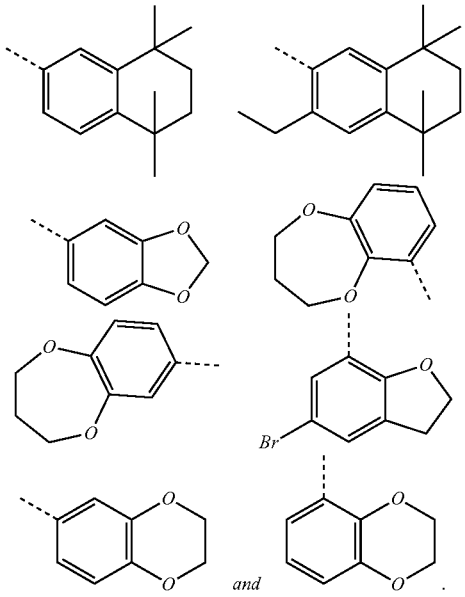

*40. The compound of claim 5, wherein y is 0, wherein $R^3$ is —C(O)$R^6$, and wherein $R^6$ is selected from the group consisting of*

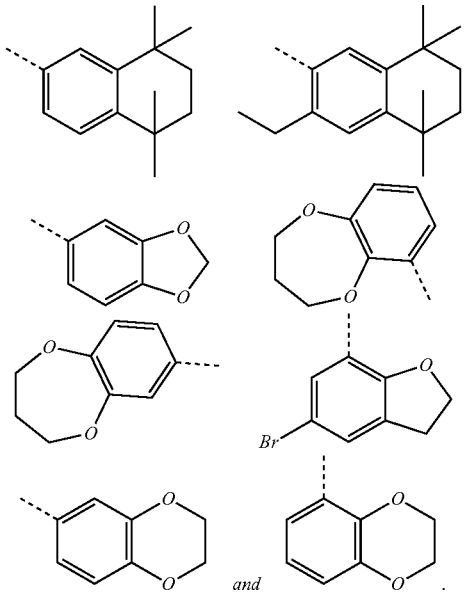

41. The compound of claim 13, wherein $R^3$ is —C(O)$R^6$, and wherein $R^6$ is selected from the group consisting of

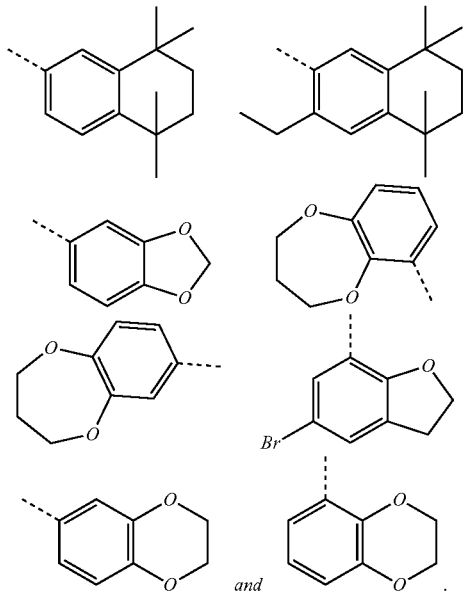

42. A method of treating a patient with a CXC chemokine-mediated disease, comprising administering a therapeutically effective amount of the compound of claim 1 to the patient.

43. The of method claim 42, wherein the CXC chemokine-mediated disease comprises overproduction of glutamic acid-leucine-arginine (ELR)-CXC chemokine.

44. The method of claim 42, wherein the CXC chemokine-mediated disease is a tumor or cancer.

45. The method of claim 42, wherein the CXC chemokine-mediated disease is a pulmonary disease, wherein the pulmonary disease is COPD, asthma, or cystic fibrosis.

46. The method of claim 42, wherein the CXC chemokine-mediated disease is multiple sclerosis.

47. The method of claim 42, wherein the CXC chemokine-mediated disease is rheumatoid arthritis or psoriasis.

48. The method of claim 42, wherein the solvated or unsolvated form, the salt, or the composition is administered to the patient in combination with a second medicament useful for treating the CXC chemokine-mediated disease.

49. The method of claim 48, wherein second medicament is a anti-rheumatic drug, a nonsteroidal anti-inflammatory drug, a COX-2 selective inhibitor, a COX-1 inhibitor, an immunosuppressive, a steroid, a biological response modifier, or other anti-inflammatory agent or therapeutics useful for the treatment of CXC chemokine mediated diseases.

50. The method of claim 48, wherein the CXC chemokine-mediated disease is cancer, and the second medicament is at least one antineoplastic agent selected from the group consisting of gemcitabine, paclitaxel, 5-fluorouracil, cyclophosphamide, temozolomide, and vincristine; or at least one agent selected from the group consisting of microtubule affecting agents, antineoplastic agents, anti-angiogenesis agents, VEGF receptor kinase inhibitors, antibodies against the VEGF receptor, interferon, and radiation.

51. The method of claim 48, wherein the CXC chemokine-mediated disease is a pulmonary disease, wherein the pulmonary disease is COPD, asthma, or cystic fibrosis; and wherein the second medicament is selected from the group consisting of glucocorticoids, 5-lipoxygenase inhibitors, beta-2 adrenoceptor agonists, muscarinic M1 antagonists, muscarinic M3 antagonists, muscarinic M2 agonists, NK3 antagonists, LTB4 antagonists, cysteinyl leukotriene antagonists, bronchodilators, PDE4 inhibitors, PDE inhibitors, elastase inhibitors, MMP inhibitors, phospholipase A2 inhibitors, phospholipase D inhibitors, histamine H1 antagonists, histamine H3 antagonists, dopamine agonists, adenosine A2 agonists, NK1 and NK2 antagonists, GABA-β agonists, nociceptin agonists, expectorants, mucolytic agents, decongestants, antioxidants, anti-IL-8 antibodies, anti-IL-5 antibodies, anti-IgE antibodies, anti-TNF antibodies, IL-10, adhesion molecule inhibitors, and growth hormones.

52. The method of claim 48, wherein the CXC chemokine-mediated disease is multiple sclerosis, wherein the second medicament is at least one compound selected from the group consisting of glatiramer acetate, glucocorticoids, methotrexate, azothioprine, mitoxantrone, CB2-selective inhibitors, cyclosporin, leflunimide, sulfasalazine, β-methasone, β-interferon, glatiramer acetate, prednisone, etonercept, and infliximab.

53. The method of claim 45, wherein the CXC chemokine-mediated disease is rheumatoid arthritis or psoriasis, wherein the second medicament is at least one compound selected from the group consisting of COX-2 inhibitors, COX-1 inhibitors, immunosuppressives, steroids, PDE 4 inhibitors, anti-TNF-α compounds, MMP inhibitors, glucocorticoids, chemokine inhibitors, and CB2-selective agents.

54. The method of claim 42, wherein pharmaceutical composition is administered orally.

55. The method of claim 42, wherein the pharmaceutical composition is a tablet.

56. A method of using the compound of claim 5 in a pharmaceutical composition, wherein the pharmaceutical composition comprises a therapeutically effective amount of the compound sufficient for treating a CXC chemokine-mediated disease, and wherein the pharmaceutical composition is administered to a patient in need thereof.

57. The method of claim 56, wherein the CXC chemokine-mediated disease is a tumor or cancer.

58. The method of claim 56, wherein the CXC chemokine-mediated disease is a pulmonary disease, wherein the pulmonary disease is COPD, asthma, or cystic fibrosis.

59. The method of claim 56, wherein the CXC chemokine-mediated disease is multiple sclerosis.

60. The method of claim 56, wherein the CXC chemokine-mediated disease is rheumatoid arthritis or psoriasis.

61. The method of claim 56, wherein the pharmaceutical composition is administered to the patient in combination with a second medicament useful for treating the CXC chemokine-mediated disease.

62. The method of claim 56, wherein pharmaceutical composition is administered orally.

63. The method of claim 62, wherein the pharmaceutical composition is a tablet.

64. A method of using the compound of claim 6 in a pharmaceutical composition, wherein the pharmaceutical composition comprises a therapeutically effective amount of the compound sufficient for treating a CXC chemokine-mediated disease, and wherein the pharmaceutical composition is administered to a patient in need thereof.

65. The method of claim 64, wherein the CXC chemokine-mediated disease is a tumor or cancer.

66. The method of claim 64, wherein the CXC chemokine-mediated disease is a pulmonary disease, wherein the pulmonary disease is COPD, asthma, or cystic fibrosis.

67. The method of claim 64, wherein the CXC chemokine-mediated disease is multiple sclerosis.

68. The method of claim 64, wherein the CXC chemokine-mediated disease is rheumatoid arthritis or psoriasis.

69. The method of claim 64, wherein the pharmaceutical composition is administered to the patient in combination with a second medicament useful for treating the CXC chemokine-mediated disease.

70. The method of claim 64, wherein the pharmaceutical composition is administered orally.

71. The method of claim 70, wherein the pharmaceutical composition is a tablet.

72. A method of using the compound of claim 16 in a pharmaceutical composition, wherein the pharmaceutical composition comprises a therapeutically effective amount of the compound sufficient for treating a CXC chemokine-mediated disease, and wherein the pharmaceutical composition is administered to a patient in need thereof.

73. The method of claim 72, wherein the CXC chemokine-mediated disease is a tumor or cancer.

74. The method of claim 72, wherein the CXC chemokine-mediated disease is a pulmonary disease, wherein the pulmonary disease is COPD, asthma, or cystic fibrosis.

75. The method of claim 72, wherein the CXC chemokine-mediated disease is multiple sclerosis.

76. The method of claim 72, wherein the CXC chemokine-mediated disease is rheumatoid arthritis or psoriasis.

77. The method of claim 72, wherein the pharmaceutical composition is administered to the patient in combination with a second medicament useful for treating the CXC chemokine-mediated disease.

78. The method of claim 72, wherein the pharmaceutical composition is administered orally.

79. The method of claim 78, wherein the pharmaceutical composition is a tablet.

80. A compound comprising a compound from formula (1):

(1)

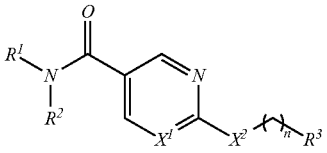

wherein $R^1$ is selected from the group consisting of hydrogen, heteroalkyl, alkyl, aryl, arylalkyl, heteroaryl, heteroarylalkyl, heteroarylaryl, arylheteroaryl, heteroarylheteroaryl, heterocyclylaryl, cycloalkyl, cycloalkylalkyl, heterocyclyl, and heterocycloalkylalkyl;

wherein $R^2$ is selected from the group consisting of heteroalkyl, n-propyl, isopropyl, n-butyl, t-butyl, n-pentyl, $C_{7-25}$ alkyl, aryl, arylalkyl, heteroaryl, heteroarylalkyl, heteroarylaryl, arylheteroaryl, heteroarylheteroaryl, heterocyclylaryl, cycloalkyl, cycloalkylalkyl, heterocyclyl, and heterocycloalkylalkyl, wherein aryl in $R^2$ is unsubstituted or substituted with one or more substituents selected from —C(O)R, —OR, alkyl, aryl, —N(H)R, —N(R)R, —S—R, —$N_3$, —B(R)R, —$B(OH)_2$, —$B(OR)_2$, —C(O)OH, —C(O)OR, —C(O)$NH_2$, —S(O)$_2$ $NH_2$, —C(O)N(H)R, —C(O)N(R)R, —SH, —S—R, —$NO_2$, cyano, halo, haloalkyl, haloalkoxy, heterocyclyl, heteroalkyl, —OH, —OC(O)R, —C(O)R, and —C(O)$CH_aX_b$, wherein a+b=3 and X is F, Cl or Br, and wherein R is alkyl having less than twelve carbons;

wherein $R^3$ is —B($R^4R^5$), —$R^6$—B($R^4R^5$), substituted aryl, arylalkyl, cycloalkyl, heteroaryl, heteroarylalkyl, heterocyclyl or heterocycloalkylalkyl where the heterocyclyl is selected from the group consisting of lactam, lactone, thiazolidinyl, 1,3-tetrahydrothiophenyl and tetrahydrothiopyranyl, heteroarylaryl, arylheteroaryl, heteroarylheteroaryl, heterocyclylaryl, —C(O)—$R^6$, —O—$R^6$, —S(O)$_y$—$R^6$ (wherein y=0, 1, or 2), —P(O)—($R^4R^5$), and —N($R^7R^8$);

wherein $R^6$ is selected from the group consisting of alkyl, aryl, arylalkyl, cycloalkyl, heteroaryl, heteroarylalkyl, heterocyclyl, heterocycloalkylalkyl, alkylaryl, arylheteroaryl, heteroarylaryl, heterocyclylaryl;

wherein $R^4$ and $R^5$ are independently selected from the group consisting of hydrogen, hydroxyl, aryloxy, and alkoxy, or wherein $R^4$ and $R^5$ together form a cyclic ester, or an acid anhydride (either mixed or symmetrical);

wherein $R^7$ and $R^8$ are independently selected from the group consisting of from hydrogen, alkyl, haloalkyl, aryl, cycloalkyl, arylalkyl, heteroalkyl, heterocyclyl, and heterocycloalkylalkyl; $R^7$ and $R^8$ are both oxygen; or $R^7$ and $R^8$ form a heterocyclyl; and wherein $X^1$ is —CH— or —CCl—, $X^2$ is oxygen; and n is an integer between 1 and 8;

a pharmaceutically acceptable solvated or unsolvated form thereof; a pharmaceutically acceptable salt thereof; or a pharmaceutical composition thereof.

* * * * *